United States Patent
Bertin et al.

(10) Patent No.: US 9,340,567 B2
(45) Date of Patent: May 17, 2016

(54) CHEMISTRY USED IN BIOSENSORS

(71) Applicant: OHMX CORPORATION, Evanston, IL (US)

(72) Inventors: Paul A. Bertin, Chicago, IL (US); Michael J. Ahrens, Evanston, IL (US)

(73) Assignee: OHMX Corporation, Evanston, IL (US)

( * ) Notice: Subject to any disclaimer, the term of this patent is extended or adjusted under 35 U.S.C. 154(b) by 657 days.

(21) Appl. No.: 13/667,713

(22) Filed: Nov. 2, 2012

(65) Prior Publication Data

US 2013/0112572 A1    May 9, 2013

Related U.S. Application Data

(60) Provisional application No. 61/555,945, filed on Nov. 4, 2011.

(51) Int. Cl.
| | |
|---|---|
| *G01N 27/327* | (2006.01) |
| *C07F 17/02* | (2006.01) |
| *C08F 4/6192* | (2006.01) |
| *C12Q 1/00* | (2006.01) |
| *G01N 33/543* | (2006.01) |

(52) U.S. Cl.
CPC ............ *C07F 17/02* (2013.01); *C08F 4/61925* (2013.01); *C12Q 1/001* (2013.01); *C12Q 1/004* (2013.01); *G01N 33/5438* (2013.01); *G01N 27/3271* (2013.01)

(58) Field of Classification Search
CPC ............ C08F 4/61922; C08F 4/61925; B01J 31/2295; C07F 17/02; G01N 27/3271; G01N 27/3275; G01N 27/3276; C12Q 1/004
See application file for complete search history.

(56) References Cited

U.S. PATENT DOCUMENTS

| | | | |
|---|---|---|---|
| 4,247,533 A | 1/1981 | Cerami et al. | |
| 4,304,853 A | 12/1981 | Jozefonvicz et al. | |
| 4,469,863 A | 9/1984 | Ts'o et al. | |
| 4,727,036 A | 2/1988 | Knowles et al. | |
| 4,806,468 A | 2/1989 | Wagner et al. | |
| 5,034,506 A | 7/1991 | Summerton et al. | |
| 5,206,144 A | 4/1993 | Zeuthen et al. | |
| 5,216,141 A | 6/1993 | Benner | |
| 5,235,033 A | 8/1993 | Summerton et al. | |
| 5,270,163 A | 12/1993 | Gold et al. | |

(Continued)

FOREIGN PATENT DOCUMENTS

| | | |
|---|---|---|
| EP | 2 075 339 | 7/2009 |
| WO | WO 90/01559 | 2/1990 |

(Continued)

OTHER PUBLICATIONS

Wang et al., "Attachment of Amine- and Maleimide-Containing Ferrocene Derivatives onto Self-Assembled Alkanethiol and Alkanedithiol Monolayers: Voltammetreic Evaluation of Cross-Linking Efficiencies and Surface Coverage of Electroactive Groups," Electroanalysis 0000, 00, 0-0 (Galley Proof), 2004, pp. 1-7.*

(Continued)

*Primary Examiner* — Alex Noguerola
(74) *Attorney, Agent, or Firm* — Wolf, Greenfield & Sacks, P.C.

(57) ABSTRACT

The invention relates to novel compositions of 1,3-disubstituted ferrocenes useful for the modification of electrodes.

30 Claims, 27 Drawing Sheets

(56) References Cited

U.S. PATENT DOCUMENTS

| | | | |
|---|---|---|---|
| 5,386,023 A | 1/1995 | Sanghvi et al. |
| 5,407,759 A | 4/1995 | Ohsuga |
| 5,475,096 A | 12/1995 | Gold et al. |
| 5,567,588 A | 10/1996 | Gold et al. |
| 5,595,877 A | 1/1997 | Gold et al. |
| 5,602,240 A | 2/1997 | De Mesmaeker et al. |
| 5,620,850 A | 4/1997 | Bamdad et al. |
| 5,637,459 A | 6/1997 | Burke et al. |
| 5,637,684 A | 6/1997 | Cook et al. |
| 5,644,048 A | 7/1997 | Yau |
| 5,654,159 A | 8/1997 | Allard et al. |
| 5,683,867 A | 11/1997 | Biesecker et al. |
| 5,705,337 A | 1/1998 | Gold et al. |
| 5,804,400 A | 9/1998 | Martin et al. |
| 5,834,224 A | 11/1998 | Ruger et al. |
| 6,013,170 A | 1/2000 | Meade |
| 6,013,459 A | 1/2000 | Meade |
| 6,103,033 A | 8/2000 | Say et al. |
| 6,162,645 A | 12/2000 | Lee et al. |
| 6,248,229 B1 | 6/2001 | Meade |
| 6,348,319 B1 | 2/2002 | Braach-Maksvytis et al. |
| 6,432,723 B1 | 8/2002 | Plaxco et al. |
| 6,495,336 B1 | 12/2002 | Ludin et al. |
| 6,600,026 B1 | 7/2003 | Yu |
| 6,676,816 B2 | 1/2004 | Mao et al. |
| 6,740,518 B1 | 5/2004 | Duong et al. |
| 6,750,016 B2 | 6/2004 | Mirkin et al. |
| 6,770,190 B1 | 8/2004 | Milanovski et al. |
| 6,927,039 B2 | 8/2005 | Gilardi et al. |
| 6,932,894 B2 | 8/2005 | Mao et al. |
| 6,942,771 B1 | 9/2005 | Kayyem |
| 6,991,926 B2 | 1/2006 | Schmid et al. |
| 7,018,523 B2 | 3/2006 | Meade |
| 7,160,678 B1 | 1/2007 | Kayyem et al. |
| 7,223,837 B2 | 5/2007 | De Groot et al. |
| 7,267,939 B2 | 9/2007 | Meade |
| 7,312,087 B2 | 12/2007 | Duong et al. |
| 7,332,369 B2 | 2/2008 | Veres et al. |
| 7,384,749 B2 | 6/2008 | Kayyem et al. |
| 7,393,645 B2 | 7/2008 | Kayyem et al. |
| 7,514,228 B2 | 4/2009 | Meade |
| 7,560,237 B2 | 7/2009 | O'Connor et al. |
| 7,566,534 B2 | 7/2009 | Meade |
| 7,579,145 B2 | 8/2009 | Meade |
| 7,582,419 B2 | 9/2009 | Meade |
| 7,595,153 B2 | 9/2009 | Meade |
| 7,601,507 B2 | 10/2009 | O'Connor et al. |
| 7,705,045 B2 | 4/2010 | De Groot et al. |
| 7,713,711 B2 | 5/2010 | O'Connor et al. |
| 7,728,094 B2 | 6/2010 | Zhou et al. |
| 7,732,140 B2 | 6/2010 | Vandenbark et al. |
| 7,759,073 B2 | 7/2010 | O'Connor et al. |
| 7,759,114 B2 | 7/2010 | Martin et al. |
| 7,803,572 B2 | 9/2010 | Braven et al. |
| 7,807,835 B2 | 10/2010 | Xie et al. |
| 8,114,661 B2 | 2/2012 | O'Connor et al. |
| 8,530,170 B2 | 9/2013 | Bertin |
| 8,734,631 B2 | 5/2014 | Ahrens et al. |
| 8,802,390 B2 | 8/2014 | Ahrens et al. |
| 8,951,400 B2 | 2/2015 | Ahrens et al. |
| 2002/0009810 A1 | 1/2002 | O'Connor et al. |
| 2002/0121314 A1 | 9/2002 | Tao et al. |
| 2003/0073243 A1 | 4/2003 | Law et al. |
| 2003/0119208 A1 | 6/2003 | Yoon et al. |
| 2005/0003398 A1 | 1/2005 | Tao et al. |
| 2005/0123948 A1 | 6/2005 | Claycomb et al. |
| 2005/0136394 A1 | 6/2005 | Fang et al. |
| 2005/0189240 A1 | 9/2005 | Lin et al. |
| 2006/0003382 A1 | 1/2006 | Eckermann et al. |
| 2006/0073532 A1 | 4/2006 | Meade |
| 2008/0164154 A1 | 7/2008 | Purvis |
| 2008/0248592 A1 | 10/2008 | Bamdad et al. |
| 2009/0041791 A1 | 2/2009 | Feng |
| 2009/0253149 A1 | 10/2009 | Ahrens et al. |
| 2010/0003710 A1 | 1/2010 | Bertin et al. |
| 2010/0025264 A1 | 2/2010 | Yuan et al. |
| 2010/0145036 A1 | 6/2010 | Sufi et al. |
| 2010/0204554 A1 | 8/2010 | Say et al. |
| 2011/0033869 A1 | 2/2011 | Bertin |
| 2012/0012472 A1 | 1/2012 | Ahrens et al. |
| 2012/0034638 A1 | 2/2012 | Ahrens et al. |
| 2012/0156709 A1 | 6/2012 | Bertin et al. |
| 2012/0181186 A1 | 7/2012 | Bertin et al. |
| 2012/0199499 A1 | 8/2012 | O'Connor et al. |
| 2013/0098777 A1 | 4/2013 | Gaustad |
| 2013/0112572 A1* | 5/2013 | Bertin et al. ............... 205/777.5 |
| 2013/0236909 A1 | 9/2013 | Bertin |
| 2013/0264220 A1 | 10/2013 | Bertin et al. |
| 2014/0027309 A1 | 1/2014 | Bao et al. |
| 2014/0027310 A1 | 1/2014 | Gaustad et al. |
| 2014/0134658 A1 | 5/2014 | Ahrens et al. |
| 2014/0311922 A1 | 10/2014 | Ahrens et al. |
| 2014/0322740 A1 | 10/2014 | Ahrens et al. |
| 2014/0342383 A1 | 11/2014 | Bertin et al. |

FOREIGN PATENT DOCUMENTS

| | | |
|---|---|---|
| WO | WO 93/03379 | 2/1993 |
| WO | WO 97/21431 | 6/1997 |
| WO | WO 98/20162 | 5/1998 |
| WO | WO 98/57158 | 12/1998 |
| WO | WO 98/57159 | 12/1998 |
| WO | WO 99/57317 A1 | 11/1999 |
| WO | WO 00/11474 | 3/2000 |
| WO | WO 03/19171 | 3/2003 |
| WO | WO 2004/079848 | 9/2004 |
| WO | WO 2008/045799 | 4/2008 |
| WO | WO 2009/052422 | 4/2009 |
| WO | WO 2010/142037 | 12/2010 |
| WO | WO 2011/034668 | 3/2011 |
| WO | WO 2011/041586 | 4/2011 |
| WO | WO 2011/150186 | 12/2011 |
| WO | WO 2012/100078 | 7/2012 |

OTHER PUBLICATIONS

Eggers et al., "The Effect of Surface Polarity on the Electrochemical Double Layer and Its Influence on the Measurement of the Standard Rate Constant of Electron Transfer," J. Phys. Chem. C 2009, 113, 8964-8971.*

Deschenaux et al., "Novel 1,1'- and 1,3 Disubstituted Ferrocene-containing Thermotropic Liquid Crystals: A Remarkable Isomeric Effect," J. Chem. Soc., Chem. Commun., 1991, pp. 909-910.*

Liu et al., "Feature of Entrapment of Glucose Oxidase in Regenerated Silk Fibroin Membranes and Fabrication of a 1,1'-Dimethylferrocene-mediating Glucose Sensor," Microchemical Journal 53, 241-252 (1996).*

Ferber et al., "A New Efficient Route to Chiral 1,3-Disubstituted Ferrocenes: Application to the Synthesis of (Rp)- and (Sp)-17α-(3'-formylferrocenyl)ethynyl]estradiol," Chem. Eur. J. 2006, 12, 2081-2086.*

STN Database; Chemical Abstracts Service, Bertin, Electrochemical assay for the detection of enzymes and botulin. Accession No. 2009:490555.

STN Database; Chemical Abstracts Service, Bertin et al., Enzyme-triggered redox altering chemical elimination (E-TRACE) immunoassay. Accession No. 2012:1050657.

Abel et al, Comprehensive Organometallic Chemistry II, A Review of the Literature 1982-1994, vol. 7, Chaps. 7, 8, 10 &11, Pergamon Press.

Adams et al., New members of the [Ru(diimine)(CN)(4)](2-) family: structural, electrochemical and photophysical properties. Dalton Trans. Jan. 7, 2006;(1):39-50. Epub Sep. 14, 2005.

Adjemian et al., Cleavage-sensing redox peptide monolayers for the rapid measurement of the proteolytic activity of trypsin and α-Thrombin Enzymes. Langmuir. 2010;26(12):10347-10356.

Ahn-Yoon et al., "Ganglioside-liposome immunoassay for the detection of botulinum toxin," Anal. Bioanal. Chem. 378:68-75 (2004).

Ahrens et al., Spectroscopic and redox properties of amine-functionalized K2[OsII(bpy)(CN)4] complexes. Dalton Trans. Feb. 28, 2011;40(8):1732-6. Epub Jan. 18, 2011.

(56) References Cited

OTHER PUBLICATIONS

Alston et al., Cyclodextrins as Second Sphere Ligands for Transition Metal Complexes—the X-Ray Crystal Structure of [Rh(cod)(NH.sub.3).sub.2 .alpha.-cyclodextrin][PF.sub.6.cndot.6H2O**. Angew. Chem. Int. Ed. Engl. 24(9):786-787 (1985).
Amorim et al., "Nuclear Magnetic Resonance Studies of the ProtonationSequence of Some Oxaaza Macrocyclic Compounds," J. Chem. Soc. Dalton Trans. 3449-3455 (1990).
Ando et al., "Effect of Second-Sphere Coordination. 4. Factors Influencing the Electrochemical Behavior of Ruthenium-Ammine Complexes Cause by Second-Sphere Coordination of Crown Ethers," Inorg. Chem. 35:3504-3508 (1996).
Ando et al., The effect of second-sphere coordination-II. Adduct formation between [Ru(NH.sub.3)5L](PF.sub.6).sub.n (n=2 and 3) and 18-crown-6 ether in solution and the effect on redox behavior. Polyhedron 11(18):2335-2340 (1992).
Ando et al.,"The Effect of Second-Sphere Coordination. 7. Isolation of 18-Crown-6 Ether Adducts of Ruthenium-Ammine Complexes," Inorg. Chim. Acta. 282:247-251 (1998) [bb 5001].
Ando, "Hydrogen bonding of 18-crown-6 ether to ruthenium-ammine complexes at second sphere," Coordination Chemistry Reviews 248:185-203 (2004).
Anne et al., High-throughput fluorogenic assay for determination of botulinum type B neurotoxin protease activity. Anal Biochem. Apr. 15, 2001;291(2):253-61. (Abstract Only).
Appoh et al., "Electrochemical Investigations into the Binding of Some Nonredox Active Metal Ions to Surface-Bound Glutamic Acid Conjugates," J. Phys. Chem. C 111:4235-4245 (2007).
Arion et al., "Potassium-controlled synthesis of heterotopic macrocycles based on isothiosemicarbazide," Inorg. Chim. Acta 328:123-133 (2002).
Baca et al., [Os(bipy)(CN)4]2- and its relatives as components of polynuclear assemblies: structural and photophysical properties. Inorg Chem. Nov. 12, 2007;46(23):9779-89. Epub Oct. 2, 2007.
Barker et al. Protein binding and the electronic properties of iron(II) complexes: an electrochemical and optical investigation of outer sphere effects. Bioconjug Chem. Oct. 21, 2009;20(10):1930-9. (Abstract Only).
Batchelor et al., A resorufin-based fluorescent assay for quantifying NADH. Anal Biochem. Jun. 1, 2002;305(1):118-9.
Beaucage et al., The Functionalization of Oligonucleotides via Phosphoramidite Derivatives. Tetrahedron. Mar. 5, 1993; 49(10):1925-63.
Beckett et al., A minimal peptide substrate in biotin holoenzyme synthetase-catalyzed biotinylation. Protein Sci. Apr. 1999;8(4):921-9.
Bertin et al., Novel redox active bifunctional crosslinkers from unsymmetrical 1,1'-disubstituted ferrocenes. Tetrahedron Letters. Sep. 23, 2009; 50(38):5409-12. (Abstract Only).
Bickert et al., Pentafulvenes: versatile synthons in metallocene chemistry. Organometallics. May 1984; 3(5):653-57.
Bignozzi et al., Simple poly(pyridine)ruthenium(II) photosensitizer: (2,2'- bipyridine)tetracyanoruthenate(II). J Am Chem Soc. Nov. 1, 1986;108(24):7872-3.
Bottcher et al., "Spectroscopy and Electrochemistry of Cobalt(III) Schiff Base Complexes ," Inorg. Chem. 36:2498-2504 (1997).
Brill et al., Synthesis of oligodeoxynucleoside phosphorodithioates via thioamidites. J. Am. Chem. Soc. Mar. 1989; 111(6):2321-22.
Bryce et al., "A New Route to 1,4-Disubstituted Cyclohexa-1,3-diene Derivatives: The Synthesis of a Highly Conjugated Bis(benzothiazoline) Derivative," J. Org. Chem. 3399-3401 (1984).
Callahan et al., "Effects of Weak Metal-Metal Interactions in Ligand-Bridged Complexes of Ruthenium. Dimeric Complexes Containing Ruthenium Ions in Different Coordination Environments," Inorg. Chem. 14(7):1443-1453 (1975). (Abstract Only).
Carlsson et al., Screening for genetic mutations. Nature. Mar. 21, 1996;380(6571):207.
Chen et al., Chemically Modified Electrodes by Nucleophilic Substitution of Chlorosilylated Platinum Oxide Surfaces. Langmuir. Sep. 1994; 10(9):3332-7. (First Page Only).

Chen et al., Preparation and electrocatalytic properties of osmium oxide/hexacyanoruthenate films modified electrodes for catecholamines and sulfur oxoanions. J Electroanalytical Chem. 2006, 589:15-23.
Chidsey et al., "Coadsorption of Ferrocene-Terminatd and Unsubstituted Alkanethiols on Gold: Electroactive Self-Assembled Monolayers," J. Am. chem. Soc. 112:4301-4306 (1990).
Chin et al., Microfluidics-based diagnostics of infectious diseases in the developing world. Nat Med. Jul. 2011 31;17(8):1015-9.
Clements et al., "Some 3,9-Dicarboxylic Acids of 2,4,8,10-Tetroxaspirol[5.5]undecane," J. Org. Chem. 24:1958-1961 (1959).
Collman et al., Role of a distal pocket in the catalytic O2 reduction by cytochrome c oxidase models immobilized on interdigitated array electrodes. PNAS. Mar. 9, 2009; 106(18):7320-3.
Connelly et al., Chemical Redox Agents for Organometallic Chemistry. Chem Rev. Mar. 28, 1996;96(2):877-910.
Cotton et al., Advanced Organic Chemistry, 5th Edition, John Wiley & Sons, 1988, p. 38 and Ch 26.
Creutz et al., "Binuclear Complexes of Ruthenium Ammines," J. Am. Chem. Soc. 95:1086-1094 (1973).
Cronan., The E. coli bio operon: transcriptional repression by an essential protein modification enzyme. Cell. Aug. 11, 1989;58(3):427-9.
Curtis et al., "Directed, Intramolecular Electron Transfer in Mixed-Valence Dimers," Inorg. Chem. 24:385-397 (1985).
De Filippis et al., Synthesis of some para-functionalized phenylboronic acid derivatives. Synthetic Communications. Aug. 20, 2006; 32(17):2669-76. (Abstract Only).
De Mesmaeker et al., Comparison of rigid and flexible backbones in antisense oligonucleotides. Bioorganic & Medicinal Chemistry Letters. Feb. 10, 1994; 4(3):395-8. (Abstract Only).
Deinhammer et al., Electrochemical oxidation of amine-containing compounds: a route to the surface modification of glassy carbon electrodes. Langmuir. Apr. 1994; 10(4):1306-13. (Abstract Only).
Dempcy et al. Synthesis of a thymidyl pentamer of deoxyribonucleic guanidine and binding studies with DNA homopolynucleotides. Proc Natl Acad Sci U S A. Jun. 20, 1995;92(13):6097-101.
Dong et al., "Perturbation of the electronic structure of the Creutz-Taube ion via asymmetric encapsulation with macrocyclic ether species," J. Am. Chem. Soc. 115:4379-4380 (1993).
Eckermann et al., "Syntheses of Ru—S Clusters with Kinetically Labile Ligands via the Photolysis of [(cymene).sub.3Ru.sub.3S.sub.2](PF.sub.6).sub.2" Inorg. Chem. 40:1459-1465 (2001).
Egholm et al., Peptide nucleic acids (PNA). Oligonucleotide analogs with an achiral peptide backbone. J. Am. Chem. Soc. Feb. 1992; 114(5):1895-7. (First Page Only).
Ekeroth et al., Electrochemical evaluation of the interfacial capacitance upon phosphorylation of amino acid analogue molecular films. Anal Chem. Sep. 15, 2001;73(18):4463-8.
Eskelinen et al., "The synthesis and electrochemical behavior of ruthenium(III) bipyridine complexes: [Ru(dcbpy)Cl.sub.4] (dcbpy=4,4'-dicarboxylic acid-2,2'-bipyridine) and [Ru(bpy)Cl.sub.311 (L=Ch.sub.30H, PPh.sub.3, 4,4'-bpy, CH.sub.3CN)," Journal of Electroanalytical Chemistry 579:257-265 (2005).
Farrington et al., Synthesis and reactivity of a ferrocene-derived PCP-pincer ligand. Chem Commun (Camb). Feb. 21, 2002;(4):308-9.
Fu et al., "Terminal Ligand Influence on the Electronic Structure and Intrinsic Redox Properties of the [Fe.sub.4S .sub.4].sup.2+ Cubane Clusters," Inorg. Chem 43(12):3647-3655 (2004).
Furholz et al., "The Creutz-Taube Complex Revisited," J. Am. Chem. Soc. 106:121-123 (1984).
Gao et al., Unusual conformation of a 3'-thioformacetal linkage in a DNA duplex. J Biomol NMR. Jan. 1994;4(1):17-34. (Abstract Only).
Gardner et al., Application of conducting polymer technology in microsystems. Sensors and Actuators A: Physical. Oct. 1995; 51(1):57-66. (Abstract Only).
Gassman et al., (Trifluoromethyl)cyclopentadienide: a powerful electron-withdrawing ligand for transition-metal complexes. J. Am. Chem. Soc. Jul. 1986; 106(14):4228-9. (First Page Only).
Gaster et al., nanoLAB: an ultraportable, handheld diagnostic laboratory for global health. Lab Chip. Mar. 7, 2011;11(5):950-6. Epub Jan. 24, 2011.

(56) References Cited

OTHER PUBLICATIONS

Gebbink et al., "Fe.sub.4S.sub.4 Clusters Functionalized with Molecular Receptor Ligands," Eur. J. Inor. Chem. 2087-2099 (2000).
Geiger et al., The Electron-Transfer Reactions of Mononuclear Organotransition Metal Complexes. Advances in Organometallic Chemistry. 1984; 23:1-93.
Geiger et al., The Electron-Transfer Reactions of Polynuclear Organotransition Metal Complexes. Advances in Organometallic Chemistry. 1985; 24:87-130.
Gerhardt, "Investigations of Metal-Coordinated Peptides as Supramolecular Synthons," J. Org. Chem. 71:6333-6341 (2006).
Gianneschi et al., "Signal Amplification and Detection via a Supramolecular Allosteric Catalyst," J. Am. Chem. Soc. 127:1644-1645 (2005).
Giordano et al., Biopanning and rapid analysis of selective interactive ligands. Nat Med. Nov. 2001;7(11):1249-53. (Abstract Only).
Grancharov et al., "Individually addressable recessed gold microelectrode arrays with monolayers of thio-cyclodextrin nanocavities," Analyst 130:1351-1357(2005).
Gray, "Electron Transfer in Proteins," Ann. Rev. Biochem. 65:537 561(1996).
Hallis et al., "Development of Novel Assays for Botulinum Type A and B Neurotoxins Based on Their Endopeptidase Activities," J. Clin. Microbiol. 34:1934-1938 (1996).
Heinze et al., "Anion-Induced Motion in a Ferrocene Diamide," Eur. J. Inorg. Chem. 66-71 (2005). (Abstract Only).
Heinze et al., "Main Chain Ferrocenyl Amides from 1-aminoferrocene-1'-carboxylic Acid," Eur. J. Inorg. Chem. 2974-2988 (2004). (Abstract Only).
Hickman et al., Molecular self-assemble of two-terminal, voltammetric microsensors with internal references. Science, 1991. 252:688-91.
Holleman et al., "Inorganic Chemistry," Academic Press 1616-1627 (2001).
Horn et al., Oligonucleotides with alternating anionic and cationic phosphoramidate linkages: Synthesis and hybridization of stereouniform isomers. Tetrahedron Letters. Feb. 5, 1996; 37(6):743-46. (Abstract Only).
Houseman et al., Maleimide-functionalized self-assembled monolayers for the preparation of peptide and carbohydrate biochips. Langmuir, 2003, 19:1522-31.
Houseman et al., Peptide chips for the quantitative evaluation of protein kinase activity. Nat Biotechnol. Mar. 2002;20(3):270-4.
Hudson et al., Ferrocene polymers: current architectures, syntheses and utility. J. Organo. Chem. Dec. 3, 2001; 637-639:47-69. (Abstract Only).
Illingworth, "Phosphofructokinase regulation," School of Biochemistry and Microbiology, University of Leeds, BIOC2120 Lectures 2007 (Aug. 5, 2007), p. 4-6.
Isied et al., "Effects of SO.sub.2, HSO.sub.3, and SO.sub.3.sup.2- as Auxiliary Ligands on the Reactivity of Ammineruthenium(II)-Ligand Bonds," Inorg. Chem. 13(7):1545-1551 (1974).
Isied et al., "Peptide Formation in the Presence of a Metal Ion Protecting Group. Pentaamine Cobalt(III)-Peptide Complexes," J. Am. Chem. Soc. 100(21):6752-6754 (1978).
Isied et al., "Rates of Intermolecular Electron Transfer," J. Am. Chem. Soc. 95(24):8198-8200 (1973).
Jeffrey et al., "Metal Complexes of Hemilabile Ligands. Reactivity and Structure of Dichlorobi(o-(diphenylphosphino)anisole)ruthenium(II)," Inorg. Chem. 18(10):2658-2666 (1979).
Jenkins et al., The biosynthesis of carbocyclic nucleosides. Chem. Soc. Rev. 1995. 24:169-176. (First Page Only).
Jung et al., Hybridization of Alternating Cationic/Anionic Oligonucleotides to RNA Segments. Nucleosides and Nucleotides. Jul. 1, 1994; 13(6-7):1597-1605. (Abstract Only).
Jwo et al., "Intramolecular Electron Transfer from Pentacyanoferrate(II) to Pentaamminecobalt(III) Mediated by Various 4,4'-Bipyridines," J. Am. Chem. Soc. 101:6189-6197 (1979). (Abstract Only).
Kamidate et al., Firefly bioluminescent assay of ATP in the presence of ATP extractant by using liposomes. Anal Chem. Jan. 1, 2006;78(1):337-42.
Kanatzidis et al., "A New Iron-Sulphide Cluster Containing the 'Prismane' (Fe6(mu-S6]3+ Core. Synthesis, Structure, and Properties of [Et4N]3[FeS6C16]," J. Chem.Soc., Chem. Commun. 356-358 (1984).
Karyakin, "Prussian Blue and its analogues: electrochemistry and analytical applications," Electroanalysis, 13(10):813-819 (2001).
Kato, Exited-state properties of a (2,2'-Bipyridine) ruthenium (II) complex [RU(CN)4bpy)]2-, a model of localized excitation. J Phys Chem. 1989, 93:3422-5.
Kerman et al., "An electrochemical approach for the detection of HIV-1 protease," Chem. Commun. 3829-3831 (2007).
Kerman et al., "Electrochemical detection of kinase-catalyzed thiophosphorylation using gold nanoparticles," Chem. Commun. 5019-5021 (2007).
Kerman et al., Electrochemical detection of protein tyrosine kinase-catalysed phosphorylation using gold nanoparticles. Biosens Bioelectron. Jan. 1, 2009;24(5):1484-9. Epub Nov. 6, 2008.
Kerman et al., Peptide biosensors for the electrochemical measurement of protein kinase activity. Anal Chem. Dec. 15, 2008;80(24):9395-401.
Khan et al., "Surface Studies of Aminoferrocene Derivatives on Gold: Electrochemical Sensors for Chemical Warfare Agents," Anal. Chem. 79(7):2877-2884 (2007).
Kim et al., Gold-film array-electrode for electrochemical Elisa. Sensors and Actuators B. 2005; 111-2:463-9.
Kitano et al., Self-assembled monolayer of a pepstatin fragment as a sensing element for aspartyl proteases. Anal Chem. Mar. 15, 2005;77(6):1588-95.
Kothari et al., "Cobalt(III) Complexes of Cysteine and Cysteine Derivatives," Inorg. Chem. 8:2276-2280 (1969).
Labib et al., A bioorganometallic approach for rapid electrochemical analysis of human immunodeficiency virus type-1 reverse transcriptase in serum. Elsevier. Article in Press. Electrochimica Acta. Available online Mar. 22, 2011. p. 1-7. doi:10.1016/j.electacta.2011.03.063.
Lavallee et al., "Charge Delocalization in Pentaammineruthenium(II)Complexes. I. Spectral Properties, Basicities, and ChargeDensities by Nuclear Magnetic Resonance Spectroscopy," J. am. Chem. Soc. 94(8):2583-2599 (1972). (Abstract Only).
Leinonen et al., Development of novel peptide ligands modulating the enzyme activity of prostate-specific antigen. Scand J Clin Lab Invest Suppl. 2000;233:59-64.
Lenhard et al., Chemically modified electrodes: Part VII. Covalent bonding of a reversible electrode reactant to Pt electrodes using an organosilane reagent. J. Electroanal. Chem. May 10, 1977; 78(1):195-201.
Letsinger et al., Cationic Oligonucleotides. J. Am. Chem. Soc. Jun. 1, 1988; 110(13):4470-71. (First Page Only).
Letsinger et al., Effects of pendant groups at phosphorus on binding properties of d-ApA analogues. Nucleic Acids Res. Apr. 25, 1986;14(8):3487-99.
Letsinger et al., Phosphoramidate analogs of oligonucleotides. J Org Chem. Nov. 1970; 35(11):3800-3. (First Page Only).
Li et al., Development of an ultrafast quantitative heterogeneous immunoassay on prefunctionalized poly(dimethylsiloxane), microfluidic chips for the next-generation immunosensors. Microfluidics and nanofluidics. Mar. 11, 2009;7(4):593-8.
Li et al., Nanoscale 1,3,5,7-tetrasubstituted adamantanes and p-substituted tetraphenyl-methanes for AFM applications. Organic Letters, 2002, 4(21):3631-4. (Abstract Only).
Liu et al., "Protein modulation of electrochemical signals: application to immunobiosensing," Chem.Commun. 3670-3872 (2008).
Liu et al., Electrochemical proteolytic beacon for detection of matrix metalloproteinase activities. J Am Chem Soc. Sep. 27, 2006;128(38):12382-3.
Liu et al., Using azobenzene-embedded self-assembled monolayers to photochemically control cell adhesion reversibly. Angew Chem Int Ed Engl. 2009;48(24):4406-8.

(56) References Cited

OTHER PUBLICATIONS

Llaudet et al., Microelectrode biosensor for real-time measurement of ATP in biological tissue. Anal Chem. May 15, 2005;77(10):3267-73.
Lo et al., Development of highly selective and sensitive probes for hydrogen. Chem Commun (Camb). Nov. 7, 2003;(21):2728-9.
Louie et al., "A cobalt complex that selectively disrupts the structure and function of zinc fingers," Proc. Natl. Acad. Sci. USA 95: 6663-6668 (1998).
Lowe et al., "Transition-metal Complexes of Crown Ether Benzodithiolenes. Part 2. The Effects of Alkali-metal Cation Binding," J. Chem. Soc. Dalton Trans. 3333-3340 (1993).
Luo et al., "Ruthenium Tetraammine Chemistry of Self-Assembled Monolayers on Gold Surfaces: Substitution and Reactivity at the Monolayer Interface," Langmuir 14:3602-3606 (1998).
Maeda et al., "Synthesis of Bis[aminomethyl]crown Ethers," Synthesis Communications 185-187 (1983).
Mag et al., Synthesis and selective cleavage of an oligodeoxynucleotide containing a bridged internucleotide 5'-phosphorothioate linkage. Nucleic Acids Res. Apr. 11, 1991;19(7):1437-41.
Mahmoud et al., "A Bioorganometallic Approach for the Electrochemical Detection of Proteins:A Study on the Interaction of Ferrocene-Peptide Conjugates with Papin in Solution and on Au Surfaces," Chem. Eur. J. 13:5885-5895 (2007).
Martic et al., Enzymatically modified peptide surfaces: towards general electrochemical sensor platform for protein kinase catalyzed phosphorylations. Analyst. Jan. 7, 2011;136(1):107-12. Epub Nov. 2, 2010.
Martic et al., Probing the role of the linker in ferrocene-ATP conjugates: monitoring protein kinase catalyzed phosphorylations electrochemically. Chemistry. Jun. 6, 2011;17(24):6744-52. Epub May 3, 2011.
Martic et al., Use of 5-y-Ferrocenyl Adenosine Triphosphate (Fc-ATP) Bioconjugates Having Poly (ethylene glycol) Spacers in Kinase-Catalyzed Phosphorylations. Bioconjugate Chem. 2011. p. 1-10.
Masar et al., "Fine-Tuning the Weak-Link Approach: Effect of Ligand Electron Density on the Formation of Thodium(I) and Iridium(I) Metallomacrocycles," Inorg. Chem. 42(21):6851-6858 (2003).
Meier et al., Peptide Nucleic Acids(PNAs)—Unusual Properties of Nonionic Oligonucleotide Analogues. Anger. Chem. Int. Ed. Engl. Aug. 1992; 31(8):1008-10. (Abstract Only).
Meyerhoff et al., Novel nonseparation sandwich-type electrochemical enzyme immunoassay system for detecting marker proteins in undiluted blood. Clin Chem. Sep. 1995;41(9):1378-84.
Moscherosch et al., "Tetranuclear Pentaammineruthenium Complexes Bridged by .pi.-Conjugated Tetracyano Ligands Related to TCNE; Syntheses and Spectroscopy of Different Oxidation States," Inorg. Chem. 34:4326-4335 (1995).
Moutet et al., "Heterodinucleating macrocyclic compounds designed for electrochemical recognition," Electrochimica Acta 46:2733-2740 (2001).
Murphy et al., Measurement in vitro of human plasma glycerol with a hydrogen peroxide detecting microdialysis enzyme electrode. Anal Chem. Dec. 1, 1994;66(23):4345-53.
Nagy et al., Screen-printed amperometric microcell for proline iminopeptidase enzyme activity assay. Biosens Bioelectron. Aug. 2000;15(5-6):265-72.
Neyhart et al., "Solvent-Induced Electron Transfer and Delocalization in Mixed-Valence Complexes. Electrochemistry," J. Am. Chem. Soc. 118:3724-29 (1996). (Abstract Only).
Nguyen et al., "An Affinity-Based Method for the Purification of Fluorescently-Labeled Biomolecues," Bioconjugate Chem. 17:869-872 (2006).
Orlowski et al., "Electrodeposition of ferrocenoyl peptide disulfides," Chem. Commun., 1330-1332 (2005).
Orlowski et al., "Reorganization Energies of Ferrocene-Peptide Monolayers," Langmuir 23:12765-12770 (2007).
Pauwels et al., Biological Activity of New 2-5A Analogues. Chemica Scripta. 1986; 26:141-9.
Perry-Feigenbaum et al., The pyridinone-methide elimination. Org Biomol Chem. Dec. 7, 2009;7(23):4825-8. (Abstract Only).
Peruski et al., "Rapid and sensitive detection of biological warfare agents using time-resolved fluorescence assays," J. Immunol Methods 263:35-41 (2002).
Pichon et al., A direct meta-lithiation route to 1,3-disubstituted ferrocenes. Chem. Commun. Feb. 10, 2004; 5:598-9.
Plumb et al., "Interaction of a Ferrocenoyl-Modified Peptide with Papin:Toward Protein-Sensitive Electrochemical Probes," Bioconjugate Chem. 14:601-606 (2003).
Rawls, "Optimistic About Antisense," C&EN 35-39 (1997).
Ricci et al., "Sensor and biosensor preparation, optimisation and applications of Prussian Blue modified electrodes," Biosensors & Bioelectronics 21(3):389-407 (2005).
Richardson et al., "Electronic Interactions in Mixed-Valence Molecules as Mediated by Organic Bridging Groups," J. Am. Chem. Soc. 105:40-51 (1983) (bb 5001).
Richardson et al., Preparation and Properties of Mixed-Valence (mu-Dinitrogen)bis(pentaamine) Complexes of Osmium and Ruthenium,Rawls, C & E News p. 35, Jun. 2, 1997 Inorg. Chem. 21:3136-3140 (1982).
Robbins et al., Syntheses and electronic structures of decamethylmetallocenes. J. Am. Chem. Soc. Apr. 1982; 104(7):1882-93. (First Page Only).
Rosa et al., "Crown-Ether-Functionalized Nickel Salicylaldimine Complexes Structural Characterization of Their Potassium, Cesium, and Hexylammonium Derivatives andTheir Use in The Transport of Amino Acids," Inorg. Chem. 37:2328-2329(1998).
Sagi et al. Amperometric assay for aldolase activity: antibody-catalyzed ferrocenylamine formation. Anal Chem. Mar. 1, 2006;78(5):1459-61. (Abstract Only).
Sawai et al., Synthesis and properties of oligoadenylic acids containing 2'-5' phosphoramide linkage Chemistry Letters. 1984. 5:805-08.
Schiavo et al., "Botulinum neurotoxins seotypes A and E cleave SNAP-25 at distance COOH-terminal peptide bonds," FEBS Letters 335(1):99-103 (1993).
Schiavo et al., "Identification of the Nerve Terminal Targets of Botulinum Neurotoxin Serotypes A,D, and E," JBC 268(32):23784-23787 (1993).
Schilt, Mixed ligand complexes of Iron (II) and (III) with cyanide and aromatic di-imines. J Am Chem Soc. 1960;82(12):3000-5.
Schmidt et al., "Fluorigenic Substrates for the Protease Activities of Botulinum Neuroxtoxins, Serotypes A, B, and F," Appl. Environ. Microbiol. 69(1):297-303 (2003).
Scott et al., "Stabilization of Organometallic SpeciesAchieved by the Use of N-Heterocyclic Carbene (NHC) Ligands," Eur. J. Inorg. Chem 1815-1828 (2005).
Seidel et al., "Coordination chemistry of N-Alkylbenzamide-2,3-dithiolates as an Approach to Poly(dithiolate) Ligands: 1,4-Bis[(2,3-dimercaptobenzamido)methylibenzene and Its Chelate Complex with the ($C_5H_5$)Ti Fragment," Inorg. Chem.37:6587-6596 (1998).
Sella et al. Self-immolative dendritic probe for direct detection of triacetone triperoxide. Chem Commun (Camb). Nov. 30, 2008;(44):5701-3. (Abstract Only).
Shone et al., "Proteolytic cleavage of synthetic fragments of vesicle-associated membgrane protein, isoform-2 by botulinum type B neurotoxin," Eur. J. Biochem 217:965-971 (1993).
Shults et al., "Versatile Fluorescence Probes of Protein Kinase Activity," J. Am. Chem. Soc. 125:14248-14249 (2003).
Sidhu et al., Phage display for selection of novel binding peptides. Methods Enzymol. 2000;328:333-63. (Abstract Only).
Silverman et al., "Multivalent avimer proteins evolved by exon shuffling of a family of human receptor domains," Nature Biotechnology 23:1556-1561 (2005). (Abstract Only).
Sizova et al., "Substituents effect on the electronic structure, spectra and photochemistry of $[Ru(NH_3)_5(PY-X)]^{2+}$ complexes," Inorg. Chim. Acta 357:354-360 (2004).
Song et al., "Electrochemical detection of kinase-catalyzed phosphorylation using ferrocene-conjugated ATP;" Chem. Commun. 502-504 (2008).

(56) References Cited

OTHER PUBLICATIONS

Spinke et al., Molecular recognition at self assembled monolayers: optimization of surface functionalization. J Chem Phys. Nov. 1993;99(9):7012-9.

Spinke et al., Molecular recognition at self assembled monolayers: the construction of multicomponent multilayers. Langmuir. 1993;:1821-5.

Sprinzl et al., "Enzymatic Incorporation of ATP and CTP Analogues into the 3' End of tRNA," Eur. J. Biochem. 81:579-589 (1977).

Steurer et al., Bromide-Mediated ortho-Deprotonation in the Synthesis of Chiral, Nonracemic Ferrocene Derivatives. Organometallics. Jun. 19, 2007; 26(15):3850-9.

Stodt et al., "Preparation, Reactivity and Peptide Labelling Properties of (.eta..sup.6-Arene)ruthenium(II) Complexes with Pendant Carboxylate Groups," Euro. J. Inorg. Chem. 1873-1882 (2003).

Sutton et al., "Determination of the Comporportionation Constant for a Weakly Coupled Mixed-Valence System by Titration of the Intervalence Treansfer Band: .mu.-4,4'-Bipyridyl)-bis(pentaammineruthenium)(5+)," Inorg. Chem. 18(4):1017-1021 (1979).

Sutton et al., Metal to Metal Interactions in Weakly Coupled Mixed-Valence Complexes Based on Ruthenium Ammines, Inorg. Chem. 20(10):3125-3134 (1981).

Syamal et al., "Syntheses and characterization of a chelatingresin containing ONNO donor quadridentate Schiff base and its coordination complexes with copper(II), nickel(II), cobalt(II), iron(III), zinc(II), cadmium(II), molybdenum(VI) anduranium(VI)" Reactive and Functional Polymers 39:27-35 (1999).

Tabata et al., Use of a biosensor consisting of an immobilized NADH oxidase column and a hydrogen peroxide electrode for the determination of serum lactate dehydrogenase activity. Analy. Chim. Acta. Nov. 20, 1994; 298(1):113-119.

Therrien et al., "New mono and dinuclear arene ruthenium chloro complexes containing ester substituents," Inorganica Chimica Acta 359:4350-4354 (2006).

Tlais et al., New Strategies for Protecting Group Chemistry: Synthesis, Reactivity, and Indirect Oxidative Cleavage of para-Siletanylbenzyl Ethers. Journal of Organic Chemistry. Jan. 30, 2009; 74(5):1876-85. (Abstract Only).

Tom et al., Mixed Valence Complexes of Ruthenium Ammines with 4,4'-Bipyridine as Bridging Ligand, J. Am. Chem. Soc. 96(25):7827-7829 (1974).

Umapathy et al., Raman spectroscopic studies of substituted bipyridines, their Ruthenium(II) complexes and surface-derivatized $TiO_2$. J Mole Struct. 1989;194:107-16.

Volkers et al., "Coordination Chemistry of 3-Mercapto-2-(Mercaptomethyl)propanoic Acid (Dihydroasparagusic Acid) with Iron and Nickel," Eur. J. Inorg. Chem. 4793-4799 (2006).

Von Kiedrowski et al., Parabolic Growth of a Self-Replicating Hexadeoxynucleotide Bearing a 3'-5' Phosphoamidate Linkage. Angew. Chem. Int. Ed. Engl. 1991. 30: 423-426. (Abstract Only).

Vukmirovic-Popovic et al., Presence and enzymatic activity of prostate-specific antigen in archival prostate cancer samples. Oncol Rep. Oct. 2008;20(4):897-903.

Wang et al., "tmtacn,tacn, and Triammine Complexes of (.eta..sup.6-arene)Ox.sup.II: Syntheses, Characterizations, and Photosubstitution Reactions (tmtacn=1,4,7-Trimethyl-1,4,7- triazacyclononane; tacn=1,4,7-Triazacyclononane)," Inorg. Chem.40:593-600 (2001).

Wang et al., A sensitive ligase-based ATP electrochemical assay using molecular beacon-like DNA. Biosens Bioelectron. May 15, 2010;25(9):2101-6.

Ward, Structural and photophysical properties of luminescent cyanometallates. [M(diimine)(CN)4]2 and their supramolecualr assemblies. Dalton Trans. 2010;39:8851-67.

Wei et al., "Diverse Redox-Active Molecules Bearing Identical Thiol-Terminated ripodal Tethers for Studies of Molecular Information Storage," J. Org. Chem. 69:1461-1469 (2004). (Abstract Only).

Wictome et al., Development of an in vitro bioassay for Clostridium botulinum type B neurotoxin in foods that is more sensitive than the mouse bioassay. Appl Environ Microbiol. Sep. 1999;65(9):3787-92.

Xiang et al., Using personal glucose meters and functional DNA sensors to quantify a variety of analytical targets. Nat Chem. Jul. 24, 2011;3(9):697-703.

Zhou et al., An amperometric immunosensor based on an electrochemically pretreated carbon-paraffin electrode for complement III (C3) assay. Biosensors and Bioelectronics. 2008;18:473-81.

[No Author Listed] Comprehensive Coordination Chemistry, Ed. Wilkinson et al., Pergamon Press, 1987, Chaps. 13.2:73-98; 21.1:813-898; 21.3:915-957.

\* cited by examiner

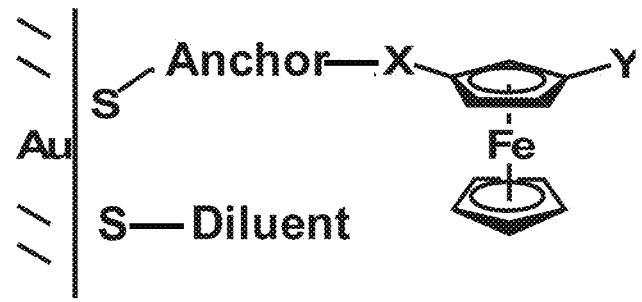
Where X=Spacer
Y= Functional Group
S= One or multiple sulphur bonds
Diluent is optional
FIGURE 1A
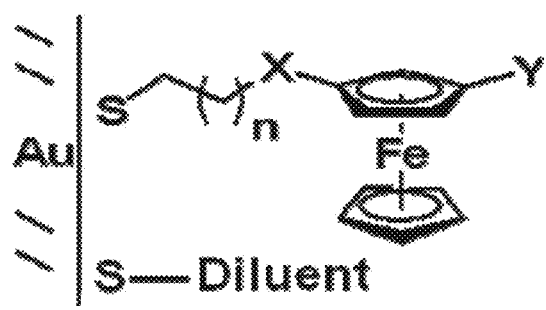
Where X=Spacer
Y= Functional Group
S= One or multiple sulphur bonds
Diluent is optional
FIGURE 1B
FIGURE 1

Capture ligands
Carboxylic acid reactant capture ligand
1. Anthrax peptide: FMOC-NH-ATYPLPIR-COOH (SEQ NH2 Reactive Maleimide NH2 Reactive Maleimide COOH Reactive Maleimides C2-Mal COOH Reactive Maleimides C6-Mal M = Transitional Metal, R = H or Substituents, and n = 1 to 10.

where "anchor" = oligomethylene, oligophenylene(ethynylene), oligophenylene, polyethyleneglycol

CHEMISTRY USED IN BIOSENSORS

RELATED APPLICATIONS

This application claims the benefit of priority under 35 U.S.C. §119(e) to U.S. provisional application 61/555,945, filed Nov. 4, 2011, entitled "Novel Chemistry Used in Biosensors", the contents of which are incorporated by reference herein in their entirety.

FIELD OF THE INVENTION

The invention relates to novel compositions and methods for the detection of analytes using change in $E^0$ of target analytes, or resulting in quantifiable electrochemical signal at two unique potentials, $E^o{}_1$ and $E^o{}_2$.

BACKGROUND OF THE INVENTION

Electron transfer reactions are crucial steps in a wide variety of biological transformations ranging from photosynthesis or aerobic respiration. Studies of electron transfer reactions in both chemical and biological systems have led to the development of a large body of knowledge and a strong theoretical base, which describes the rate of electron transfer in terms of a small number of parameters.

Electronic tunneling in proteins and other biological molecules occurs in reactions where the electronic interaction of the redox centers is relatively weak. Semiclassical theory reaction predicts that the reaction rate for electron transfer depends on the driving force ($-\Delta G°$), a nuclear reorganization parameter ($\lambda$), and the electronic-coupling strength between the reactants and products at the transition state ($H_{AB}$), according to the following equation:

$$k_{ET} = (4\pi^3/h^2 \lambda k_B T)^{1/2} (H_{AB})^2 \exp[(-\Delta G° + \lambda)2/\lambda k_B T]$$

The nuclear reorganization energy, $\lambda$, in the equation above is defined as the energy of the reactants at the equilibrium nuclear configuration of the products. For electron transfer reactions in polar solvents, the dominant contribution to $\lambda$ arises from the reorientation of solvent molecules in response to the change in charge distribution of the reactants. The second component of $\lambda$ comes from the changes in bond lengths and angles due to changes in the oxidation state of the donors and acceptors.

Previous work describes using change in reorganization energy, $\lambda$, as the basis of novel sensors. See for example, U.S. Pat. Nos. 6,013,459, 6,013,170, 6,248,229, and 7,267,939, all herein incorporated by reference in their entirety. The methods generally comprise binding an analyte to or near a redox active complex. The redox active complex comprises at least one electroactive molecule and a capture ligand which will bind the target analyte, and the complex is bound to an electrode. Upon analyte binding, the reorganization energy of the redox active molecule is altered, thus changing the $E^0$, and allowing detection.

It is an object of the present invention to provide composition and methods for the detection of target analytes using alterations in the solvent reorganization energy, such as utilizing cyano ligands with the transition metals of the biosensor, corresponding to changes in the $E^0$ of redox active molecules.

The electromotive force (EMF) is the maximum potential difference between two electrodes of a galvanic or voltaic cell, where the standard hydrogen electrode is on the left-hand side for the following cell:

| 1 | | | | 2 |
|---|---|---|---|---|
| Pt Electrode | $H_2$ | Aqueous Electrolyte Solution | $10^{-3}$ M Fe(ClO$_4$)$_3$ $10^{-3}$ M Fe(ClO$_4$)$_2$ | Pt |

The EMF is called the electrode potential of the electrode placed on the right-hand side in the graphical scheme of the cell, but only when the liquid junction between the solutions can be neglected or calculated, or if it does not exist at all.

The electrode potential of the electrode on the right-hand side (often called the oxidation-reduction potential) is given by the Nernst equation $$E_{Fe^{3+}/Fe^{2+}} = E_{Fe^{3+}/Fe^{2+}}^0 + (RT/F)\ln(a_{Fe^{3+}}/a_{Fe^{2+}})$$

This relationship follows from equation (2.21) when ($\mu_{Fe^{3+}}^0 + \mu_{Fe^{2+}}^0$)/F is set equal to $E_{Fe^{3+}/Fe^{2+}}^0$ and the pH and $\ln p_{H_2}$ are equal to zero. In the subscript of the symbol for the electrode potential the symbols for the oxidized and reduced components of the oxidation-reduction system are indicated. With more complex reactions it is particularly recommended to write the whole reaction that takes place in the right-hand half of the cell after symbol E (the 'half-cell' reaction); thus, in the present case $$E_{Fe^{3+}/Fe^{2+}} \equiv E(Fe^{3+} + e = Fe^{2+})$$

Quantity $E_{Fe^{3+}/Fe^{2+}}^0$ is termed the standard electrode potential. It characterizes the oxidizing or reducing ability of the component of oxidation-reduction systems. With more positive standard electrode potentials, the oxidized form of the system is a stronger oxidant and the reduced form is a weaker reductant. Similarly, with a more negative standard potential, the reduced component of the oxidation-reduction system is a stronger reductant and the oxidized form a weaker oxidant.

The standard electrode $E^0$, in its standard usage in the Nernst equation, equation (1-2) is described as:

$$E = E^0 + \frac{2.3RT}{nF} \log \frac{C_0(0, t)}{C_R(0, t)}$$

Where $E^0$ is the standard potential for the redox reaction, R is the universal gas constant (8.314 JK$^{-1}$mol$^{-1}$), T is the Kelvin temperature, n is the number of electrons transferred in the reaction, and F is the Faraday constant (96,487 coulombs). On the negative side of $E^0$, the oxidized form thus tends to be reduced, and the forward reaction (i.e., reduction) is more favorable. The current resulting from a change in oxidation state of the electroactive species is termed the faradaic.

Previous work describes using conversion of functional groups attached to a transitional metal complex resulting in quantifiable electrochemical signal at two unique potentials, $E^o{}_1$ and $E^o{}_2$. See for example, U.S. Patent Publication Nos: US 2011 0033869 and US 2012-0181186, all herein incorporated by reference in their entirety. The methods generally comprise binding an analyte within a sandwich of binding ligands, which may have a functional tag, on a solid support other than the electrode. After target binding, a peroxide generating moiety or an intermediary enzyme and substrate are added, which generates hydrogen peroxide. The redox active complex is bound to an electrode and comprises a peroxide sensitive moiety (PSM). The peroxide generated from the enzyme system reacts with the PSM, removing a self-immolative moiety (SIM) and converting functional groups attached to a transitional metal complex resulting in quantifiable electrochemical signal at two unique potentials, $E^o{}_1$ and $E^o{}_2$.

While the forementioned methods for detection of target analytes using alterations in the solvent reorganization energy corresponding to changes in the E° of redox active molecules or by measuring quantifiable electrochemical signals at two unique potentials $E°_1$ and $E°_2$ are useful for their intended purposes, improved robust redox active complexes that provide greater signal amplification, particularly where low concentrations of target analytes are involved, are desired.

SUMMARY OF THE INVENTION

The present invention provides methods and compositions relating to biosensors for use in the detection of target analytes.

In one aspect, the invention provides compositions comprising a solid support (sometimes referred to herein as a "substrate") comprising an electrode comprising a covalently attached electroactive complex (EAM) with a particular E°. The substrates can optionally comprise an array of electrodes. The electrode(s) each comprise an EAM, which optionally can be part of a redox active capture complex (ReAMC). Suitable transition metals include iron, ruthenium and osmium, as well as others outlined herein. In some embodiments, the EAMs comprise at least one cyano ligand, with 2, 3, 4 and 5 also finding use in the invention. The EAMs (as well as the ReAMCs and diluent SAM forming species) can be linked to the electrodes using attachment linkers, including alkyl groups (including substituted alkyl groups).

In a further aspect, the electrodes optionally comprise self assembled monolayer (SAM) species.

In an additional aspect, the EAM/ReAMCs of the invention are attached to the electrode using an anchor ligand, which can be "unipodal" or "multipodal", for example including the use of bipodal attachments such as two sulfur atoms or cyclic disulfide anchor groups.

In a further aspect, the EAM is part of a redox active capture complex (ReAMC) comprising said EAM and a capture ligand. In one aspect, the capture ligand provides a coordination atom for the transition metal. In additional aspects, the capture ligand is separate from the EAM, such that the electrode comprises a first species comprising the EAM and a second species comprising a capture ligand.

In one aspect, the capture ligand is a protein, including peptides, or a carbohydrate.

In an additional aspect, the invention provides methods of detecting a target analytes comprising contacting a sample with a composition comprising an electrode as outlined herein. The binding of the target analyte to the capture ligand alters the E° of the EAM, e.g. creating a second E°, which is measured to determine the presence or absence of the target analyte.

In a further aspect, the invention provides methods of making a biosensor comprising providing an electrode comprising a first species (usually a SAM forming species) comprising a first functional group. The electrode is contacted with a biomolecule (which will become the capture ligand) comprising a second functional group to form a covalent bond between the first species and the biomolecule. The electrode also comprises an electroactive complex (EAM), to form the biochips of the invention. In some aspects the functional groups on each molecule are selected from the group consisting of moieties comprising a maleimide, imidoester, N-hydroxysuccinimidyl, alkyl halide, aryl halide, alpha-haloacyl and pryidyl disulfide and cysteines (e.g. the first functional group comprises a maleimide and the biomolecule is a protein (e.g. peptide) comprising a cysteine amino acid.

In an additional aspect, the invention comprises compounds having the formula:

Anchor-Spacer 1-EAM-(Spacer 2)$_n$-CL wherein said anchor comprises a cyclic-disulfide group,
EAM is an electroactive moiety comprises a solvent accessible redox compound,
CL is a capture ligand,
Spacer 1 is a SAM forming species,
Spacer 2 is a linker, and
n=0 or 1.

In an additional aspect, the invention comprises compounds having the formula:

Anchor-Spacer 1-EAM-(Spacer 2)$_n$-CL          (I), wherein EAM is an electroactive moiety comprising a transition metal and at least one charge-neutralizing ligand. The charge neutralizing ligand can be selected from the group consisting of: dithiocarbamate, benzenedithiolate, a Schiff base, EDTA, DTPA, carboxylate, amine, thiolate, phosphine, imidazole, pyridine, bipyridine, terpyridine, tacn, salen, acacen, Cp, pincer, scorpionates and pentaammine.

In another aspect the invention provides a composition (EAM) that is part of a first solid support comprising an electrode comprising: a self-assembled monolayer (SAM). (ii) a covalently attached electroactive active moiety (EAM) comprising a transition metal complex comprising a self-immolative moiety (SIM) and a peroxide sensitive moiety (PSM), wherein said EAM has a first E° and a self-assembled monolayer (SAM). The capture binding ligand that binds the analyte, is on a second solid support other than the electrode. After target binding, a peroxide generating moiety or an intermediary enzyme and substrate are added which generates hydrogen peroxide. The redox active complex is bound to an electrode and comprises a peroxide sensitive moiety (PSM). The peroxide generated from the enzyme system reacts with the PSM, removing a self-immolative moiety (SIM) and converting functional groups attached to a transitional metal complex resulting in quantifiable electrochemical signal at two unique potentials, $E°_1$ and $E°_2$.

In one embodiment the reaction mechanism for representative ferrocene-based EAMs that undergo a peroxide-triggered change in apparent formal potential (E-TRACE) follow the following steps:
a) starting ferrocenyl EAM that contains an electron-withdrawing carbamate-linked boronate ester-substituted ligand; and
b) reaction with peroxide leads to an electron-donating amino ligand on the ferrocene which results in a distinct the redox potential from starting species.

In another aspect, the invention provides compositions comprising an electrode comprising a covalently attached electroactive complex (EAM), said EAM comprising a 1,3-disubstituted ferrocene.

In one embodiment of the invention, the electrode is gold.
In another embodiment of the invention, the EAM is covalently attached to said electrode via a sulfur atom or two sulfur atoms.
In another embodiment of the invention, the EAM is attached to said electrode using an attachment linker with a first terminus comprising said sulfur atom(s).
In another embodiment of the invention, the attachment linker comprises a second terminus for attachment to the EAM.
In another embodiment of the invention, the attachment linker is an alkyl chain.

In another embodiment of the invention, the alkyl chain is substituted.

In another embodiment of the invention, the electrode comprises a redox active capture complex (REAMC) comprising the EAM and a capture ligand.

In another embodiment of the invention, the EAM is functionalized with said capture ligand.

In another embodiment of the invention, the electrode is gold and said REAMC is covalently attached to said electrode via a sulfur atom or two sulfur atoms.

In another embodiment of the invention, the REAMC is attached to said electrode using an attachment linker with a first terminus comprising said sulfur atom(s).

In another embodiment of the invention, the attachment linker comprises a second terminus for attachment to the EAM.

In another embodiment of the invention, the attachment linker is an alkyl chain.

In another embodiment of the invention, the alkyl chain is substituted.

In another embodiment of the invention, the electrode comprises a first species comprising said EAM and a second species comprising a capture ligand.

In another embodiment of the invention, the capture ligand is a peptide, an enzyme, an enzyme substrate or a carbohydrate.

In another embodiment of the invention, the composition comprises an array of electrodes, each comprising a covalently attached transition metal complex comprising a transition metal and at least one cyano ligand.

In another aspect, the invention provides methods of detecting a target enzyme comprising:
a) contacting a sample with a composition comprising an electrode comprising:
  i) an electroactive moiety (EAM) comprising a 1,3-disubstituted ferrocene with a first $E^0$;
  ii) a capture ligand;
under conditions whereby said target enzyme, if present, alters said capture ligand such that said EAM has a second $E^0$; and
b) measuring said second $E^0$.

In one embodiment of the invention, the composition comprises a support comprising a plurality of electrodes each comprising:
i) an electroactive moiety (EAM) comprising a 1,3-disubstituted ferrocene with a first $E^0$;
ii) a capture ligand.

In another aspect, the invention provides methods of detecting a target enzyme comprising:
a) contacting a sample with a composition comprising a REAMC comprising:
  i) an electroactive moiety (EAM) comprising a 1,3-disubstituted ferrocene with a first $E^0$;
  ii) a capture ligand;
under conditions whereby said target enzyme, if present, alters said capture ligand such that said EAM has a second $E^0$; and
b) measuring said second $E^0$.

In another aspect, the invention provides compositions comprising an electrode comprising:
a) a first species comprising a functional group; and
b) an electroactive complex (EAM), said EAM comprising a 1,3-disubstituted ferrocene.

In one embodiment of the invention, the functional group is a maleimide group.

In another aspect, the invention provides methods of making a biosensor comprising:

a) providing an electrode comprising:
  i) a first species comprising a first functional group; and
  ii) an electroactive complex (EAM), said EAM comprising a 1,3-disubstituted ferrocene;
c) contacting said electrode with a biomolecule comprising a second functional group to form a covalent bond between said first species and said biomolecule.

In one embodiment of the invention, the first functional group is selected from the group consisting of moieties comprising a maleimide, imidoester, N-hydroxysuccinimidyl, alkyl halide, aryl halide, alpha-haloacyl and pryidyl disulfide.

In one embodiment of the invention, the first functional group comprises a maleimide and said biomolecule is a protein comprising a cysteine amino acid.

In one embodiment of the invention, the protein is a peptide.

In another aspect, the invention provides compounds having the formula:

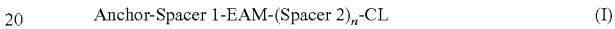

Anchor-Spacer 1-EAM-(Spacer 2)$_n$-CL      (I)

wherein said anchor comprises a cyclic-disulfide group,
EAM is a 1,3-disubstituted ferrocene,
CL is a capture ligand,
Spacer 1 is a SAM forming species,
Spacer 2 is a linker, and
n=0 or 1.

In another aspect, the invention provides compositions comprising an electrode comprising a self-assembled monolayer (SAM), wherein said SAM comprises a compound having the formula:

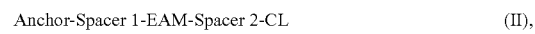

Anchor-Spacer 1-EAM-Spacer 2-CL      (II), wherein said anchor is linked to said electrode group through a disulfide group,
EAM is a 1,3-disubstituted ferrocene,
CL is a capture ligand,
Spacer 1 is either insulating or conducting, and
Spacer 2 is an optional linker.

In another aspect, the invention provides methods comprising:
a) providing a compound having the formula:

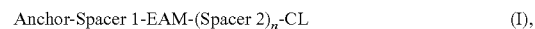

Anchor-Spacer 1-EAM-(Spacer 2)$_n$-CL      (I), wherein said anchor comprises a cyclic-disulfide group,
EAM is a 1,3-disubstituted ferrocene,
CL is a capture ligand,
Spacer 1 is either insulating or conduction,
Spacer 2 is a linker, and
n=0 or 1; and
b) contacting said compound to an electrode by opening said cyclic disulfide to form an attachment of said anchor to said electrode.

In one embodiment of the invention, the electrode further comprises a self-assembled monolayer (SAM).

In another aspect, the invention provides methods of detecting a target analyte in a test sample, comprising:
a) providing an electrode comprises a compound having the formula:

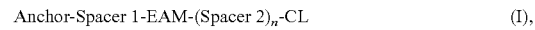

Anchor-Spacer 1-EAM-(Spacer 2)$_n$-CL      (I), wherein said anchor comprises a cyclic-disulfide group,
EAM is 1,3-disubstituted ferrocene,
CL is a capture ligand,
Spacer 1 is either insulating or conduction,
Spacer 2 is a linker, and
n=0 or 1; and b) contacting said electrode with said test sample; and
c) determining the presence of said target analyte by measuring the reorganization energy of said EAM.

In another aspect, the invention provides compositions comprising an electrode comprising:
(i) an optional self-assembled monolayer (SAM); and
(ii) an electroactive active moiety (EAM), said EAM comprising a 1,3-disubstituted ferrocene.

In one embodiment, the invention provides the composition wherein said 1,3-disubstituted ferrocene comprises any ferrocene compound disclosed herein.

In one embodiment, the invention provides the composition wherein said 1,3-disubstituted ferrocene further comprises a functional group.

In another embodiment, the invention provides the composition wherein the functional group comprises a self-immolative moiety and a peroxide sensitive moiety.

In one embodiment, the invention provides the composition wherein said electrode further comprises a functional group.

In another embodiment, the invention provides the composition wherein said functional group comprises a capture ligand. In yet another embodiment, said functional group is selected from the group consisting of moieties comprising a maleimide, an imidoester, N-hydroxysuccinimidyl, alkyl halide, aryl halide, alpha-haloacyl and pyridyl disulfide.

In one embodiment, the invention provides the composition further comprising a self-assembled monolayer (SAM). In another embodiment, the SAM is a non-conductive oligomer or a conductive oligomer.

In another aspect, the invention provides methods for detecting one or more target analytes in a test sample, said method comprising:
(a) contacting the test sample with a capture binding ligand under conditions such that the capture binding ligand specifically binds to a target analyst, if present, in said test sample to form a first complex, the capture binding ligand bound to a first solid support;
(b) contacting said first complex, if present, to a soluble capture ligand to form a second complex, wherein said soluble capture ligand comprises a peroxide-generating system;
(c) contacting said second complex with a substrate for said peroxide-generating system under conditions wherein a peroxide is generated to form an assay mixture;
(d) contacting the assay mixture with a second solid support comprising an electrode comprising (i) a self-assembled monolayer (SAM) of an electroactive active moiety (EAM), or (ii) an EAM and optional SAM, wherein said EAM comprises a 1,3-disubstituted ferrocene, a self-immolative moiety, and a peroxide sensitive moiety (PSM) and has a first $E^o$, and wherein said peroxide reacts with said PSM to release said SIM from said EAM and result in said EAM having a second $E^o$; and having a second $E^o$;
(f) measuring the electrochemical properties of said EAM at the first $E^o$ and at the second $E^o$; and
(g) detecting said target analyte from said electrochemical properties.

In another aspect, the invention provides methods for detecting one or more target analytes in a test sample, said method comprising:
(a) contacting the test sample with a soluble capture ligand to form a first complex, wherein said soluble capture ligand comprises a peroxide-generating system;
(b) contacting said first complex, if present, with capture binding ligand under conditions such that the capture binding ligand specifically binds to a target analyst to form a second complex, the capture binding ligand bound to a first solid support;
(c) contacting said second complex with a substrate for said peroxide-generating system under conditions wherein a peroxide is generated to form an assay mixture;
(d) contacting the assay mixture with a second solid support comprising an electrode comprising (i) a self-assembled monolayer (SAM) of an electroactive active moiety (EAM) or (ii) an EAM and optional SAM, wherein said EAM comprises a 1,3-disubstituted ferrocene, a self-immolative moiety, and a peroxide sensitive moiety (PSM) and has a first $E^o$, and wherein said peroxide reacts with said PSM to release said SIM from said EAM and result in said EAM having a second $E^o$; and having a second $E^o$;
(f) measuring the electrochemical properties of said EAM at the first $E^o$ and at the second $E^o$; and
(g) detecting said target analyte from said electrochemical properties.

In one embodiment, the methods as described above are wherein prior to step (c), further comprising isolating second complex.

In another embodiment, the methods as described above are wherein 1,3-disubstituted ferrocene is any ferrocene compound disclosed herein.

In another aspect, the invention provides ferrocene compounds of formula (III):

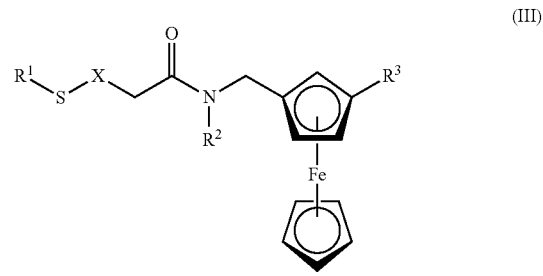

(III)

wherein
$R^1$ is hydrogen, —S—$C_1$-$C_{20}$ alkyl, —S—$C_2$-$C_{20}$ alkenyl, or —S—$C_2$-$C_{20}$ alkynyl,
X is —$C_1$-$C_{20}$ alkyl-, —$C_2$-$C_{20}$ alkenyl-, —$C_2$-$C_{20}$ alkynyl-, —$X^1$—CONH—, —$X^1$—CO$_2$—, or —$X^1$—OCNH—, where $X^1$ is selected from the group consisting of polyoxyalkylene, of polymethylene, oligophenylene, and polyphenylene(ethynylene);
$R^2$ is hydrogen or $C_1$-$C_6$ alkyl; and
$R^3$ is —NR$^4$R$^5$, —CO$_2$R$^5$, —CONR$^4$R$^5$, or —NR$^5$CO$_2$—R$^6$;
where $R^4$ is hydrogen, or $C_1$-$C_6$ alkyl;
where $R^5$ is hydrogen, $C_1$-$C_6$ alkyl, $C_2$-$C_6$ alkenyl, $C_2$-$C_6$ alkynyl, aryl($C_1$-$C_6$ alkyl), aryl($C_2$-$C_6$ alkenyl), heteroaryl ($C_1$-$C_6$ alkyl), or heteroaryl($C_2$-$C_6$ alkenyl), where each optionally substituted with one to four substituents selected from halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —CO$_2$H, —COH, —CO$_2$($C_1$-$C_6$ alkyl), —CONH$_2$, —CON($C_1$-$C_6$ alkyl)$_2$, or peroxide sensitive moiety; and
where $R^6$ is $C_1$-$C_6$ alkyl, $C_2$-$C_6$ alkenyl, $C_2$-$C_6$ alkynyl, aryl ($C_1$-$C_6$ alkyl), aryl($C_2$-$C_6$ alkenyl), heteroaryl($C_1$-$C_6$ alkyl), or heteroaryl($C_2$-$C_6$ alkenyl), where each optionally substituted with one to four substituents selected from halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —$CO_2H$, —COH, —$CO_2(C_1$-$C_6$ alkyl), —$CONH_2$, —$CON(C_1$-$C_6$ alkyl)$_2$, or peroxide sensitive moiety.

These and other aspects of the invention will be apparent in light of the description below.

BRIEF DESCRIPTION OF THE DRAWINGS

FIG. 1A shows the general schematic of a 1,3-disubstituted ferrocene SAM using a generic schematic. FIG. 1B shows the general schematic of a 1,3-disubstituted ferrocene SAM with an alkyl thiol anchor.

FIG. 3 depicts some of the building blocks and examples of functional groups Y being capture ligands for generating the compound for detection of analyte. FIG. 3B depicts exemplary capture ligands, including analyte specific peptides, as the functional groups.

FIG. 5A depicts the situation where a linker is attached at one end to the electrode and the other end terminates in a ligand (L) that provides a coordination atom for the transition metal (TM). The capture substrate (CS) provides an additional ligand (not depicted), and a plurality of other ligands provide the remaining coordination atoms. Upon action by the enzyme, the capture substrate results in a leaving group (X). It should be noted that these Figures depicts a situation where the transition metal utilizes 6 coordination atoms (FIG. 5A), but other numbers of coordination atoms can be used, depending on the metal. Similarly, these Figures depicts the use of ligands that provide a single coordination atom, but fewer ligands providing multiple coordination atoms (e.g. multidentate) ligands can be used as well (FIG. 5B). FIG. 5 also depicts the situation where the capture substrate and the EAM are attached separately to the electrode. FIG. 5 also depicts a similar situation except the capture substrate does not provide a coordination atom to the transition metal. It should be appreciated that solution phase systems can be similar to FIG. 5 in that the electrochemical potential of the EAM in solution can be altered as a result of the enzymatic activity of the target enzyme.

FIG. 19 depicts exemplary electrochemical response for comparison between typical 1,1'-Fc and 1,3-Fc compounds.

FIG. 20 depicts exemplary electrochemical response for comparison between typical 1,1'-Fc and 1,3-Fc compounds following multiple scanning of the initial compound in the SAM, prior to reaction with peroxide.

Figure 21A:
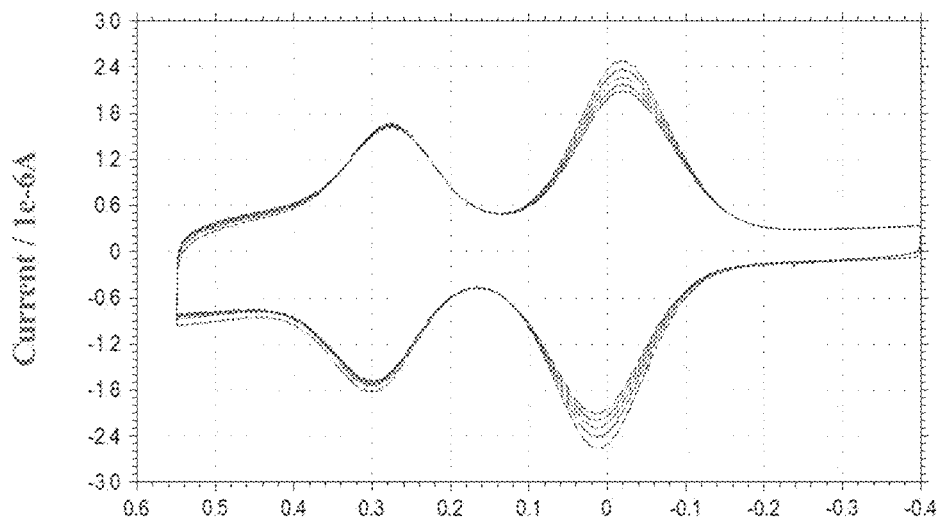
Figure 21B:
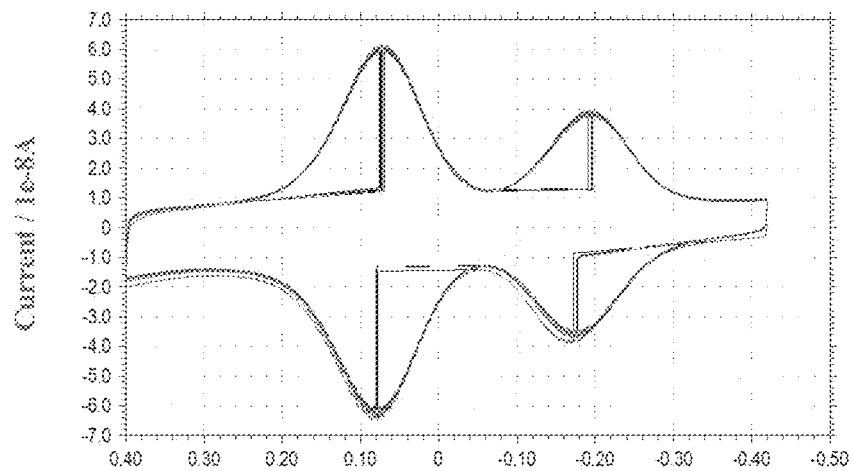

FIG. 21 depicts exemplary electrochemical response for comparison between typical 1,1'-Fc and 1,3-Fc compounds following multiple scanning of the final compounds in the SAM, after reaction with peroxide. FIG. 21A shows a cyclic voltammogram for a Fc 1-1' scanned multiple times (20 times) and it is shown that the peak current decreases continuously suggesting that the reacted 1-1'-Fc compound within the monolayer is not stable. FIG. 21B shows a cyclic voltammogram for a 1,3-Fc scanned multiple times (20 times) and it is shown that the peak current is stable suggesting that the 1,3-Fc reacted compounds within the monolayer are very stable.

DETAILED DESCRIPTION OF THE INVENTION

The present invention is directed to improvements in electrochemical biosensors that rely on changes in the reorganization energy, $\lambda$, upon interaction of the target analyte and the biosensor, as evidenced by alterations in the observed $E^0$. As shown previously, biosensors have been described that rely on changes in reorganization energy. The present invention has shown surprising improvements such as utilizing cyano ligands for the transition metal of the electroactive moieties (EAMs). The cyano ligands provide a surprising increase in the change of the $E^0$; e.g., the delta in the $E^0$ is higher than seen for other charged ligands.

I. Overview of Reorganization Energy

The present invention provides methods and compositions for the detection of target analytes using changes in the reorganization energy of redox active molecules upon binding of the analytes, to facilitate or hinder electron transfer between the redox active molecule and an electrode. This invention is based on the fact that when a redox active molecule, such as a transition metal ion, is either oxidized (losing an electron) or reduced (gaining an electron), changes occur in the molecular structure as well as in its immediate solvent environment. These changes in the molecules structure (bond lengths and angles) and in the organization of the solvent molecules surrounding the molecule serve to stabilize the new oxidation state energetically. The sum of these changes constitute the reorganization energy, $\lambda$, of a redox reaction. The intramolecular changes are termed the inner-sphere reorganization energy, $\lambda_i$, and the changes in the solvent and environment are termed the outer-sphere or solvent reorganization energy, $\lambda_o$.

For the purposes of this invention, the primary focus is on changes in the solvent reorganization energy although changes in the inner-sphere reorganization will also be considered in several embodiments of the invention. It is the intent of this invention to capitalize on changes in reorganization energy of a redox reaction when an electroactive molecule (EAM) is attached to a capture ligand (CL) which can selectively bind to an analyte of interest (e.g., protein or bacteria). Binding of the EAM-CL to the analyte results in a change in the solvent environment of the EAM so that the reorganization energy for a redox reaction involving the EAM is changed. For the case where the redox reaction involves electron transfer between an electrode and the EAM, the standard potential, $E^0$, is changed. Thus, a change in $E^0$ for an EAM-CL complex is an indication that it is bound to the analyte. It is the intent of this invention to detect the change in $E^0$ as an indicator of binding and, consequently, the presence or absence of the analyte.

In conventional methodologies for analyte detection using electron transfer usually employ the EAM as a label or tag attached to one member of a binding pair (e.g., antibody and antigen). In these methods, EAM's are chosen in which the outer sphere solvent effect is minimal, by using electroactive molecules that have minimal solvent reorganization upon oxidation or reduction. Such EAMs generally comprise large hydrophobic ligands which have little interaction with water. Thus, the ligands for the transition metal ions traditionally used are non-polar and are generally hydrophobic, frequently containing organic rings (e.g., bipyridyl and terpyridyl). Such EAMs are chosen because conventionally because the magnitude of the total electron transfer reaction is measured (current) at a predetermined electrode potential.

Without being bound by theory, it is expected that the redox molecules best suited for this invention will be those whose redox reaction has a large solvent reorganization energy in aqueous environments. Solvent reorganization to stabilize an increase or decrease in charge can be attributed to several phenomena. In polar solvents such as water, the charge on a redox molecule is stabilized by orientation of the polar solvent molecules in the environment near the redox molecule. Since polar molecules have slight charge variation on different atoms of the molecule, their orientation around the redox molecule can help to stabilize it. Further, some ligands, such as $CN^-$, themselves are polar and have partial charges on atoms. These polar ligands can themselves induce an orientation of surrounding solvent molecules. Stabilization (or destabilization) of charged redox molecules can also occur by hydrogen bonding of solvent and/or other molecules to the ligands of the transition metal in the redox molecule. Solvent molecules, as well as other molecules in the solvent surrounding a redox molecules can be characterized and compared based on their donor number or acceptor number (Neyhart et al., J. Am. Chem. Soc 118 (1996) 3724-29, incorporated herein by reference). The use of a particular solvent or a particular additive to a solvent of a molecule having a preferred donor or acceptor number would affect the solvent reorganization energy of a redox reaction. Further, a change in the charge of a redox molecule is stabilized by charged ion in the solvent. Thus, changes in solvent reorganization change upon analyte binding can be maximized by the proper choice of an electrolyte, considering the charge on the ions, the concentration of the ions, the size of the ions, and the hydrophobicity of the ions.

Without being bound by theory, it is preferred to maximize the stabilization of the redox molecule (i.e., maximize its solvent reorganization energy) in the solvent system of choice in order that the phenomena which stabilize the redox molecule are disrupted upon binding of the redox molecule/capture ligand complex, EAM-CL to the analyte. Under such conditions, one would expect that the change in reorganization energy, evidenced by a change in $E^0$, would be optimum. It is expected that the binding of the CL to the analyte will "force" the EAM into an environment on the surface or in a cleft or pocket of the analyte (e.g., a protein) which will be less favorable to the optimal organization of the solvent environment. In one embodiment it is expected that binding would cause a shedding of water molecules near the EAM because of steric constraints.

It should be noted, and not being bound by theory, that whether the solvent reorganization energy increases or decreases upon binding (and whether $E^0$ moves to more positive or to more negative potentials is dependent upon the particular charge of the EAM. If the EAM redox reaction being monitored results in an increased charge of the EAM, such as $EAM^{2+}$ oxidation to $EAM^{3+}$, then the bound environment of the EAM-CL would be less stabilized by reorganization than the unbound EAM-CL. Hence, one would expect the $E^0$ to move to more positive potentials. Alternatively, if the EAM redox reaction being monitored results in a decreased charge of the EAM, such as $EAM^{2-}$ oxidation to $EAM^-$, then the unbound EAM-CL would be less stabilized by reorganization than the bound EAM-CL. Hence, one would expect the $E^0$ to move to less positive potentials.

Without being bound by theory, there are two general mechanisms which may be exploited in the present invention. The first relates to inner sphere change due to the redox label. In this embodiment, the binding of a target analyte to a capture ligand which is sterically close to an EAM causes one or more of the small, polar ligands of the EAM to be replaced by one or more coordination atoms supplied by the target analyte, causing a change in the inner-sphere reorganization energy for at least two reasons. First, the exchange of a small, polar ligand for a putatively larger ligand will generally exclude more water from the metal, lowering the required solvent reorganization energy (i.e. an inner sphere $\lambda_i$ effect). Secondly, the proximity of a generally large target analyte to the relatively small redox active molecule will sterically exclude water within the first or second coordination sphere of the metal ion, also changing the solvent reorganization energy.

Alternatively, the invention relies on substitutionally inert ligand, plus outer sphere effects. In this embodiment exchange of the polar ligands on the metal ion by a target analyte coordination atom. Rather, in this embodiment, the polar ligands are effectively irreversibly bound to the metal ion, and the change in solvent reorganization energy is obtained as a result of the exclusion of water in the first or second coordination sphere of the metal ion as a result of the binding of the target analyte; essentially the water is excluded (i.e. an outer sphere $\lambda_o$ effect).

The present invention provides compounds with novel architecture and methods of using these compounds for detection of target analytes.

In some embodiments, the target analyte binds to the capture ligand. In some embodiments, the target analyte can be an enzyme, and the change in $E^0$ is as a result of an enzymatic event, as described in U.S. Patent Application No. 61/087, 094, hereby incorporated by reference in its entirety.

Overview of E-Trace Assay

In one particularly useful embodiment, an assay provided is based, in part, on the E-TRACE assay described in Ohmx's U.S. Patent Publication No. US 20120181186, filed Jan. 19, 2012 which claims the benefit of priority to U.S. provisional application Nos. 61/434,122, filed Jan. 19, 2011 and 61/523, 679, filed Aug. 15, 2011 and Ser. No. 12/853,204, filed Aug. 9, 2010, which claims the benefit of priority to U.S. provisional application Nos. 61/232,339, filed Aug. 7, 2009, and in U.S. patent application Ser. No. 13/653,931, filed Oct. 17, 2012, all which are incorporated by reference in their entirety. The E-TRACE assay is basically a sandwich assay on an electrochemical platform with an oxidase-tagged secondary antibody that produces peroxide as a surrogate target for electrochemical detection.

In one embodiment, a single measurement method for determining the proportion of target analyte in a sample can be performed according to the methods described herein by an electrochemical measurement using the enzyme-triggered redox altering chemical elimination (E-TRACE) reaction, or a standard immunoassay optical test detecting $H_2O_2$ in solution and is described in the following steps:

Step 1: Modification with Primary Antibody:

The surface of the electrochemical platform is modified to include the sensing molecule (EAM) for the E-TRACE detection of peroxide. Additionally a second solid support is modified with a capture probe. This capture probe, e.g. antibody, binds selectively and equivalently to all variant types of target (e.g., hemoglobin including hemoglobin and glycated hemoglobin). As defined herein, the terms "binds selectively" means binding to a predetermined target (e.g. total hemoglobin including hemoglobin A1c) and "binds equivalently" mean non-preferentially to both the protein (e.g., hemoglobin) and the glycated protein (e.g., hemoglobin A1c).

Step 2: Addition of Target:

This primary binding occurs and is assumed to saturate nearly all binding sites on the surface of the secondary support. The importance of this is that samples with different total target concentrations will still yield a representative proportion of the target analyte bound to the surface.

Step 3: Addition of Detection Antibody:

In certain embodiments, the secondary antibody is introduced to the surface and only binds to the immobilized target analyte. This means the ELISA-like sandwich complex only forms on sites occupied by the target analyte and not on sites occupied by non-target.

Step 4: Signal Transduction and Detection:

The anti-target antibody that selectively binds to target analyte is labeled with a peroxide-generating system, e.g., an oxidase enzyme (SOx). The oxidase label, oxidizes a substrate and produces hydrogen peroxide. The hydrogen peroxide generated reacts with the electrochemical surface of the solid state platform to provide an electrochemical signal.

The amount of signal is directly correlated to the number of sandwich complexes, which in turn is dependent on how much target analyte is immobilized on the surface. The signal observed provides an assessment of the ratio (percentage) of the target analyte in the sample.

II. Samples

The target analytes are generally present in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples, purified samples, raw samples, etc.; as will be appreciated by those in the art, virtually any experimental manipulation may have been done on the sample. Some embodiments utilize target samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

III. Solid Supports

The target analytes are detected using solid supports comprising electrodes. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety).

For the E-trace method, a binding ligand that binds non-preferentially to proteins and their glycated counterpart proteins may be optionally bound to a second solid support. Any suitable second solid support may be used, including without limitation, microparticles, magnetic microparticles, beads, and microchannels.

IV. Geometries of the Sensors

The present invention is directed to methods and compositions for detection of target analytes, based on a change of electrochemical potential, $E^0$, of a redox active molecule either on the surface of an electrode, or in some cases, in solution (while most of the description herein is directed to solid phase assays, as will be appreciated by those in the art, the invention can be used in solution as well, and such description herein is meant to apply as applicable to solution phase assays as well).

In general, the invention can be described as follows. A redox active molecule is attached to the surface of an electrode, generally through a linker as described herein. In addition, the electrode may also optionally comprise a self-assembled monolayer (SAM) as described herein. In the spatial vicinity of the redox active molecule, a capture ligand is also attached, generally in one of three ways, as described herein. Introduction and/or binding of the target analyte results in a change in the electrochemical potential of the redox active molecule, which is then detected in a variety of ways as described herein.

There are three basic geometries for the sensor, although the descriptions herein are not meant to be so limited. In one embodiment, an electroactive moiety (EAM), comprising a transition metal ion and ligands that provide coordination atoms for the transition metal (in some embodiments, at least one of which is a cyano ligand), is attached to an electrode. In addition, a capture ligand (sometimes also referred to as a "binding ligand") that will specifically bind the target analyte is also attached to the electrode. Both species are generally attached to the electrode using an attachment linker as described herein. The two species are attached to the electrode in such a manner that they are spatially close, such that the $E^0$ of the EAM is altered upon binding of a target analyte. It should be noted that a third species, comprising a monolayer forming species, described below, can also be optionally present on the electrode. In this embodiment, the EAM species can have the formula (Ia), the capture ligand species can have the formula (Ib) and the diluent species can have the formula (Ic):

$$\text{AG-Spacer 1-EAM} \qquad\qquad (Ia)$$

$$\text{AG-Spacer 1-CL} \qquad\qquad (Ib)$$

$$\text{AG-Spacer 1-TG}_n \qquad\qquad (Ic)$$

wherein AG is an anchor group, EAM is an electroactive moiety comprises a solvent accessible redox complex, spacer 1 is a SAM forming species described herein, CL is a capture ligand, and TG is a terminal group, with n being 0 or 1.

In a second embodiment, one of the coordination atoms for the transition metal of the EAM is provided by the capture ligand, forming a "redox active moiety complex", or ReAMC. In this embodiment, the coordination atom can be actually part of the capture ligand (e.g. if the capture ligand is a peptide, an amino group can provide the coordination atom) or part of a linker used to attach the capture ligand (e.g. a pyridine linker, etc.). The ReAMC is attached as a single species, and as above, an additional species, comprising a monolayer forming species, described below, can also be optionally present on the electrode. In this embodiment, the present invention provides a compound having the formula (II):

AG-Spacer 1-EAM-(Spacer 2)$_n$-CL    (II)

wherein AG is an anchor group, EAM is an electroactive moiety comprises a solvent accessible redox complex, CL is a capture ligand, spacer 1 is a SAM forming species described herein, and Spacer 2 is a linker, with n=0 or 1.

In a third embodiment, there ReAMC is a single species, but the capture ligand does not provide a coordination atom; rather, it is spatially close but distinct from the EAM of the ReAMC. Again, a third species, comprising a monolayer forming species, described below, can also be optionally present on the electrode. In this embodiment, the present invention provides a compound having the formula (III):

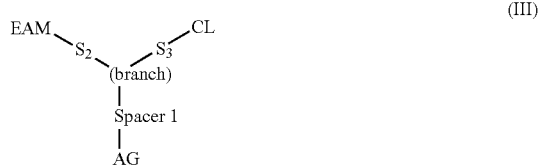

wherein AG is an anchor group, EAM is an electroactive moiety comprises a solvent accessible redox complex, CL is a capture ligand, spacer 1 is a SAM forming species described herein, and S$_2$ and S$_3$ are two linkages that link the EAM and CL together with the AG to form a branched structure. S$_2$ and S$_3$ can be different or the same.

One example of this configuration is shown below:

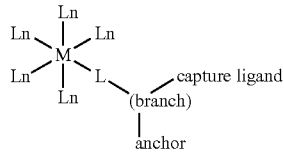

where M=transitional metal; Ln=coordinating ligand that covalently connected to the anchor and capture ligand, n=0 or 1; and L=coordinating ligand.

V. Electrode

In one aspect, the present invention provides these ligand architectures attached to an electrode. By "electrode" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo2O6), tungsten oxide (WO3) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary With the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the components of the system such as SAMs, EAMs and capture ligands bound to the inner surface. This allows a maximum of surface area containing the nucleic acids to be exposed to a small volume of sample.

The electrodes of the invention are generally incorporated into biochip cartridges and can take a wide variety of configurations, and can include working and reference electrodes, interconnects (including "through board" interconnects), and microfluidic components. See for example U.S. Pat. No. 7,312,087, incorporated herein by reference in its entirety.

The biochip cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

In a preferred embodiment, the biochips comprise substrates with a plurality of array locations. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, Teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc., polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety).

A. Self Assembled Monolayer Spacers

In some embodiments, the electrodes optionally further comprise a SAM. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target enzyme away from the electrode surface. In addition, a monolayer serves to keep charge carriers away from the surface of the electrode. Thus, this layer helps to prevent electrical contact between the electrodes and the ReAMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

In some embodiments, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electroactive polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

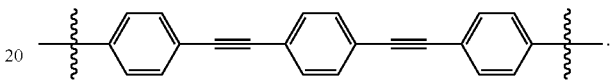

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in a preferred embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

In some embodiments, the electrode further comprises a passivation agent, preferably in the form of a monolayer on the electrode surface. For some analytes the efficiency of analyte binding (i.e. hybridization) may increase when the binding ligand is at a distance from the electrode. In addition, the presence of a monolayer can decrease non-specific binding to the surface (which can be further facilitated by the use of a terminal group, outlined herein. A passivation agent layer facilitates the maintenance of the binding ligand and/or analyte away from the electrode surface. In addition, a passivation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —$(CF_2)_n$—, —$(CHF)_n$— and —$(CFR)_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —$(CH_2)_{16}$ molecules, still may transfer electrons, albeit at a slow rate.

In some embodiments, the insulators have a conductivity, S, of about $10^{-7}$ $\Omega^{-1}$ cm$^{-1}$ or lower, with less than about $10^{-8}$ $\Omega^{-1}$ cm$^{-1}$ being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. Preferably, the alkyl or heteroalkyl chains are from about four to about 18 atoms in length, and more preferably from about six to about 16 atoms in length/

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types. Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold). Preferably, insulators are of the form —$(CH_2)_n$— having a thiol or disulfide terminus for attachment to gold. Also preferable, the alternate end of the insulator is terminated in a hydrophilic group such as oligoethylene glycol, —OH, or —COOH.

In some embodiments, the electrode is a metal surface and need not necessarily have interconnects or the ability to do electrochemistry.

B. Anchor Groups

The present invention provides compounds comprising an anchor group. By "anchor" or "anchor group" herein is meant a chemical group that attaches the compounds of the invention to an electrode.

As will be appreciated by those in the art, the composition of the anchor group will vary depending on the composition of the surface to which it is attached. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

Structure 1

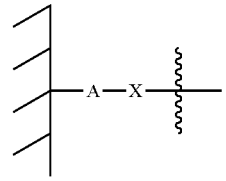

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via the nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode.

The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

1). Pyridinyl Anchor Groups

In one aspect, the present invention provides the use of pyridine and derivatives thereof to attach the compounds of the invention to the surface.

In some embodiments, the anchor comprises a pyridyl group, having the structure of formula (II):

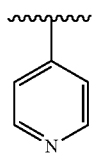

(II)

where the carbons on the ring can optionally and independently be substituted, using R groups as defined herein. Pyridine is a heterocyclic aromatic organic compound that is structurally related to benzene, wherein one CH group in the six-membered ring is replaced by a nitrogen atom. Pyridine can be used as a ligand in coordination chemistry. As a ligand, it is usually abbreviated as "py." The invention utilizes the ability of the lone electron pair on the nitrogen atom of the pyridine to bind to metal surfaces. One advantage of the pyridine based compounds is that they are air stable. Curtis et al., Inorg. Chem. 24:385-397 (1985); Callahan et al., Inorg. Chem. 14:1443-1453 (1975); Lavallee and Fleischer, J. Am. Chem. Soc. 94:2583-2599 (1972); and Jwo et al., J. Am. Chem. Soc. 101:6189-6197 (1979), all of which are incorporated by reference.

In some embodiments, the pyridyl group comprises a bipyridyl group (Bispyridylacetylene, BPA), comprising two pyridyl groups separated by an acetylene group, shown below:

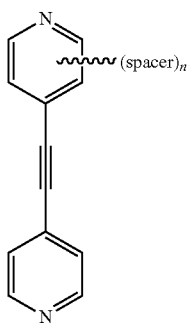

In this embodiment, the carbons on either ring can be optionally and independently be substituted, using R groups as defined herein. One of the rings will contain a linkage to a spacer, as defined herein, or, as shown in some of the figures, there may be more than one spacer attached to the pyridyl group (e.g. n=1 or more, with 2 finding particular use in some embodiments).

2). Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Thus, for example, when the electrode is a gold electrode, and "A" is a sulfur atom or moiety, such as generally depicted below in Structure 6, multiple sulfur atoms may be used to attach the conductive oligomer to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

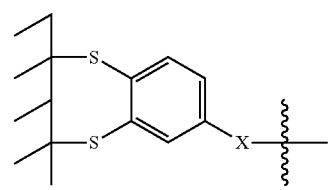

Structure 2

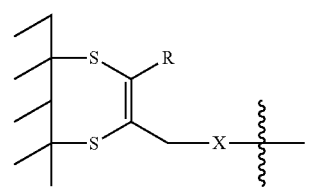

Structure 3

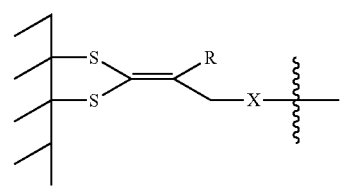

Structure 4

It should also be noted that similar to Structure 4, it may be possible to have a conductive oligomer terminating in a single carbon atom with three sulfur moieties attached to the electrode.

Figure 2:
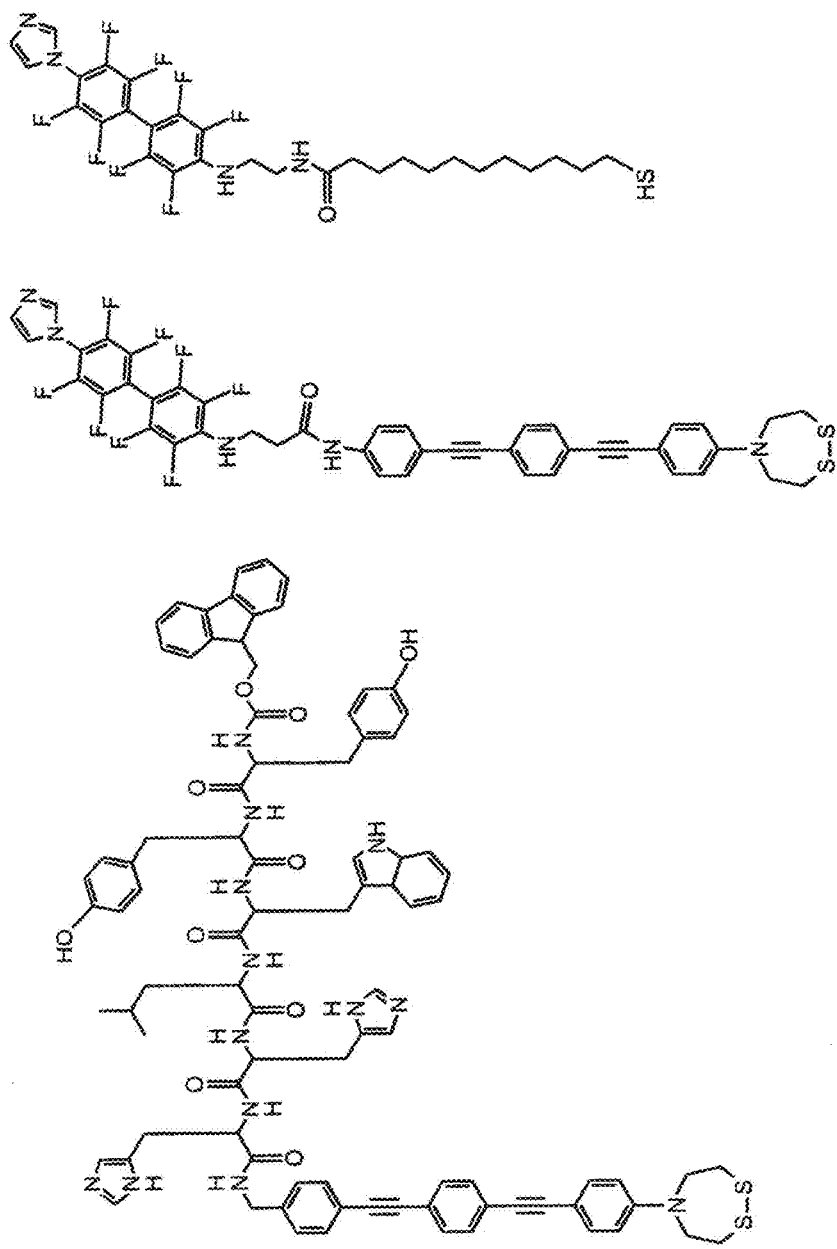
FIG. 2 depicts exemplary examples of diluents used in the "side-by-side" arrangement shown in FIG. 1 (separate diluents is optional).
Figure 3A:
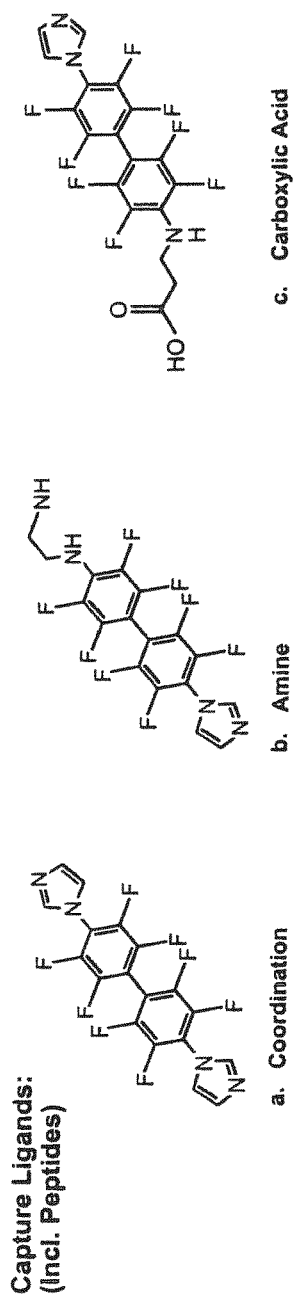
FIG. 3A shows capture ligands specific for Cytochrome P450 and analogue analytes.
Figure 3C:
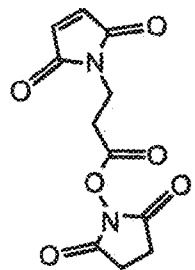
FIG. 3C depict some exemplary compounds with a maleimide reactive functional group.
Figure 3C:
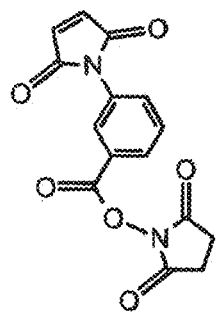
Figure 3C:
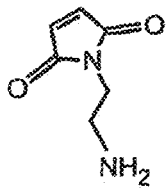
Figure 3C:
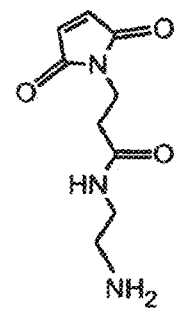
Figure 4:
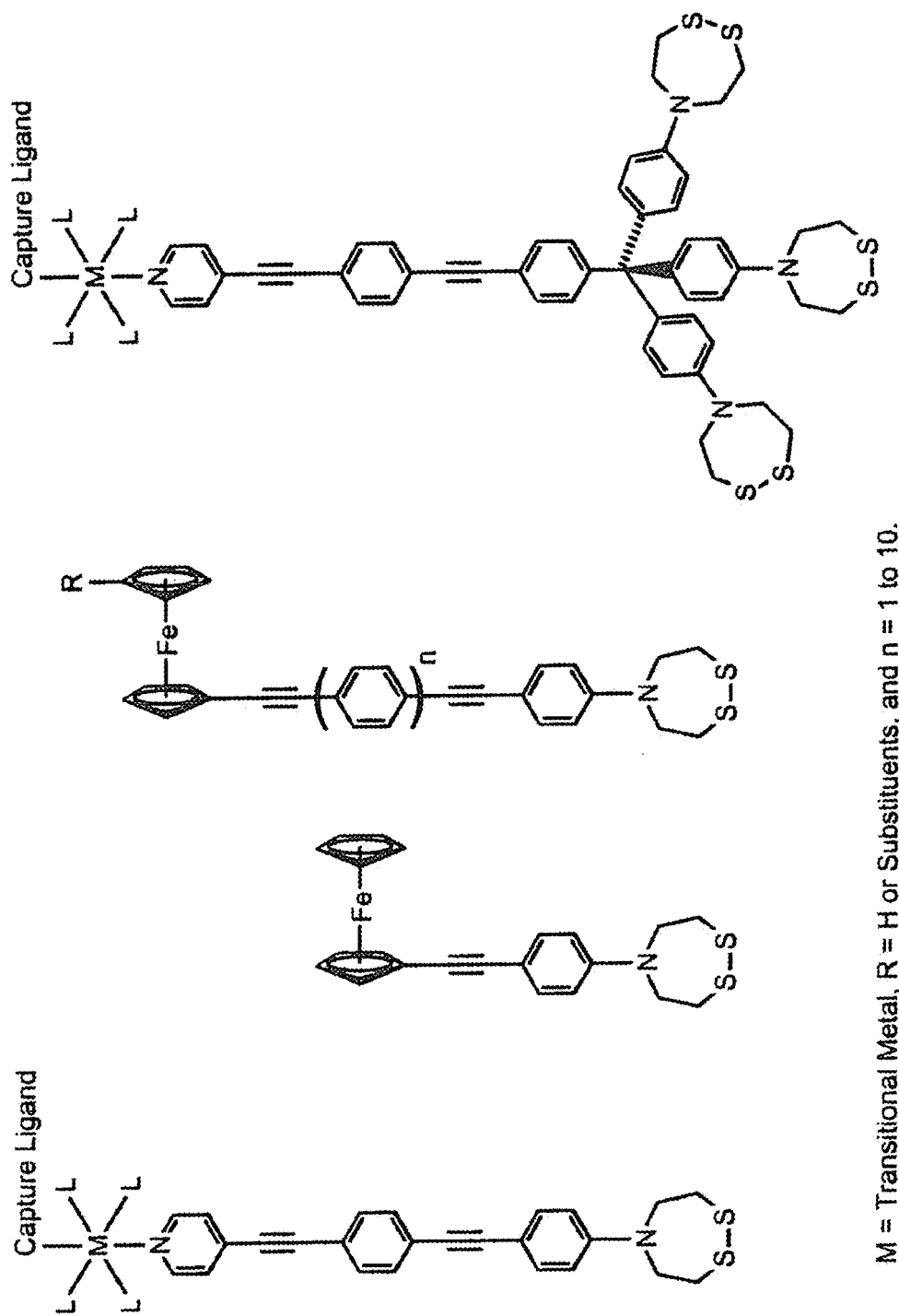
FIG. 4 depicts some exemplary compounds with different possible anchors as shown in FIG. 1
Figure 5A:
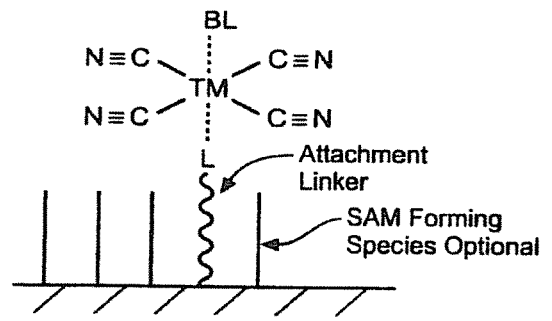
FIGS. 5A and 5B depict several schematics of suitable geometries of the present invention.
Figure 5A:
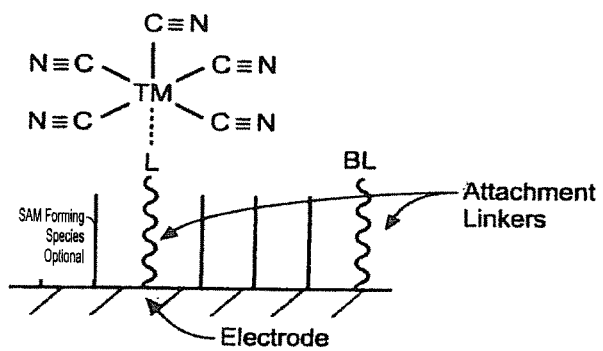
Figure 5A:
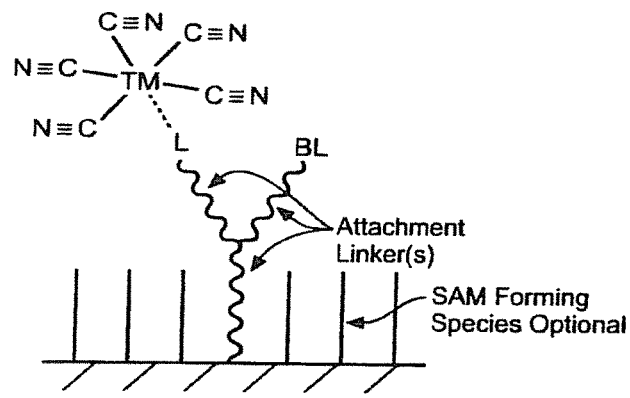
Figure 5B:
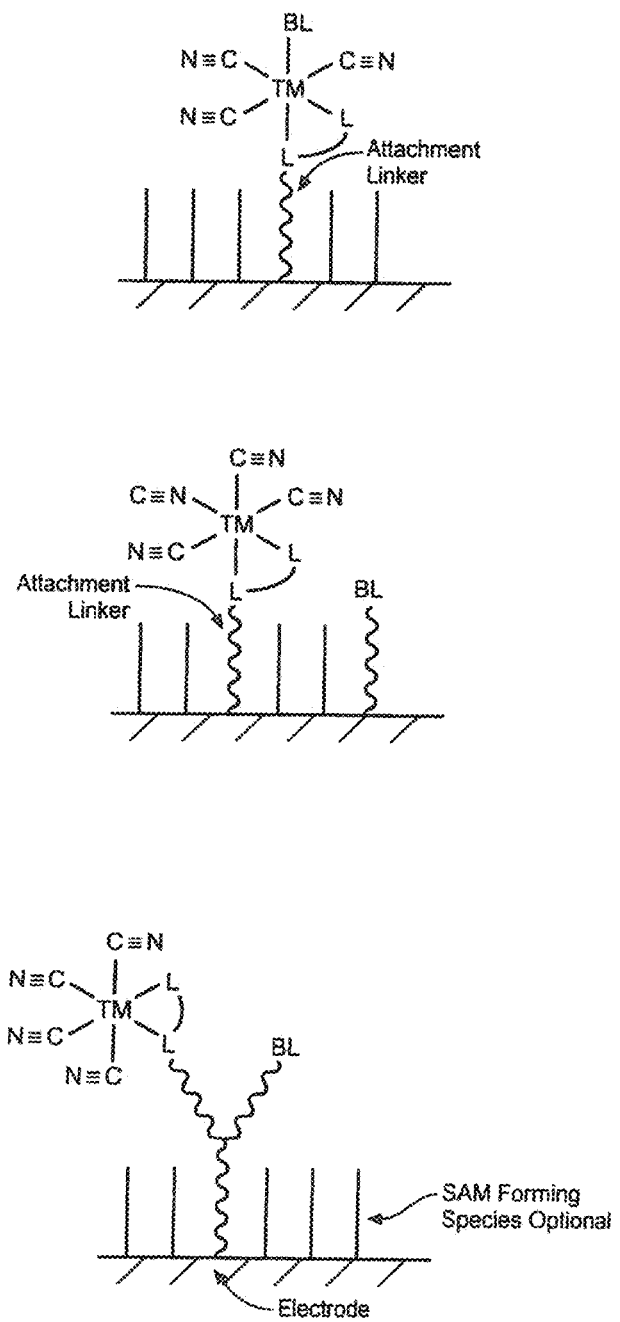
Figure 6:
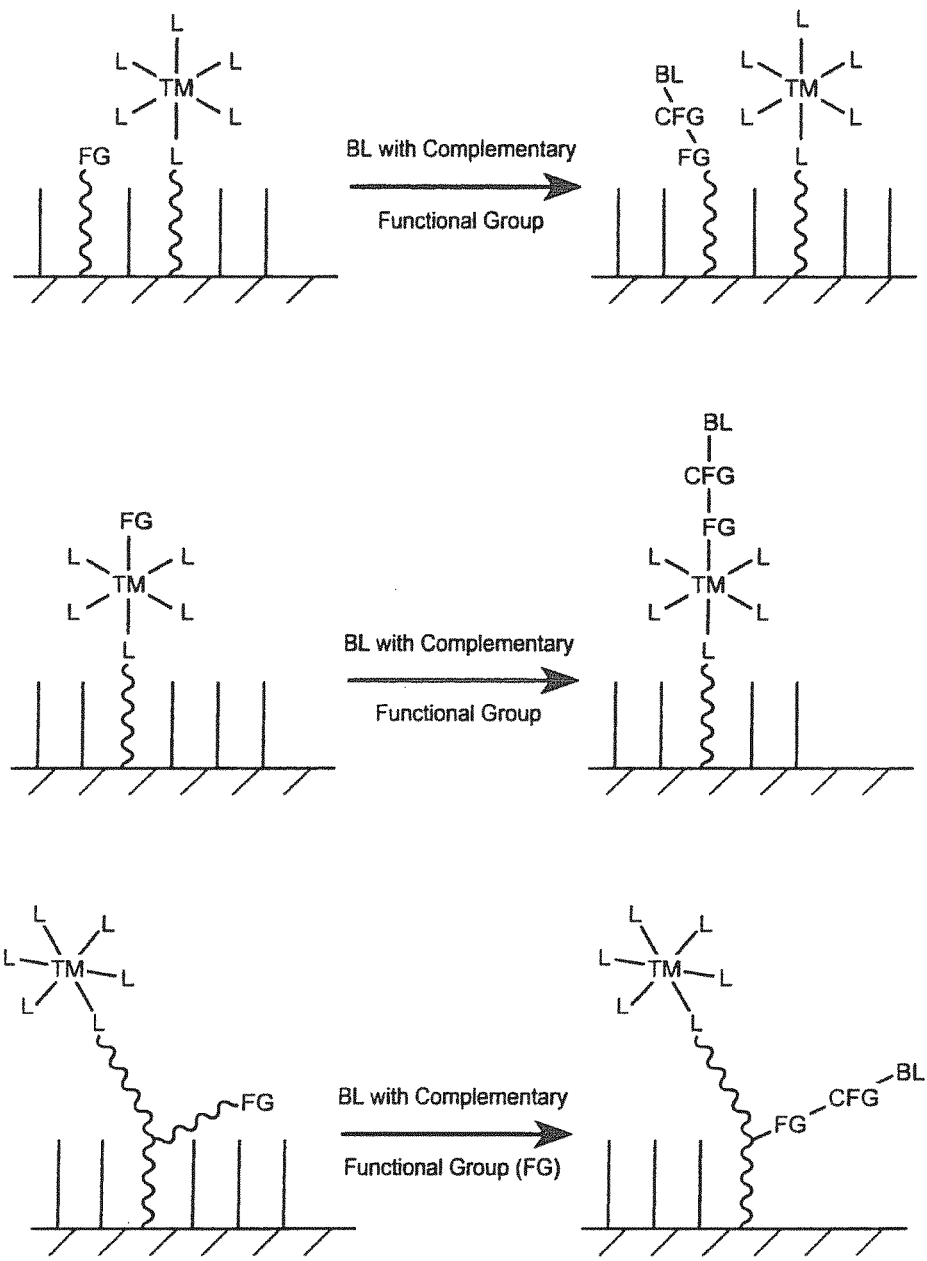
FIG. 6 depicts a general scheme for producing the biochips of the invention.
Figure 7:
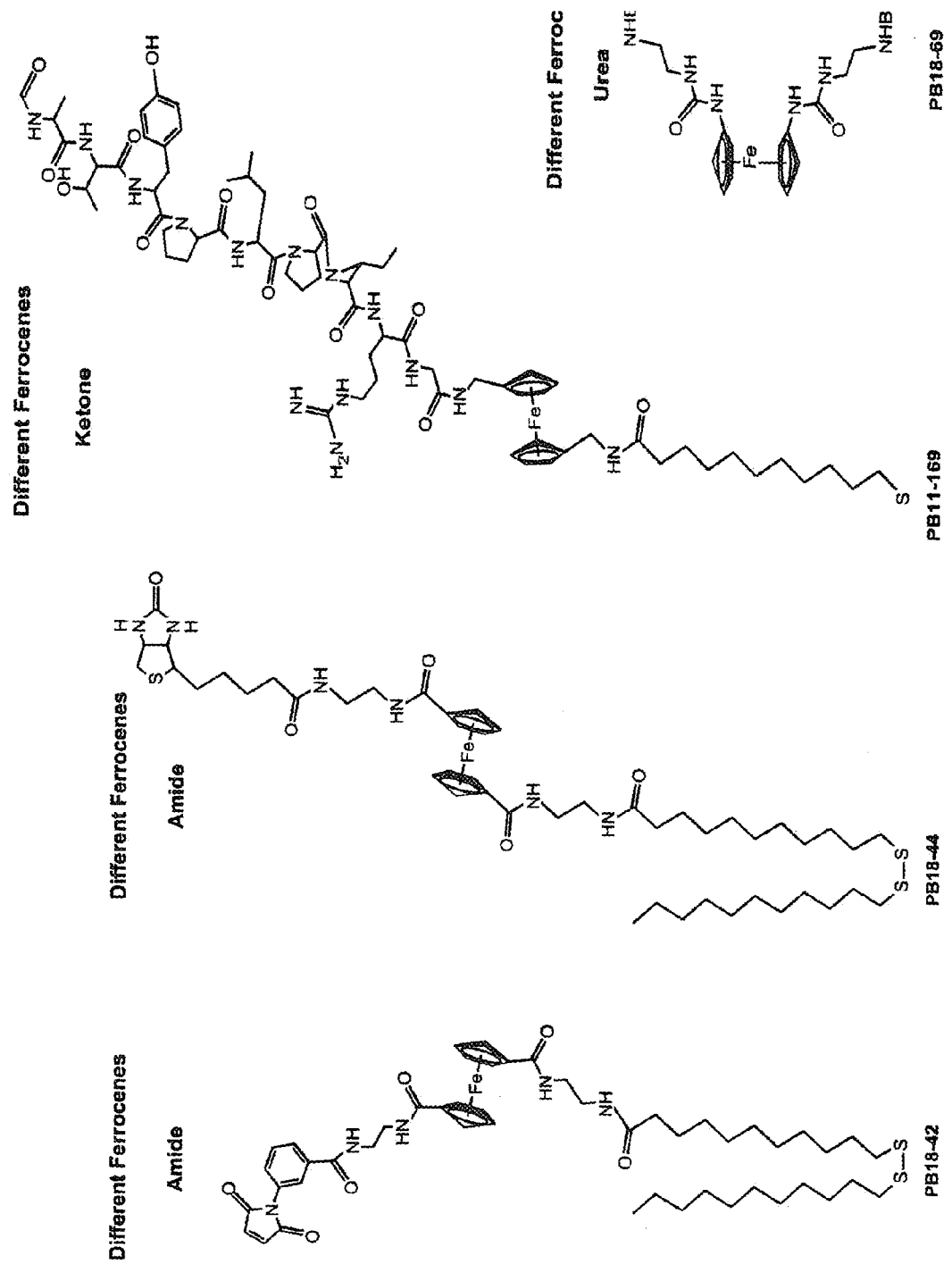
FIG. 7 depicts some exemplary compounds. Similar compounds can be constructed with different anchors, such as disulfide cyclic anchor groups, for example, or different spacers.
Figure 8:
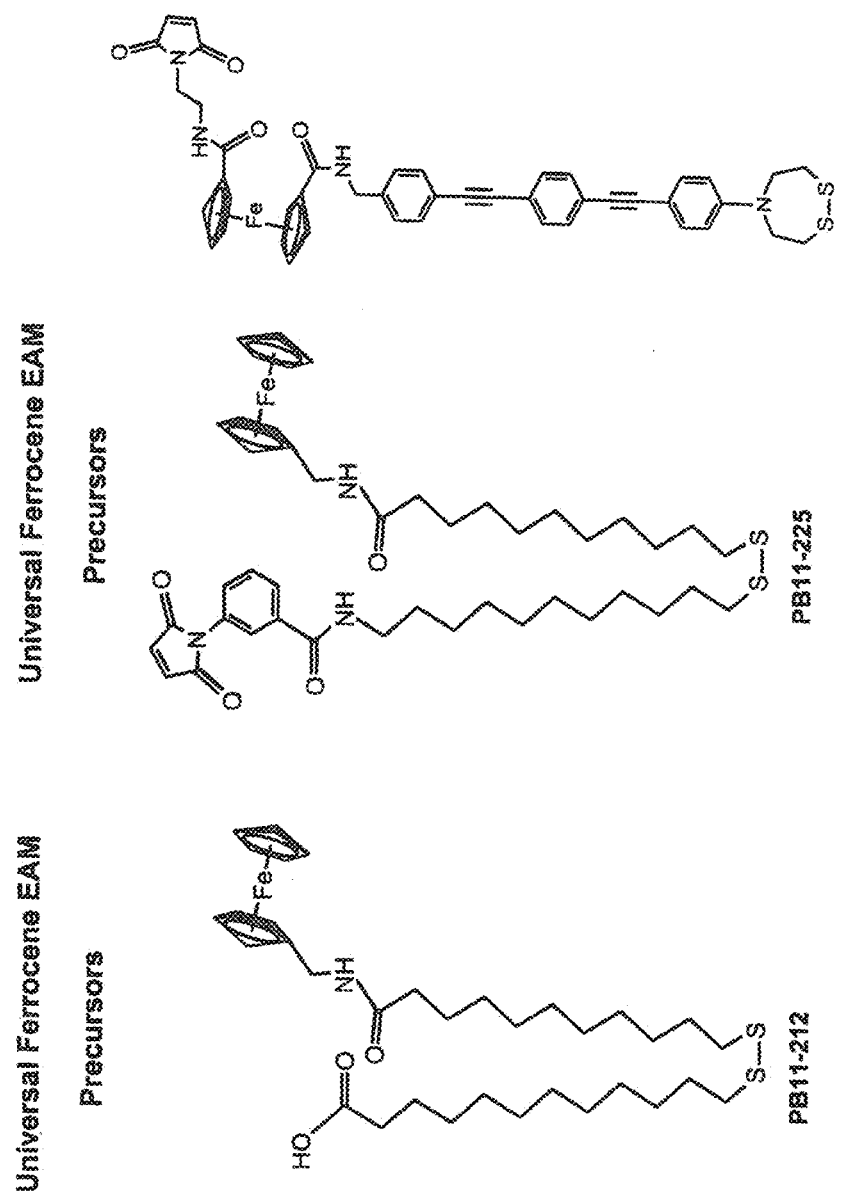
FIG. 8 depicts some exemplary compounds using ferrocene as the EAM in the 1-1' and 1-substitution mode. Similar compounds can be constructed with different anchors, such as disulfide cyclic anchor groups, for example, or different spacers. Similar compounds can be constructed with different anchors, such as disulfide cyclic anchor groups, for example, or different spacers.
Figure 9:
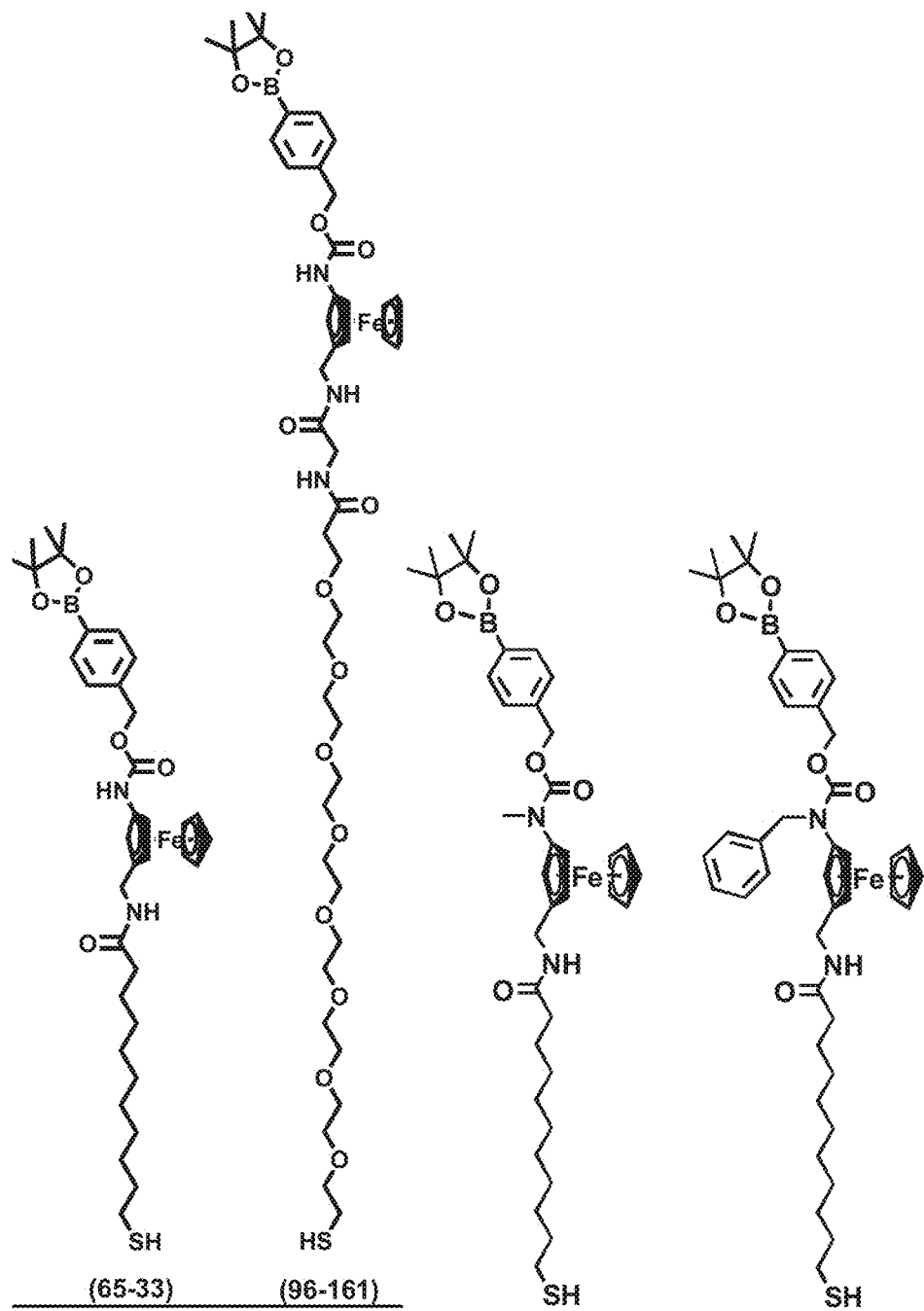
FIG. 9 depicts four compounds containing a peroxide trigger, self-immolative group, ferrocene redox complex, and thiolated anchor.
Figure 10:
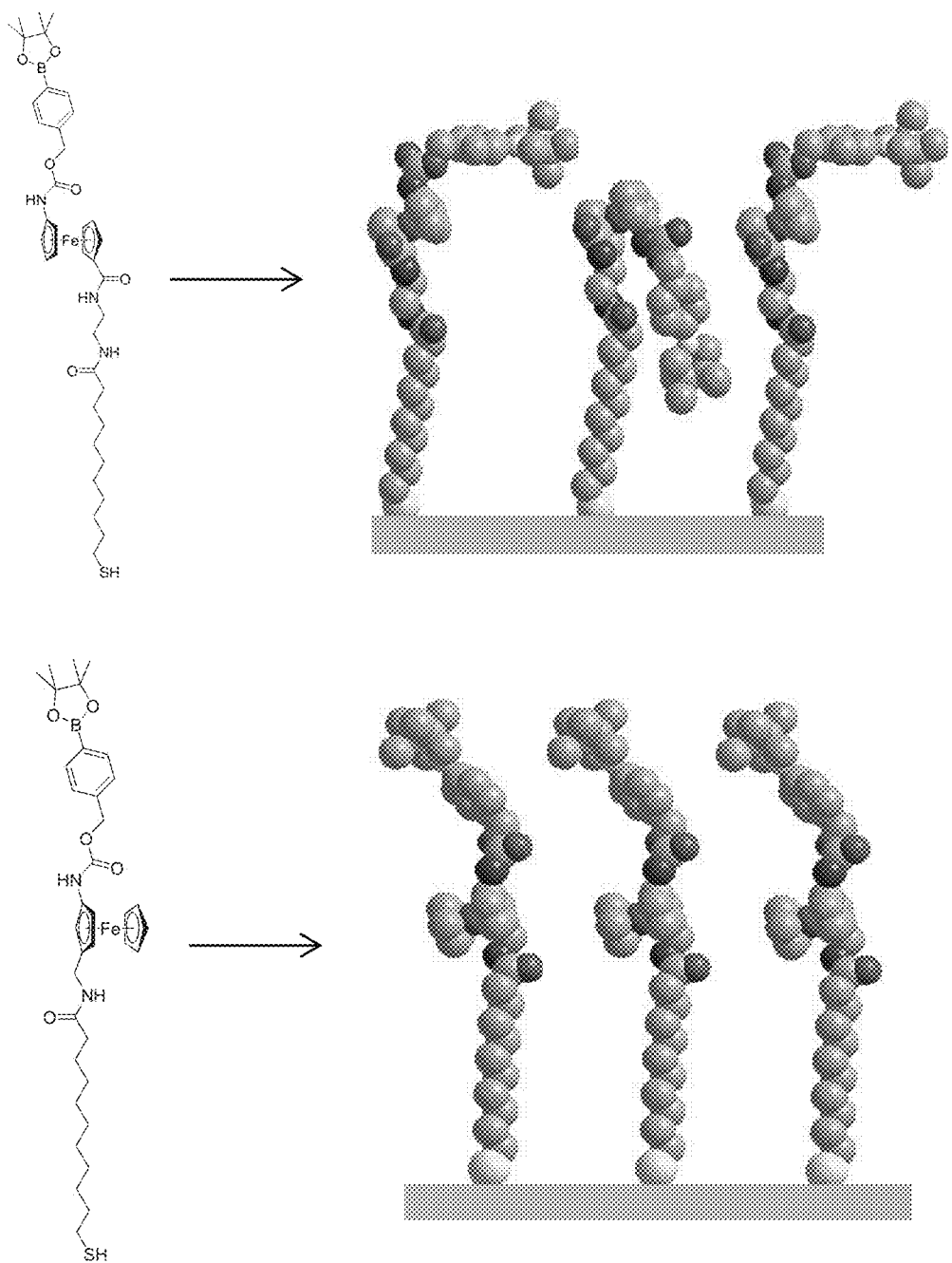
FIG. 10 shows a comparison of a 1,1'-ferrocene EAM monolayer and a 1,3-ferrocene EAM monolayer. The 1,1'-ferrocene EAM has additional degrees of freedom that allow the peroxide sensitive moiety to intercalate into the SAM. In the case of the 1,3-ferrocene EAM, since both substituents are connected to the same cyclopentadieneyl ring the "trans" geometry is enforced.
Figure 11A:
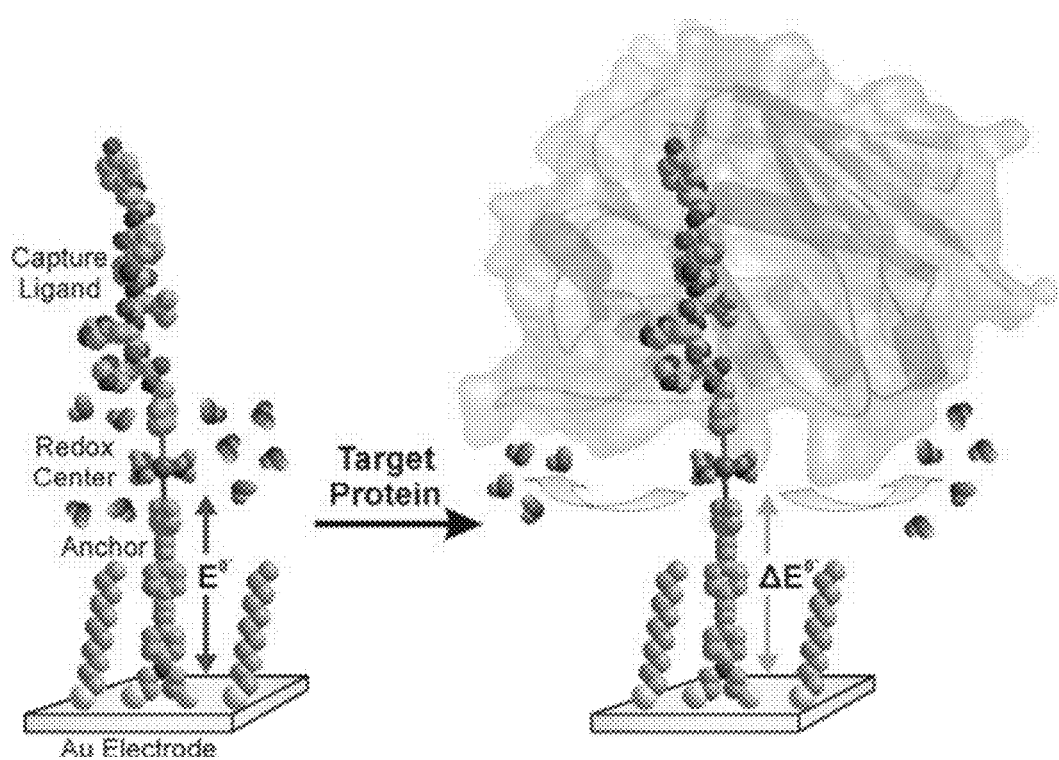
FIG. 11A shows a general schematic of an EAM monolayer on a gold electrode before and after target binding to the capture ligand based on a general detection scheme using reorganization energy. Prior to binding the redox center is well solvated in water; after target binding the water molecule are excluded from the redox center giving rise to a change in redox potential.
Figure 11B:
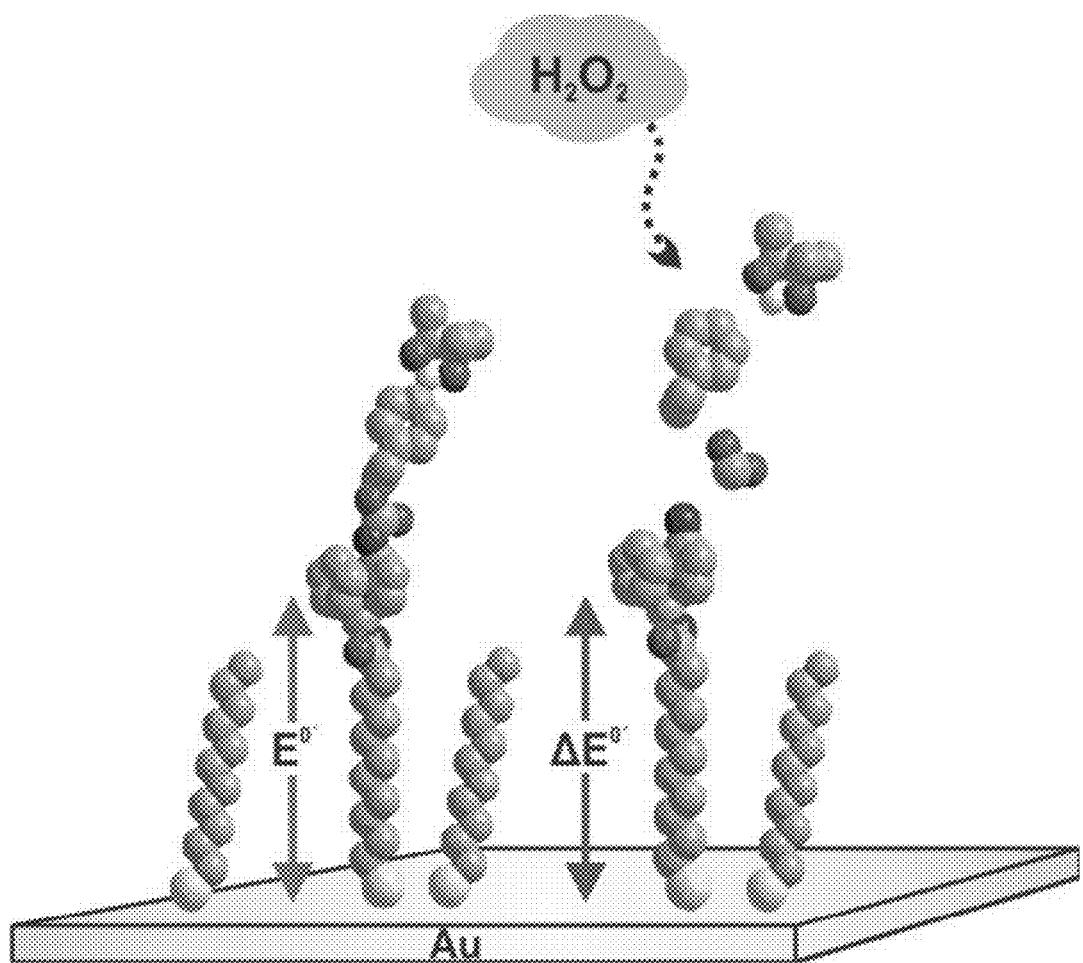
FIG. 11B shows a general schematic of a peroxide sensitive EAM monolayer on a gold electrode before and after hydrogen peroxide. Before peroxide, the trigger and self-immolative moieties are coupled and intact. After peroxide, the trigger and self-immolative moieties have reacted and become decoupled from the EAM.

In another aspect, the present invention provide anchor comprise conjugated thiols. Some exemplary complexes with conjugated thiol anchors are shown in FIG. 4. In some embodiments, the anchor comprises an alkylthiol group.

In another aspect, the present invention provides conjugated multipodal thio-containing compounds that serve as anchoring groups in the construction of electroactive moieties for analyte detection on electrodes, such as gold electrodes. That is, spacer groups (which can be attached to EAMs, ReAMCs, or an "empty" monolayer forming species) are attached using two or more sulfur atoms. These multipodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding head groups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

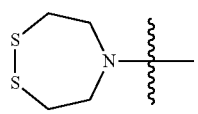

(IIIa)

In Structure (IIIa), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures.

In some embodiments, the anchor group and part of the spacer has the structure shown below

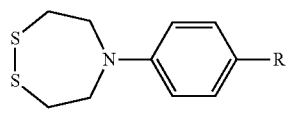

(IIIb)

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

C. Electroactive Moieties

In addition to anchor groups, the present invention provides compound comprising electroactive moieties. By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Particularly preferred are metals that do not change the number of coordination sites upon a change in oxidation state, including ruthenium, osmium, iron, platinum and palladium, with osmium, ruthenium and iron being especially preferred, and osmium finding particular use in many embodiments. In some embodiments, iron is not preferred. Generally, transition metals are depicted herein as TM or M.

The transitional metal and the coordinating ligands form a metal complex. By "ligand" or "coordinating ligand" (depicted herein in the figures as "L") herein is meant an atom, ion, molecule, or functional group that generally donates one or more of its electrons through a coordinate covalent bond to, or shares its electrons through a covalent bond with, one or more central atoms or ions.

The other coordination sites of the metal are used for attachment of the transition metal complex to either a capture ligand (directly or indirectly using a linker), or to the electrode (frequently using a spacer, as is more fully described below), or both. Thus for example, when the transition metal complex is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the transition metal complex to the electrode. For example, when the transition metal complex is attached to the electrode separately from the binding ligand as is more fully described below, all of the coordination sites of the metal (n) except 1 (n−1) may contain polar ligands.

Suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

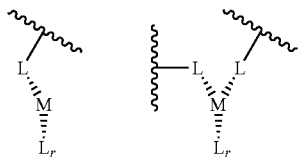

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used). As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as Lm). Suitable nitrogen donating ligands are well known in the art and include, but are not limited to, cyano (C≡N), NH2; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol [3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference. As will be appreciated in the art, any ligand donor(1)-bridge-donor(2) where donor (1) binds to the metal and donor(2) is available for interaction with the surrounding medium (solvent, protein, etc.) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N=C=O), thiocyanates, isonitrile, N2, O2, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts. Suitable sigma donating ligands using carbon, oxygen, sulfur and phosphorus are known in the art. For example, suitable sigma carbon donors are found in Cotton and Wilkinson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkinson. The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with 6-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [C5H5 (−1)] and various ring substituted and ring fused derivatives, such as the indenylide (−1) ion, that yield a class of bis(cyclopentadienyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [(C5H5)$_2$Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other .pi.-bonded and .delta.-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis. When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkinson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized. As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, NH2; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocyclic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

Self-Immolative Moieties

The EAMs of the invention include at least one self-immolative moiety that is covalently attached to the EAM such that the EAM has a first E0 when it is present and a second E0 when it has been removed as described below.

The term "self-immolative spacer" refers to a bifunctional chemical moiety that is capable of covalently linking two chemical moieties into a normally stable tripartate molecule. The self-immolative spacer is capable of spontaneously separating from the second moiety if the bond to the first moiety is cleaved. In the present invention, the self-immolative spacer links a peroxide sensitive moiety, e.g. a boron moiety, to the EAM. Upon exposure to peroxide, the boron moiety is oxidized and the spacer falls apart. Generally speaking, any spacer where irreversible repetitive bond rearrangement reactions are initiated by an electron-donating alcohol functional group (i.e. quinone methide motifs) can be designed with boron groups serving as triggering moieties that generate alcohols under oxidative conditions. Alternatively, the boron moiety can mask a latent phenolic oxygen in a ligand that is a pro-chelator for a transition metal. Upon oxidation, the ligand is transformed and initiates EAM formation in the SAM. For example, a sample chelating ligand is salicaldehyde isonicotinoyl hydrazone that binds iron.

As will be appreciated by those in the art, a wide variety of self-immolative moieties may be used with a wide variety of EAMs and peroxide sensitive moieties. Self-immolative linkers have been described in a number of references, including US Publication Nos. 20090041791; 20100145036 and U.S. Pat. Nos. 7,705,045 and 7,223,837, all of which are expressly incorporated by reference in their entirety, particularly for the disclosure of self-immolative spacers.

The self-immolative spacer can comprise a single monomeric unit or polymers, either of the same monomers (homopolymers) or of different monomers (heteropolymers). Alternatively, the self-immolative spacer can be a neighboring group to an EAM in a SAM that changes the environment of the EAM following cleavage analogous to the chemistry as recited in previous application "Electrochemical Assay for the Detection of Enzymes", U.S. Ser. No. 12/253,828, PCT/US2008/080363, hereby incorporated by reference.

Peroxide Sensitive Moieties

The self-immolative spacers join the peroxide sensitive moieties (PSMs, sometimes referred to herein as POMs) and the EAMs of the invention. In general, a peroxide sensitive moiety may contain boron. For example, suitable 1,2-diol compound may form an ester with boronic acid moiety to provide a peroxide sensitive moiety. Some exemplary boron-containing peroxide sensitive moieties are depicted below:

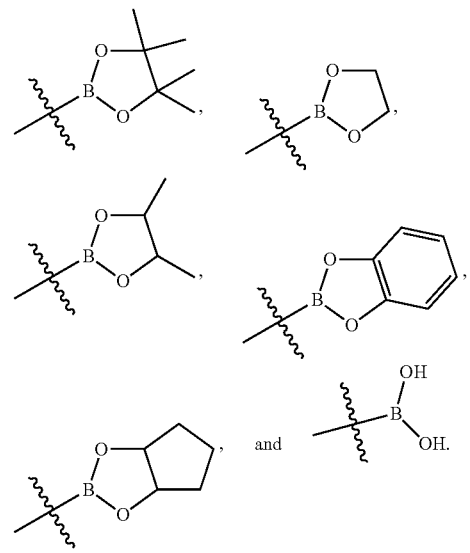

In addition, peroxide sensitive moieties include non-boron containing structures, such as

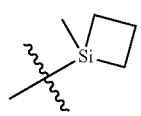 [SMILES: *[Si]1(C)CCC1]

described in Tlais et al. reference (*J. Org. Chem.* 2009, 74, 1876-1885), which is incorporated by reference herein.

For example, the figures herein depict the use of ferrocene derivatives, where the peroxide triggers a change from a benzyl carbamate with a p-substituted pinacol borate ester to an amine. This self-eliminating group has been described previously for generating amine-functionalized fluorophores in the presence of hydrogen peroxide (Sella, E.; Shabat, D. Self-immolative dendritic probe for the direct detection of triacetone triperoxide. Chem. Commun. 2008, 5701-5703; and Lo, L.-Cl; Chu, C.-Y. Development of highly selective and sensitive probes for hydrogen peroxide. Chem. Commun. 2003, 2728-2729 both of which are incorporated by reference. Other such groups (aryl borate esters and arylboronic acids) are also described in Sella and Lo. In addition, ferrocenylamines are known to exhibit redox behavior at lower potentials (~150 mV) as compared to their corresponding carbamate derivatives (see Sagi et al., Amperometric Assay for Aldolase Activity; Antibody-Catalyzed Ferrocenylamine Formation. Anal. Chem. 2006, 78, 1459-1461, incorporated by reference herein).

Some examples of EAMs are described herein.

Ferrocene-Based EAMs

In some embodiments, the EAMs comprise substituted 1,1'-ferrocenes. Ferrocene is air-stable. It can be easily substituted with both capture ligand and anchoring group. Upon binding of the target protein to the capture ligand on the ferrocene which will not only change the environment around the ferrocene, but also prevent the cyclopentadienyl rings from spinning, which will change the energy by approximately 4 kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, all incorporated by reference.

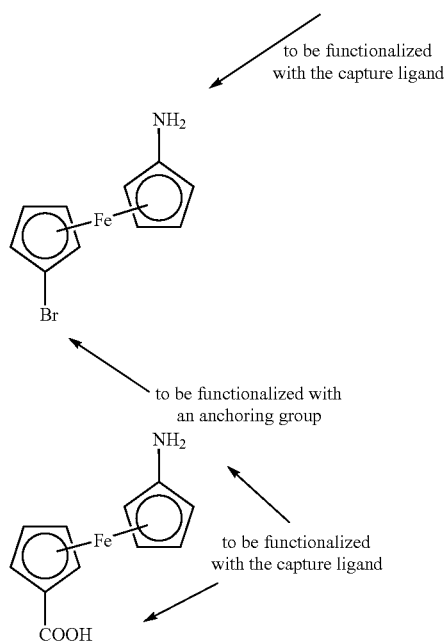

Figure 12:
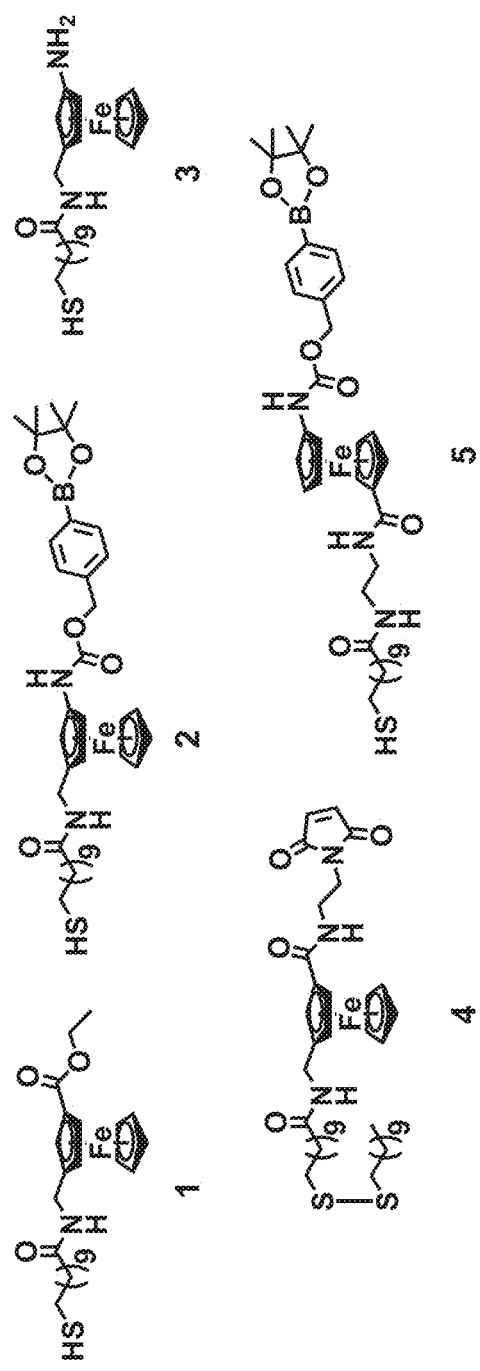
FIG. 12 shows the structures of 1,3-disubstituted ferrocenes 1-4 along with a 1,1'-disubstituted ferrocene 5 for SAM study comparison with 2.

In some other embodiments, the EAMs comprise 1,3-disubstituted ferrocenes. While 1,3-disubstituted ferrocenes are known (see, Bickert et al., Organometallics 1984, 3, 654-657; Farrington et al., Chem. Commun. 2002, 308-309; Pichon et al., Chem. Commun. 2004, 598-599; and Steurer et al., Organometallics 2007, 26, 3850-3859), electrochemical studies of this class of molecules in SAMs have not been reported in the literature. In contrast to 1,1'-disubstituted ferrocenes where cyclopentadienyl (Cp) ring rotation can place both Cp substituents in an eclipsed conformation, 1,3-disubstituted ferrocene regioisomers provide a molecular architecture that enforces a rigid geometry between these Cp groups. Thus, 1,3-disubstituted ferrocenes that possess an anchoring group, such as an organosulfur group for gold anchoring, and a capture ligand such as a receptor group, protein capture ligands and/or enzyme-reactive moieties are suited for SAM-based electrochemical biosensing applications where the receptor is displayed at the solution/SAM interface with limited degrees of freedom (see FIG. 1, where X is an anchoring group and Y can comprise a capture ligand). Representative examples of 1,3-disubstituted ferrocenes are shown in FIG. 12, such as compounds 1-5. An example of a 1,3-disubstituted ferrocene for attaching both anchoring and capture ligands is shown below:

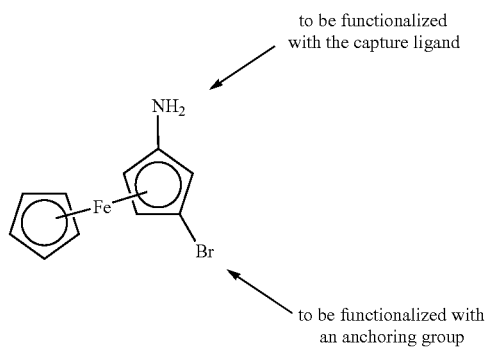

When EAMs comprising 1,3-disubstituted ferrocenes and a capture ligand, such as a peroxide-sensitive moiety, are used for formation of a SAM, a surprising and unexpected enhancement for the surface plasmon resonance (SPR) behavior is seen. For example, upon decomposition of an carbamate-linked benzylboronate ester attached to a 1,3-disubstituted ferrocene from exposure of the boronate to hydrogen peroxide under alkaline conditions, an increased negative angle shift, from a change in the SAM thickness, is observed by SPR.

In some embodiments the anchor and capture ligands are attached to the same ligand for easier synthesis. In some embodiments the anchor and capture ligand are attached to different ligands.

There are many ligands that can be used to build the new architecture disclosed herein. They include but not limited to carboxylate, amine, thiolate, phosphine, imidazole, pyridine, bipyridine, terpyridine, tacn (1,4,7-Triazacyclononane), salen (N,N'-bis(salicylidene)ethylenediamine), acacen (N,N'-Ethylenebis(acetylacetoniminate(-)), EDTA (ethylenediamine tetraacetic acid), DTPA (diethylene triamine pentaacetic acid), Cp (cyclopentadienyl), pincer ligands, and scorpionates. In some embodiments, the preferred ligand is pentaamine.

Pincer ligands are a specific type of chelating ligand. A pincer ligand wraps itself around the metal center to create bonds on opposite sides of the metal as well as one in between. The effects pincer ligand chemistry on the metal core electrons is similar to amines, phosphines, and mixed donor ligands. This creates a unique chemical situation where the activity of the metal can be tailored. For example, since there is such a high demand on the sterics of the complex in order to accommodate a pincer ligand, the reactions that the metal can participate in is limited and selective.

Scorpionate ligand refers to a tridentate ligand which would bind to a metal in a fac manner. The most popular class of scorpionates are the tris(pyrazolyl)hydroborates or Tp ligands. A Cp ligand is isolobal to Tp.

In some embodiments, the following restraints are desirable: the metal complex should have small polar ligands that allow close contact with the solvent.

In some embodiments, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5$ (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [($C_5H_5$)$_2$Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other .pi.-bonded and .delta.-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

Of particular use in the present invention are EAMs that are metallocenes, and in particular ferrocenes, which have at least a first self-immolative moiety attached, although in some embodiments, more than one self-immolative moiety is attached as is described below (it should also be noted that other EAMs, as are broadly described herein, with self-immolative moieties can also be used). In some embodiments, when more than one self-immolative moiety is attached to a ferrocene, they are all attached to one of the cyclopentydienyl rings. In some embodiments, the self-immolative moieties are attached to different rings. In some embodiments, it is possible to saturate one or both of the cyclopentydienyl rings with self-immolative moieties, as long as one site is used for attachment to the electrode.

In addition, EAMs generally have an attachment moiety for attachment of the EAM to the conductive oligomer which is used to attach the EAM to the electrode. In general, although not required, in the case of metallocenes such as ferrocenes, the self-immolative moiety(ies) are attached to one of the cyclopentydienyl rings, and the attachment moiety is attached to the other ring, as is generally depicted in FIG. 1, although attachment to the same ring can also be done. As will be appreciated by those in the art, any combination of self-immolative moieties and at least one attachment linker can be used, and on either ring.

In addition to the self-immolative moiety(ies) and the attachment moiety(ies), the ferrocene can comprise additional substituent groups, which can be added for a variety of reasons, including altering the E0 in the presence or absence of at least the self-immolative group. Suitable substituent groups, frequently depicted in associated and incorporated references as "R" groups, are recited in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; and U.S. Provisional Patent Application No. 61/366,013, filed Jul. 20, 2010, hereby incorporated by reference.

In some embodiments, such as depicted below, the EAM does not comprise a self-immolative moiety, in the case where the peroxide-sensitive moiety is attached directly to the EAM resulting in quantifiable electrochemical signal at two unique potentials, $E°_1$ and $E°_2$. When the peroxide-sensitive moiety is exposed to peroxide. As shown below, one embodiment allows the peroxide-sensitive moiety to be attached directly to the EAM (in this case, a ferrocene), such that the ferrocene has a first $E°_1$ when the pinacol boronate ester moiety is attached, and a second $E°_2$ when removed, e.g. in the presence of the peroxide. Typically the PSM (Peroxide sensitive molecule) pinacol boronate is attached in a 1,1' substitution to the anchor on the ferrocene, as shown below.

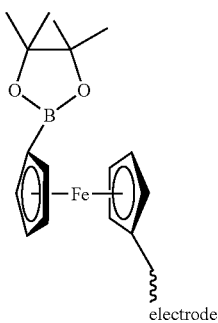

electrode

In a preferred embodiment, such as depicted below, the EAM does not comprise a self-immolative moiety, in the case where the peroxide-sensitive moiety is attached directly to the EAM resulting in quantifiable electrochemical signal at two unique potentials, $E°_1$ and $E°_2$. When the peroxide-sensitive moiety is exposed to peroxide. As shown below, one embodiment allows the peroxide-sensitive moiety to be attached directly to the EAM (in this case, a ferrocene), such that the ferrocene has a first $E°_1$ when the pinacol boronate ester moiety is attached, and a second $E°_2$ when removed, e.g. in the presence of the peroxide. The PSM (Peroxide sensitive molecule) pinacol boronate can be attached in a unique 1,3 substitution to the anchor on the ferrocene, as shown below.

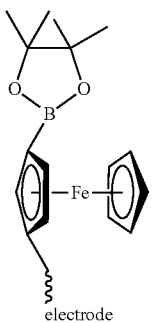

electrode

In one aspect of the invention, ferrocene compounds are of formula (III):

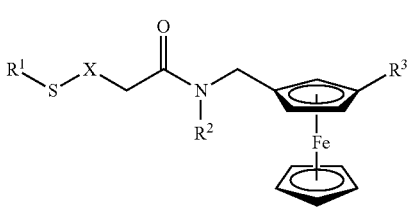

wherein
$R^1$ is hydrogen, —S—$C_1$-$C_{20}$ alkyl, —S—$C_2$-$C_{20}$ alkenyl, or —S—$C_2$-$C_{20}$ alkynyl,
X is —$C_1$-$C_{20}$ alkyl-, —$C_2$-$C_{20}$ alkenyl-, —$C_2$-$C_{20}$ alkynyl-, —$X^1$—CONH—, —$X^1$—$CO_2$—, or —$X^1$—OCNH—, where $X^1$ is selected from the group consisting of polyoxyalkylene, of polymethylene, oligophenylene, and polyphenylene(ethynylene);
$R^2$ is hydrogen or $C_1$-$C_6$ alkyl; and
$R^3$ is —$NR^4R^5$, —$CO_2R^5$, —$CONR^4R^5$, or —$NR^5CO_2$—$R^6$;

where $R^4$ is hydrogen, or $C_1$-$C_6$ alkyl;
where $R^5$ is hydrogen, $C_1$-$C_6$ alkyl, $C_2$-$C_6$ alkenyl, $C_2$-$C_6$ alkynyl, aryl($C_1$-$C_6$ alkyl), aryl($C_2$-$C_6$ alkenyl), heteroaryl ($C_1$-$C_6$ alkyl), or heteroaryl($C_2$-$C_6$ alkenyl), where each optionally substituted with one to four substituents selected from halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —$CO_2H$, —COH, —$CO_2$($C_1$-$C_6$ alkyl), —$CONH_2$, —$CON(C_1$-$C_6$ alkyl)$_2$, or peroxide sensitive moiety; and
where $R^6$ is $C_1$-$C_6$ alkyl, $C_2$-$C_6$ alkenyl, $C_2$-$C_6$ alkynyl, aryl ($C_1$-$C_6$ alkyl), aryl($C_2$-$C_6$ alkenyl), heteroaryl($C_1$-$C_6$ alkyl), or heteroaryl($C_2$-$C_6$ alkenyl), where each optionally substituted with one to four substituents selected from halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, di$C_1$-$C_6$alkylamino, —$CO_2H$, —COH, —$CO_2$($C_1$-$C_6$ alkyl), —$CONH_2$, —$CON(C_1$-$C_6$ alkyl)$_2$, or peroxide sensitive moiety.

In one embodiment of the invention, the disclosure provides ferrocene compounds of formula (III) wherein $R^1$ is hydrogen, or —S—$C_1$-$C_{20}$ alkyl.

In another embodiment, the disclosure provides ferrocene compounds as described above with reference to formula (III), wherein $R^1$ is hydrogen.

In other embodiments, the disclosure provides compounds as described above with reference to formula (III), wherein $R^1$ is —S—$C_6$-$C_{12}$ alkyl.

In other embodiments, the disclosure provides ferrocene compounds as described above with reference to formula (III), wherein X is —$C_1$-$C_{20}$ alkyl-, —$C_2$-$C_{20}$ alkenyl-, or —$C_2$-$C_{20}$ alkynyl-. In further embodiments, X is —$C_1$-$C_{20}$ alkyl-. In further embodiments, X is —$C_5$-$C_{11}$ alkyl-.

In other embodiment, the disclosure provides ferrocene compounds as described above with reference to formula (III), wherein X is nonylene.

In yet further embodiments, the disclosure provides ferrocene compounds as described above with reference to formula (III), wherein X is —$X^1$—CONH—, —$X^1$—$CO_2$—, or —$X^1$—OCNH—, and where $X^1$ is selected from the group consisting of polyoxyalkylene, of polymethylene, oligophenylene, and polyphenylene(ethynylene).

In further embodiments, the disclosure provides ferrocene compounds as described above with reference to formula (III), wherein X is —$X^1$—CONH—, and $X^1$ is polyoxyalkylene.

In other embodiments, the disclosure provides ferrocene compounds as described above with reference to formula (III), wherein $R^3$ is —$NR^4R^5$, —$CO_2R^5$, or —$CONR^4R^5$. In further embodiments, $R^3$ is —$NH_2$. In additional embodiments, $R^3$ is —$CO_2$($C_1$-$C_6$ alkyl) or —$CO_2$($C_1$-$C_6$ alkyl).

In yet further embodiments, the disclosure provides ferrocene compounds as described above with reference to formula (III), wherein $R^3$ is —$CONR^4R^5$; $R^4$ is hydrogen, or $C_1$-$C_6$ alkyl; and $R^5$ is $C_1$-$C_6$ alkyl, aryl($C_1$-$C_6$ alkyl), or heteroaryl($C_1$-$C_6$ alkyl).

In other embodiments, the disclosure provides ferrocene compounds as described above with reference to formula (III), wherein $R^3$ is —$NR^5CO_2$—$R^6$; and $R^5$ is hydrogen, $C_1$-$C_6$ alkyl, or aryl($C_1$-$C_6$ alkyl).

In yet further embodiments, the disclosure provides ferrocene compounds as described above with reference to formula (III), wherein $R^6$ is aryl($C_1$-$C_6$ alkyl) or $C_2$-$C_6$ alkenyl, where each optionally substituted with peroxide sensitive moiety. In yet another embodiment, the peroxide sensitive moiety is 4,4,5,5-tetramethyl-1,3,2-dioxaborolanyl.

In further embodiments, the disclosure provides ferrocene compounds as described above with reference to formula (III), wherein $R^6$ is heteroaryl($C_1$-$C_6$ alkyl), which is optionally substituted with peroxide sensitive moiety. In yet another embodiment, the peroxide sensitive moiety is 4,4,5,5-tetramethyl-1,3,2-dioxaborolanyl. In one embodiment, the heteroaryl moiety of $R^6$ is pyridine. In another embodiment, $R^6$ is pyridinylmethyl. Such described in Perry-Feigenbaum et al. reference (*Org. Biomol. Chem.*, 2009, 7, 4825-4828), which is incorporated by reference herein.

In some embodiments, the disclosure provides ferrocene compounds as described above with reference to formula (III), wherein $R^3$ is:

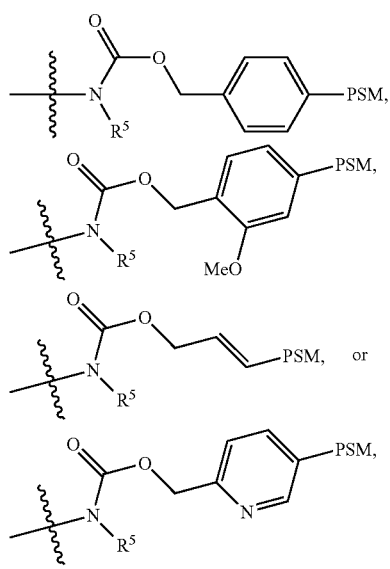

wherein PSM is peroxide sensitive moiety.

In some embodiments, the disclosure provides ferrocene compounds as described above with reference to formula (III), wherein the peroxide sensitive moiety is selected from the group consisting of:

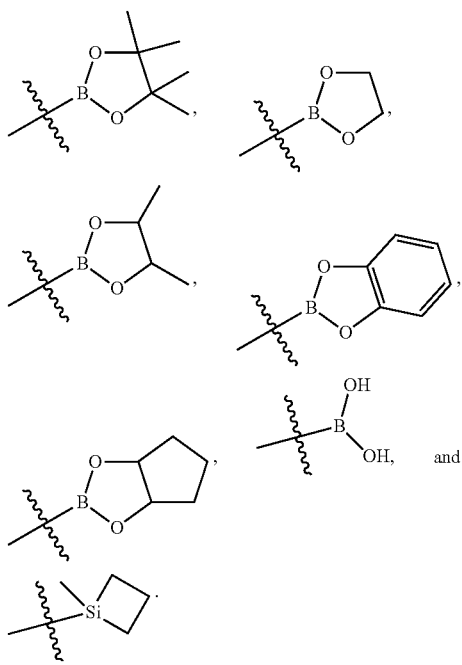

In some embodiments, the disclosure provides ferrocene compounds as described above with reference to formula (III), wherein $R^3$ is:

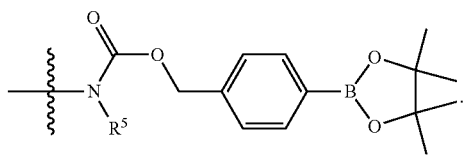

In other particular embodiments, the disclosure provides ferrocene compounds that are:

-continued

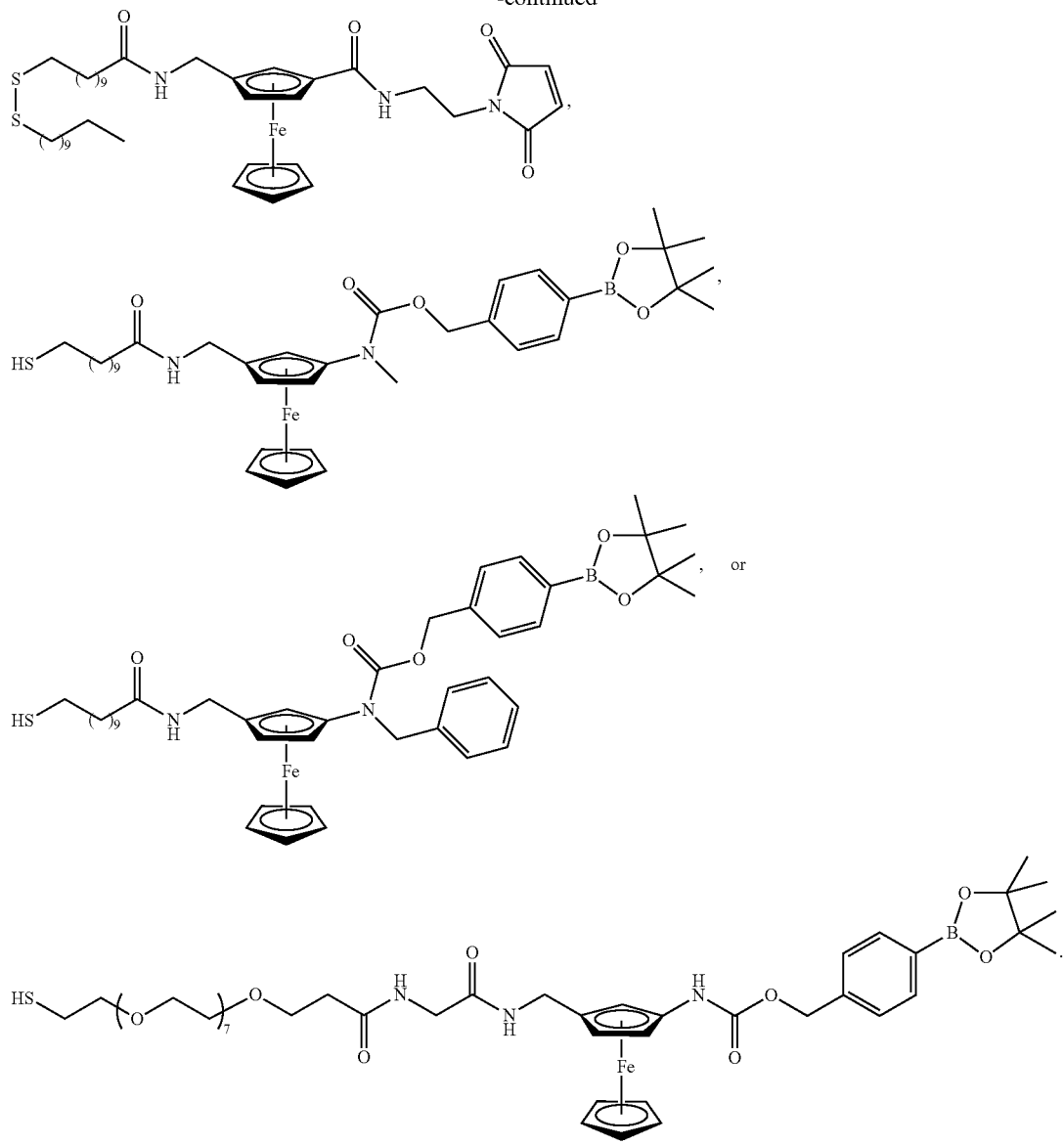

D. Spacer Groups

In some embodiments, the EAM or ReAMC is covalently attached to the anchor group (which is attached to the electrode) via an attachment linker or spacer ("Spacer 1"), that further generally includes a functional moiety that allows the association of the attachment linker to the electrode. See for example U.S. Pat. No. 7,384,749, incorporated herein by reference in its entirety and specifically for the discussion of attachment linkers). It should be noted in the case of a gold electrode, a sulfur atom can be used as the functional group (this attachment is considered covalent for the purposes of this invention). By "spacer" or "attachment linker" herein is meant a moiety which holds the redox active complex off the surface of the electrode. In some embodiments, the spacer is a conductive oligomer as outlined herein, although suitable spacer moieties include passivation agents and insulators as outlined below. In some cases, the spacer molecules are SAM forming species. The spacer moieties may be substantially non-conductive, although preferably (but not required) is that the electron coupling between the redox active molecule and the electrode (HAB) does not limit the rate in electron transfer.

In addition, attachment linkers can be used to between the coordination atom of the capture ligand and the capture ligand itself, in the case when ReAMCs are utilized. Similarly, attachment linkers can be branched. In addition, attachment linkers can be used to attach capture ligands to the electrode when they are not associated in a ReAMC. One end of the attachment linker is linked to the EAM/ReAMC/capture ligand, and the other end (although as will be appreciated by those in the art, it need not be the exact terminus for either) is attached to the electrode. The covalent attachment of the conductive oligomer containing the redox active molecule (and the attachment of other spacer molecules) may be accomplished in a variety of ways, depending on the electrode and the conductive oligomer used. See for example Structures 12-19 and the accompanying text in U.S. Patent Publication No. 20020009810, hereby incorporated by reference in its entirety.

In general, the length of the spacer is as outlined for conductive polymers and passivation agents in U.S. Pat. Nos. 6,013,459, 6,013,170, and 6,248,229, as well as U.S. Pat. No. 7,384,749 all herein incorporated by reference in their entireties. As will be appreciated by those in the art, if the spacer becomes too long, the electronic coupling between the redox active molecule and the electrode will decrease rapidly.

In some embodiments, the EAM or ReAMC is covalently attached to the capture ligand or functional group via an attachment linker or spacer ("Spacer 2"). Spacer 2 is a linker, such as, but not limited to, a long chain (e.g., $C_3$-$C_{20}$) alkyl, long chain alkenyl, long chain alkynyl, polymer chain (such as polyethylene glycol), or some other long chain moiety that offers flexibility and extend the capture ligand away from the monolayer enabling more efficient target binding.

E. Capture Ligands

A variety of molecules can be used in the present invention as capture ligands. By "capture ligand" or "binding ligand" or "capture binding ligand" or "capture binding species" or "capture probe" herein is meant a compound that is used to probe for the presence of the target analyte that will bind to the target analyte. Generally, the capture ligand allows the attachment of a target analyte to the electrode, for the purposes of detection. As is more fully outlined below, attachment of the target analyte to the capture probe may be direct (i.e. the target analyte binds to the capture ligand) or indirect (one or more capture extender ligands are used). By "covalently attached" herein is meant that two moieties are attached by at least one bond, including sigma bonds, pi bonds and coordination bonds.

In some embodiments, the binding is specific, and the capture ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding which is not highly specific; for example, the systems may use different capture ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. This binding should be sufficient to remain bound under the conditions of the assay, including wash steps to remove non-specific binding. Generally, the disassociation constants of the analyte to the binding ligand will be in the range of at least $10^{-4}$-$10^{-6}$ $M^{-1}$, with a preferred range being $10^{-5}$ to $10^{-9}$ $M^{-1}$ and a particularly preferred range being $10^{-7}$-$10^{-9}$ $M^{-1}$. As will be appreciated by those in the art, the composition of the capture ligand will depend on the composition of the target analyte. Capture ligands to a wide variety of analytes are known or can be readily found using known techniques. For example, when the analyte is a single-stranded nucleic acid, the capture ligand may be a complementary nucleic acid. Similarly, the analyte may be a nucleic acid binding protein and the capture binding ligand is either single-stranded or double stranded nucleic acid; alternatively, the binding ligand may be a nucleic acid-binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates and inhibitors. As will be appreciated by those in the art, any two molecules that will associate may be used, either as an analyte or as the binding ligand. Suitable analyte/binding ligand pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-binding ligand pairs. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors. As described herein, the capture ligand can be attached to the coordinating ligand and/or anchor via a covalent bond. The method of attachment of the capture binding ligand will generally be done as is known in the art, and will depend on the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or through the use of a linker, sometimes depicted herein as "Z". Linkers are known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred. Z may also be a sulfone group, forming sulfonamide.

In this way, capture binding ligands comprising proteins, lectins, nucleic acids, small organic molecules, carbohydrates, etc. can be added.

In some embodiment, antibodies or a fragment thereof are used as capture ligands. By "antibody" herein is meant a member of a family of glycosylated proteins called immunoglobulins, which can specifically combine with an antigen. The term "antibody" includes full-length as well antibody fragments, as are known in the art, including Fab, Fab2, single chain antibodies (Fv for example), chimeric antibodies, humanized and human antibodies, etc., either produced by the modification of whole antibodies or those synthesized de novo using recombinant DNA technologies, and derivatives thereof. However, in some embodiments, whole antibodies are not preferred. This is because antibodies could be too bulky, leads to interference with transducer. Thus in some embodiments, antibody fragments and mimitopes are used as capture ligands. By "epitope" herein is meant the actual site of antibody recognition of the antigen. The term is also used interchangeably with "antigenic determinant" or "antigenic determinant site". By "mimitopes" or "mimotope" herein is meant a peptide which has the spatial structure of a biologically important site, e.g., an epitope, or an enzyme active site, or a receptor binding site.

In some embodiments, the capture ligand comprises antibody alternatives, including but not limited to avimer. By "avimer" herein is meant proteins that are evolved from a large family of human extracellular receptor domains by in vitro exon shuffling and phage display. It is generally a multidomain protein with binding and inhibitory properties. See Silverman et al., Nature Biotechnology 23:1556-1561 (2005), herein incorporated by reference.

In some embodiments, the capture ligand comprises oligomeric peptides. These peptides can be obtained using techniques known in the art, including but not limited to phage display, Sidhu et al., Methods Enzymol., 328, 333-363 (2000), and one bead one peptide. For example, the peptide can be obtained using Biopanning Giodano et al., Nat. Med. 7:1249-53 (2001); herein incorporated by reference. The capture ligand may be nucleic acid, when the target analyte is a nucleic acid or nucleic acid binding proteins; alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly, there is a wide body of literature relating to the development of binding partners based on combinatorial chemistry methods. In this embodiment, when the capture ligand is a nucleic acid, preferred compositions and techniques are outlined in PCT US97/20014, hereby incorporated by reference.

In some embodiments, the capture ligand comprises an aptamer. By "aptamer" herein is meant a single-stranded, partially single-stranded, partially double-stranded or double-stranded nucleotide sequence, advantageously a replicatable nucleotide sequence, capable of specifically recognizing a selected non-oligonucleotide molecule or group of molecules by a mechanism other than Watson-Crick base pairing or triplex formation. Aptamers disclosed herein include, without limitation, defined sequence segments and sequences comprising nucleotides, ribonucleotides, deoxyribonucleotides, nucleotide analogs, modified nucleotides and nucleotides comprising backbone modifications, branch points and non-nucleotide residues, groups or bridges. Aptamers of the invention include partially and fully single-stranded and double-stranded nucleotide molecules and sequences, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the aptamer molecule or sequence. Aptamers can specifically bind to soluble, insoluble or immobilized selected molecules (e.g., ligands, receptors and effector molecules). Alternatively, the term "aptamer" includes nucleotides capable of shape-specific recognition of chemically bland surfaces by a mechanism distinctly different from specific binding. Aptamers of the instant invention may be selected to specifically recognize a structural shape or surface feature comprising a chemically bland surface (e.g., a silicon chip or carbon nanostructure) rather than the chemical identity of a selected target molecule (e.g., a ligand or receptor). An aptamer may be a molecule unto itself or a sequence segment comprising a nucleotide molecule or group of molecules, e.g., a defined sequence segment or aptameric sequence comprising a synthetic heteropolymer, multivalent heteropolymeric hybrid structure or aptameric multimolecular device.

In one embodiment, the soluble capture ligand comprises a peroxide generating system. As defined herein, the term "peroxide generating system" or "peroxide-generating system" means an enzyme that directly generates a peroxide from its enzyme substrate or an intermediary enzyme component that generates an intermediate, e.g., a cofactor or another enzyme substrate, for another enzyme that in turn generates a peroxide. In one example, a peroxide generating moiety may be an enzyme that generates peroxide. A wide variety of such enzymes are known, including glucose oxidase, acyl CoA oxidases, alcohol oxidases, aldehyde oxidases, etc. A wide variety of suitable oxidase enzymes are known in the art (see any glucose oxidase enzyme classified as EC 1.1.3.4, including, but not limited to, glucose oxidase, D-amino acid oxidase (DAAO) and choline oxidase). Glucose oxidase enzymes from a wide variety of organisms are well known, including bacterial, fungal and animal (including mammalian), including, but not limited to, *Aspergillus* species (e.g. *A. niger*), *Penicillum* species, *Streptomyces* species, mouse, etc.). Also of use are acyl CoA oxidases, classified as EC 1.3.3.6.

Alternatively, the peroxide generating system may include an intermediary enzyme component. For instance, the soluble capture ligand may contain an enzyme, such as alkaline phosphatase (AP), that catalyzes the generation of a necessary cofactor from a phosphorylated precursor for a soluble apo-oxidase enzyme (i.e. FADP converted to FAD which binds to apo-DAAO) which in turn generates peroxide by reaction with enzyme substrate. This strategy enables cascade amplification of target binding events if the concentrations of apo-enzyme, phosphorylated cofactor, and oxidase enzyme substrate are high with respect to the surface immobilized target.

In one embodiment, the peroxide generating system is peroxide-generating enzyme. Examples of the peroxide-generating enzyme include, but are not limited to glucose oxidase, glucose oxidase, acyl CoA oxidases, alcohol oxidases, aldehyde oxidases, D-amino acid oxidase (DAAO), choline oxidase, and acyl CoA oxidases.

In additional embodiment, the peroxide-generating system is an intermediary enzyme component of a peroxide generating system, such as alkaline phosphatase or any other phosphatase.

In one embodiment, the target analyte is ATP, and the peroxide generating moiety is glycerol-3-oxidase.

In another embodiment, the target analyte is NADH and the peroxide generating moiety is NADH oxidase (NAOX).

VI. Method of Making the Compositions of the Invention

As will be appreciated by those in the art, the compositions can be made using a variety of techniques known in the art. See for example the disclosures of U.S. Pat. Nos. 6,013,459, 6,248,229, 7,018,523, 7,267,939, U.S. patent application Ser. Nos. 09/096,593 and 60/980,733, and U.S. Provisional Application titled "Electrochemical Assay for the Detection of Enzymes" which is hereby incorporated herein by reference.

In one embodiment, the electrodes comprising a species including a functional group for the attachment of the capture ligand is used, and after the composition is made, a capture ligand with a complementary functional group is added, resulting in essentially spontaneous addition of the capture ligand to the surface. As will be appreciated by those in the art, there are a wide variety of functional groups/complementary functional groups that can be used. Suitable functional groups include, but are not limited to, maleimide, imidoesters, N-hydroxysuccinimidyls, alkyl halides, aryl halides, alpha-haloacyls and pryidyl disulfides. In general, the corresponding/complementary functional groups sulfhydryls, amines, amines, sulfhydryls, sulfhydryls, sulfhydryls and sulfhydryls, respectively. As will be appreciated by those in the art, it is also possible to switch the orientation of these functional groups, e.g. the sulfhydryl is present on the attachment linker and the maleimide is added to the biomolecule to be used as the capture ligand. As noted herein, the methods of attaching are dependent upon the reactive groups present on the two components. In an exemplary embodiment, the reactive functional group of the haptens of the invention and the functional group of the reactive part comprise electrophiles and nucleophiles that can generate a covalent linkage between them. Alternatively, the reactive functional group comprises a photoactivatable group, which becomes chemically reactive only after illumination with light of an appropriate wavelength. Typically, the conjugation reaction between the reactive functional group and the reactive partner results in one or more atoms of the reactive functional group or the reactive partner being incorporated into a new linkage attaching the two components. Selected examples of functional groups and linkages are shown in Table 1, where the reaction of an electrophilic group and a nucleophilic group yields a covalent linkage.

TABLE 1

Examples of some routes to useful covalent linkages with electrophile and nucleophile reactive groups:

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—$OC_4H_4O_2$) oxysulfosuccinimidyl (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates.

The functional groups and complementary functional groups can also include linkers, for flexibility or steric rigidity as the case may be, or other reasons.

It should be noted that while the figures depict the presence of a functional group and the complementary functional group, in some cases the addition results in the loss of atoms from these groups, and thus this is not meant to depict a situation when the entire functional group and complementary functional group is present in the final composition.

In addition, the figures depict the use of "monofunctional" linkers, e.g. a maleimide. It is also possible to include additional steps that utilize either homo- or heterobifunctional groups, (see 1994 Pierce Chemical Company catalog, technical section on cross linkers, pages 155-200, incorporated herein by reference). For example, an attachment linker comprising a sulfur atom on one terminus and an amino group on the other end could be reacted with a bifunctional linker that reacts with amines, and then subsequently a capture ligand comprising an amino group can be added.

In another embodiment, the compositions of the invention are made by synthesizing each component and adding them to the electrode, generally simultaneously. That is, in one embodiment, the REAMC comprising the attachment linker (with the attachment functional moiety such as a sulfur atom), the ligands, the transition metal and the binding ligand is made, and added (optionally with a SAM forming species) to the electrode. Similarly, a two or three component system is done in FIG. 1B, with a first species comprising the EAM with the attachment linker and attachment functional group, a second species comprising an attachment linker with the capture ligand, and the optional third species of a SAM forming species, which are added, against generally simultaneously, to the electrode. In some cases, the components can be added sequentially, and in some cases, a post synthesis step done of adding extra SAM forming species (and/or other components) with optional heating can be done to ensure good packing on the electrode.

The compositions of the present invention may be used in a variety of research, clinical, quality control, or field testing settings. The examples provided herein are for illustration purposes only and are in no means to limit the scope the present invention. Further, all references cited herein are incorporated by reference for all the relevant contents therein.

VII. Method of Using the Composition of the Invention

A. Target Analyte and Sample

In one aspect, the present invention provides methods and compositions useful in the detection of target analytes. By "target analyte" or "analyte" or grammatical equivalents herein is meant any molecule or compound to be detected and that can bind to a binding species, e.g. a capture ligand, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs; cells; antibodies; antigens; cellular membrane antigens and receptors (neural, hormonal, nutrient, and cell surface receptors) or their ligands.

In some embodiments, the target analyte is cytochrome P450, avidinistreptavdin, SEB, PSA- (protease), tryprinichymotrypin (protease), anthrax spore and E. coli. O157:H7.

In some embodiments, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a capture ligand, it may be desirable to utilize protein analogs to retard degradation by sample contaminants. Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antiepileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppressants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *G. lamblia* Y. pestis, *Pseudomonas*, e.g. *P. aeruginosa*, *P. putida*; *Chlamydia*, e.g. *C. trachomatis*; *Bordetella*, e.g. *B. pertussis*; *Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), leutinizing hormone (LH), progesterone, testosterone, and (4) other proteins (including α-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly. Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242). As will be appreciated by those in the art, a large number of analytes may be detected using the present methods; basically, any target analyte for which a binding ligand, described below, may be made may be detected using the methods of the invention.

In some embodiments, the target analyte is a protein related to MRSA. Methicillin-resistant *Staphylococcus aureus* (MRSA) (also be referred to as multiple-resistant *Staphylococcus aureus* or oxacillin-resistant *Staphylococcus aureus* (ORSA)) is responsible for difficult-to-treat infections in humans. MRSA is a strain of *Staphylococcus aureus* that is resistant to a large group of antibiotics called the beta-lactams, which include the penicillins and the cephalosporins. The organism is often sub-categorized as Community-Associated MRSA (CA-MRSA) or Health Care-Associated MRSA (HA-MRSA) although this distinction is complex. Some have defined CA-MRSA by criteria related to patients suffering from an MRSA infection while other authors have defined CA-MRSA by genetic characteristics of the bacteria themselves. CA-MRSA strains were first reported in the late 1990s; these cases were defined by a lack of exposure to the health care setting. In the next several years, it became clear that CA-MRSA infections were caused by strains of MRSA that differed from the older and better studied healthcare-associated strains. The new CA-MRSA strains have rapidly spread in the United States to become the most common cause of cultured skin infections among individuals seeking medical care for these infections at emergency rooms in cities. These strains also commonly cause skin infections in athletes, jail and prison detainees, soldiers, Native Alaskans and Native Americans, and children in the inner city. MRSA is a resistant variation of the common bacterium *Staphylococcus aureus*. It has evolved an ability to survive treatment with beta-lactamase resistant beta-lactam antibiotics, including methicillin, dicloxacillin, nafcillin, and oxacillin. MRSA is especially troublesome in hospital-associated (nosocomial) infections. In hospitals, patients with open wounds, invasive devices, and weakened immune systems are at greater risk for infection than the general public. Hospital staff who do not follow proper sanitary procedures may transfer bacteria from patient to patient. Visitors to patients with MRSA infections or MRSA colonization are advised to follow hospital isolation protocol by using the provided gloves, gowns, and masks if indicated. Visitors who do not follow such protocols are capable of spreading the bacteria to cafeterias, bathrooms, and elevators.

In some embodiment, the MRSA related protein is penicillin binding protein 2a (PBP2a). PBP2' is a protein coded by the mecA gene and is present in the membranes of methicillin resistant *Staphylococcus aureus* and coagulase-negative staphylococci. The preparation of PBP2' can be carried out using methods known in the art, such as the protocol described in the MRSA Latex Test for PBP2′ kit distributed by Hardy Diagnostics (Santa Maria, Calif.).

In some embodiments, the target is the PBP2a protein of MRSA, and the capture ligand is a moiety that is capable of binding to PBP2a. By "nucleic acid" or "oligonucleotide" or grammatical equivalents herein is meant at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments. As will be appreciated by those in the art, all of these nucleic acid analogs may find use in the present invention. In addition, mixtures of naturally occurring nucleic acids and analogs can be made; for example, at the site of conductive oligomer or EAM attachment, an analog structure may be used. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

In some embodiments, nucleic acid target analytes are not preferred.

In general, a sample is added to the compositions of the invention. In one aspect, the present invention provides a method of detecting a target enzyme in a sample. By "sample" or "test sample" herein is meant a composition that contains the analyte or analytes to be detected. The sample can be heterogeneous, containing a variety of components, i.e. different proteins. Alternatively, the sample can be homogenous, containing one component. The sample can be naturally occurring, a biological material, or man-made material. The material can be in a native or denatured form. The sample can be a single cell or a plurality of cells, a blood sample, a tissue sample, a skin sample, a urine sample, a water sample, or a soil sample. In some embodiments, the sample comprises the contents of a single cell, or the contents of a plurality of cells. The sample can be from a living organism, such as a eukaryote, prokaryote, mammal, human, yeast, or bacterium, or the sample can be from a virus. The samples can be used without any treatment, or with treatment if desired.

In some embodiments, the target analyte, contained within a test sample, is added to the compositions of the invention, under conditions that if present, the target analyte binds to the capture binding ligand. These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. As will be appreciated by those in the art, a large number of analytes may be detected using the present methods; basically, any target analyte for which a capture ligand, described below, may be made may be detected using the methods of the invention.

In addition, those in the art will appreciate that it is also possible to use the compositions of the invention in assays that rely on a loss of signal. For example, a first measurement is taken when the redox active molecule is inhibited, and then the system is changed as a result of the introduction of a target analyte, causing the solvent inhibited molecule to become solvent accessible, resulting in a loss of signal. This may be done in several ways, as will be appreciated by those in the art.

In some embodiments, a first measurement is taken when the target analyte is present. The target analyte is then removed, for example by the use of high salt concentrations or thermal conditions, and then a second measurement is taken. The quantification of the loss of the signal can serve as the basis of the assay. Alternatively, the target analyte may be an enzyme. In this embodiment, the redox active molecule is made solvent inhibited by the presence of an enzyme substrate or analog, preferably, but not required to be covalently attached to the redox active molecule, preferably as one or more ligands. Upon introduction of the target enzyme, the enzyme associates with the substrate to cleave or otherwise sterically alter the substrate such that the redox active molecule is made solvent accessible. This change can then be detected. This embodiment is advantageous in that it results in an amplification of the signal, since a single enzyme molecule can result in multiple solvent accessible molecules. This may find particular use in the detection of bacteria or other pathogens that secrete enzymes, particularly scavenger proteases or carbohydrases.

In some embodiments, the target analyte is a protease. Proteases are classified into six groups: serine proteases, threonine proteases, cysteine proteases, aspartic acid proteases, metalloproteases, and glutamic acid proteases. In general, protease can either break specific peptide bonds (e.g. specific segments for limited proteolysis), depending on the amino acid sequence of a protein, or break down a complete protein to amino acids (unlimited proteolysis). The activity can be a destructive change, abolishing a protein's function or digesting it to its principal components; it can be an activation of a function, or it can be a signal in a signaling pathway.

In some embodiments, the target enzyme is an endopeptidase. By "endopeptidase" herein is meant peptidases that break peptide bonds within a protein substrate, in contrast to exopeptidases, which break peptide bonds from one or both termini of the protein substrate. Endopeptidases are divided into subclasses on the basis of catalytic mechanism: the serine endopeptidases, cysteine endopeptidases, aspartic endopeptidases, metalloendopeptidases, and other endopeptidases.

(1) Serine Endopeptidases

This class comprises two distinct families. The chymotrypsin family which includes the mammalian enzymes such as chymotrypsin, trypsin or elastase or kallikrein and the substilisin family which include the bacterial enzymes such as subtilisin. The general three dimensional (3D) structure is different in the two families but they have the same active site geometry and the catalysis proceeds via the same mechanism. The serine endopeptidases exhibit different substrate specificities which are related to amino acid substitutions in the various enzyme subsites interacting with the substrate residues. Some enzymes have an extended interaction site with the substrate whereas others have a specificity restricted to the P1 substrate residue.

(2) Cysteine Endopeptidases

This family includes the plant proteases such as papain, actinidin or bromelain, several mammalian cathepsins, including lysosomal cathepsins and cathepsin B, L, S, H, J, N and O; the cytosolic calpains (calcium-activated) as well as several parasitic proteases (e.g., *Trypanosoma, Schistosoma*) and caspases, including interleukin converting enzyme (ICE).

(3) Aspartic Endopeptidases

Most of aspartic endopeptidases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral endopeptidases such as the protease from the AIDS virus (HIV) also called retropepsin.

In contrast to serine and cysteine proteases, catalysis by aspartic endopeptidases do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage.

(4) Metallo Endopeptidases

The metallo endopeptidases are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Of particular interest are metalloenzymes including adenosine deaminase, angiotensin converting enzyme, calcineurin, metallo-beta-lactamase, PDE3, PDE4, PDE5, renal dipeptidase, and urease.

In one embodiment, the metallo endopeptidase is a matrix metalloproteinase, including MMP-1 through MMP-10, particularly MMP-1, MMP-2, MMP-7 and MMP-9.

(5) Bacterial/Toxin Endopeptidases

Toxin endopeptidases, usually of bacterial origin, can have a devastating and sometime lethal impact on host organisms. Some of the better known bacterial endopeptidase toxins are listed below in Table 2.

TABLE 2

Bacterial Endopeptidases

| Organism/Toxin | Mode of Action | Target (Cleavage Site) | Disease |
|---|---|---|---|
| *B. anthracis*/lethal factor | Metalloprotease | MAPKK1/MAPKK2 (multiple) | Anthrax |
| *C. botulinum*/neurotxin A | Zinc-metalloprotease | SNAP-25 (ANQ/RAT) | Botulism |
| *C. botulinum*/neurotxin B | Zinc-metalloprotease | VAMP/synaptobrevin (ASQ/FET) | Botulism |
| *C. botulinum*/neurotxin C | Zinc-metalloprotease | Syntaxin (TKK/AVK) | Botulism |
| *C. botulinum*/neurotxin D | Zinc-metalloprotease | VAMP/synaptobrevin (DQK/LSE) | Botulism |

TABLE 2-continued

Bacterial Endopeptidases

| Organism/Toxin | Mode of Action | Target (Cleavage Site) | Disease |
|---|---|---|---|
| C. botulinum/neurotxin E | Zinc-metalloprotease | SNAP-25 (IDR/IME) | Botulism |
| C. botulinum/neurotxin F | Zinc-metalloprotease | VAMP/synaptobrevin | Botulism |
| C. botulinum/neurotxin G | Zinc-metalloprotease | VAMP/synaptobrevin (TSA/AKL) | Botulism |
| Yersinia virulence factor YopJ | Cysteine protease | Unknown | |
| Yersinia virulence factor YopT | Cysteine protease | Prenylated cysteine | |
| Salmonella virulence factor AvrA | Unknown | Unknown | Salmonellosis |
| Clostridium tetani/ tetanus toxin | Zinc-metalloprotease | VAMP/synaptobrevin (ASQ/FET) | Tetanus |

The *C. botulinum* neurotoxins (BoNTs, serotypes A-G) and the *C. tetani* tetanus neurotoxin (TeNT) are two examples of bacterial toxins that are endopeptidases. BoNTs are most commonly associated with infant and food-borne botulism and exist in nature as large complexes comprised of the neurotoxin and one or more associated proteins believed to provide protection and stability to the toxin molecule while in the gut. TeNT, which is synthesized from vegetative *C. tetani* in wounds, does not appear to form complexes with any other protein components.

BoNTs are highly specific, zinc-dependent endoproteases that specifically cleave small proteins which control the docking of synaptic vesicles with the neural synaptic membrane. BoNT A and BoNT E specifically cleave the 25-kD synaptosomal-associated protein (SNAP-25) with BoNT A cleaves between residues Q197 and R198. SNAP-25 is a presynaptic plasma membrane protein involved in the regulation of neurotransmitter release. Two alternative transcript variants encoding different protein isoforms have been described for this gene in human, SNAP25A (GenBank Accession No. NP_003072) and SNAP25B (GenBank Accession No. NP_570824). BoNT C cleaves the membrane protein syntaxin and SNAP-25. BoNT B, D, F and G are specific for the intracellular vesicle-associated membrane-associated protein (VAMP, also termed synaptobrevin). See Schiavo et al., JBC 266:23784-87 (1995); Schiavo et al., FEBS Letters 335:99-103 (1993), herein are incorporated by reference in their entireties.

Several in vitro assays have been developed based on the cleavage of immobilized synthetic peptide substrates. Halls et al., J Clin Microbiol 34:1934-8 (1996); Witcome et al., Appl Environ Microbiol 65:3787-92 (1999), and Anne et al., Ana Biochem 291:253-61 (2001).

The BoNTs and TeNT are either plasmid encoded (TeNT, BoNTs/A, G, and possibly B) or bacteriophage encoded (BoNTs/C, D, E, F), and the neurotoxins are synthesized as inactive polypeptides of 150 kDa. BoNTs and TeNT are released from lysed bacterial cells and then activated by the proteolytic cleavage of an exposed loop in the neurotoxin polypeptide. Each active neurotoxin molecule consists of a heavy (100 kDa) and light chain (50 kDa) linked by a single interchain disulphide bond. The heavy chains of both the BoNTs and TeNT contain two domains: a region necessary for toxin translocation located in the N-terminal half of the molecule, and a cell-binding domain located within the C-terminus of the heavy chain. The light chains of both the BoNTs and TeNT contain zinc-binding motifs required for the zinc-dependent protease activities of the molecules.

The cellular targets of the BoNTs and TeNT are a group of proteins required for docking and fusion of synaptic vesicles to presynaptic plasma membranes and therefore essential for the release of neurotransmitters. The BoNTs bind to receptors on the presynaptic membrane of motor neurons associated with the peripheral nervous system. Proteolysis of target proteins in these neurons inhibits the release of acetylcholine, thereby preventing muscle contraction. BoNTs/B, D, F, and G cleave the vesicle-associated membrane protein and synaptobrevin, BoNT/A and E target the synaptosomal-associated protein SNAP-25, and BoNT/C hydrolyzes syntaxin and SNAP-25. TeNT affects the central nervous system and does so by entering two types of neurons. TeNT initially binds to receptors on the presynaptic membrane of motor neurons but then migrates by retrograde vesicular transport to the spinal cord, where the neurotoxin can enter inhibitory interneurons. Cleavage of the vesicle-associated membrane protein and synaptobrevin in these neurons disrupts the release of glycine and gamma-amino-butyric acid, which, in turn, induces muscle contraction. The contrasting clinical manifestations of BoNT or TeNT intoxication (flaccid and spastic paralysis, respectively) are the direct result of the specific neurons affected and the type of neurotransmitters blocked.

Of particular interest is BoNT/LC (serotype C), and specifically BoNTC/LC (as compared to other LC serotypes). First, BoNTC/LC poses a particularly significant bioterror threat because it has a long half-life inside human neuronal cells. Second, an in vitro assay for BoNTC/LC does not currently exist, probably because this LC protease appears to require membranes to function. In the neuronal cell environment, BoNTC/LC cleaves syntaxin, a membrane protein required for synaptic vesicle fusion to the presynaptic membrane.

Other examples include the *Yersinia* virulence factors YopJ and YopT, as well as *Salmonella* AvrA. Other target analytes include, but are not limited to: coagulation factor levels (hemorrhagic or thrombotic conditions), fecal elastase (exocrine activity of the pancreas, e.g. in cystic fibrosis or chronic pancreatitis), PSA, VEGF and EGFR (tumor response in rectal cancer), MMP-9 (tumor marker of esophageal cancer and early stroke marker), MMP-13 (early stroke marker), cathepsin B (cancer), cathepsin G (emphysema, rheumatoid arthritis, inflammation), plasminogen activator (thrombosis, chronic inflammation, cancer), urokinase (cancer).

In some embodiments the target analyte is troponin (cardiac troponin I and T). Troponin is a complex of three regulatory proteins that is integral to muscle contraction in skeletal and cardiac muscle, but not smooth muscle. Troponin is found in both skeletal muscle and cardiac muscle, but the specific versions of troponin differ between types of muscle. Two subtypes of troponin (cardiac troponin I and T) are very sensitive and specific indicators of damage to the heart muscle (myocardium). They are measured in the blood to differentiate between unstable angina and myocardial infarction (heart attack) in patients with chest pain. A patient who had suffered from a myocardial infarction would have an area of damaged heart muscle and so would have elevated cardiac troponin levels in the blood. Similarly, another embodiment utilizes competition-type assays. In this embodiment, the binding ligand is the same as the actual molecule for which detection is desired; that is, the binding ligand is actually the target analyte or an analog. A binding partner of the binding ligand is added to the surface, such that the redox active molecule becomes solvent inhibited, electron transfer occurs and a signal is generated. Then the actual test sample, containing the same or similar target analyte which is bound to the electrode, is added. The test sample analyte will compete for the binding partner, causing the loss of the binding partner on the surface and a resulting decrease in the signal. A similar embodiment utilizes a target analyte (or analog) is covalently attached to a preferably larger moiety (a "blocking moiety"). The analyte-blocking moiety complex is bound to a binding ligand that binds the target analyte, serving to render the redox active molecule solvent inhibited. The introduction of the test sample target analyte serves to compete for the analyte-blocking moiety complex, releasing the larger complex and resulting in a more solvent accessible molecule. The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In one embodiment, the method is used for the determination of glycated proteins as a fraction of the total protein. The methods are exemplified by a particular embodiment, the single-measurement detection of the ratio of glycated hemoglobin (e.g. hemoglobin A1C) to total hemoglobin. However, the exemplified method can be expanded to apply to a wide range of glycated serum proteins (e.g., Fructosamine) or glycated albumin, all three used as possible diabetic markers. It can, however, be also expanded to include all other possible glycated proteins, such as, albumins, immunoglobulins, lipoproteins, fibrinogens, regulatory proteins and clotting factors. In more detail these proteins could include, alpha2-macroglobulin, other globulins, which are of three types—alpha, beta and gamma, alpha anti-trypsins Transferrin, Prothrombin, MBL or MBP, Prealbuminm Alpha 1 antitrypsin, Alpha 1 acid glycoprotein, Alpha 1 fetoprotein, Haptoglobin, Alpha 2 macroglobulin, Ceruloplasmin, Transferring C3/C4 Beta 2 microglobulin, Beta lipoprotein, Gamma globulin proteins, C-reactive protein (CRP).

In other embodiments, the methods as described above are those where the protein is hemoglobin and the glycated protein is glycated hemoglobin. In another embodiment, the protein is hemoglobin and the glycated protein is hemoglobin A1c. In yet another embodiment, the glycated protein is glycated serum protein, fructosamine and glycated albumin.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands. The apparatus further comprises a voltage source electrically connected to the test chamber; that is, to the measuring electrodes. Preferably, the voltage source is capable of delivering AC and DC voltages, if needed.

In an embodiment, the apparatus further comprises a processor capable of comparing the input signal and the output signal. The processor is coupled to the electrodes and configured to receive an output signal, and thus detect the presence of the target analyte.

B. Initiation

In one aspect, the present invention provides methods of detecting target analyte. The target analyte, contained within a test sample, is added to the electrode containing either a solvent accessible redox active complex or a mixture of solvent accessible redox active molecules and capture ligands, under conditions that if present, the target analyte will bind to the capture ligand. These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In some embodiments, the target analyte will bind the capture ligand reversibly, i.e. non-covalently, such as in protein-protein interactions of antigens-antibodies, enzyme-substrate (or some inhibitors) or receptor-ligand interactions.

In a preferred embodiment, the target analyte will bind the binding ligand irreversibly, for example covalently. For example, some enzyme-inhibitor interactions are considered irreversible. Alternatively, the analyte initially binds reversibly, with subsequent manipulation of the system which results in covalent attachment. For example, chemical cross-linking after binding may be done, as will be appreciated by those in the art. For example, peptides may be cross-linked using a variety of bifunctional agents, such as maleimidobenzoic acid, methyldithioacetic acid, mercaptobenzoic acid, S-pyridyl dithiopropionate, etc. Alternatively, functionally reactive groups on the target analyte and the binding ligand may be induced to form covalent attachments. Upon binding of the analyte to the binding moiety, the solvent accessible redox active molecule becomes solvent inhibited. By "solvent inhibited redox active molecule" herein is meant the solvent reorganization energy of the solvent inhibited redox active molecule is less than the solvent reorganization energy of the solvent accessible redox active molecule. As noted above, this may occur in several ways. In some embodiments, the target analyte provides a coordination atom, such that the solvent accessible redox active molecule loses at least one, and preferably several, of its small polar ligands. Alternatively, in some embodiments, the proximity of the target analyte to the redox active molecule does not result in ligand exchange, but rather excludes solvent from the area surrounding the metal ion (i.e. the first or second coordination sphere) thus effectively lowering the required solvent reorganization energy.

In some embodiments, the required solvent reorganization energy decreases sufficiently to result in a decrease in the $E^o$ of the redox active molecule by at about 100 mV, with at least about 200 mV being preferred, and at least about 300-500 mV being particularly preferred.

In some embodiments, the required solvent reorganization energy decreases by at least 100 mV, with at least about 200 mV being preferred, and at least about 300-500 mV being particularly preferred.

In some embodiments, the required solvent reorganization energy decreases sufficiently to result in a rate change of electron transfer (kET) between the solvent inhibited redox active molecule and the electrode relative to the rate of electron transfer between the solvent accessible redox active molecule and the electrode. In a embodiment, this rate change is greater than about a factor of 3, with at least about a factor of 10 being preferred and at least about a factor of 100 or more being particularly preferred. The determination of solvent reorganization energy will be done as is appreciated by those in the art. Briefly, as outlined in Marcus theory, the electron transfer rates (kET) are determined at a number of different driving forces (or free energy, $-\Delta G°$); the point at which the rate equals the free energy is the $\lambda$. This may be treated in most cases as the equivalent of the solvent reorganization energy; see Gray et al. Ann. Rev. Biochem. 65:537 (1996), hereby incorporated by reference. The solvent inhibited redox active molecule, indicating the presence of a target analyte, is detected by initiating electron transfer and detecting a signal characteristic of electron transfer between the solvent inhibited redox active molecule and the electrode. Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used. Preferably, initiation and detection is chosen to maximize the relative difference between the solvent reorganization energies of the solvent accessible and solvent inhibited redox active molecules.

C. Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock-in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte. The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capacitance) could be used to monitor electron transfer between the redox active molecules and the electrode. Finally, any system that generates a current (such as electron transfer) also generates a small magnetic field, which may be monitored in some embodiments.

In some embodiments, the system may be calibrated to determine the amount of solvent accessible redox active molecules on an electrode by running the system in organic solvent prior to the addition of target. This is quite significant to serve as an internal control of the sensor or system. This allows a preliminary measurement, prior to the addition of target, on the same molecules that will be used for detection, rather than rely on a similar but different control system. Thus, the actual molecules that will be used for the detection can be quantified prior to any experiment. Running the system in the absence of water, i.e. in organic solvent such as acetonitrile, will exclude the water and substantially negate any solvent reorganization effects. This will allow a quantification of the actual number of molecules that are on the surface of the electrode. The sample can then be added, an output signal determined, and the ratio of bound/unbound molecules determined. This is a significant advantage over prior methods. It should be understood that one benefit of the fast rates of electron transfer observed in the compositions of the invention is that time resolution can greatly enhance the signal-to-noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, orders of magnitude improvements in signal-to-noise may be achieved. Without being bound by theory, it appears that target analytes, bound to an electrode, may respond in a manner similar to a resistor and capacitor in series. Also, the $E^0$ of the redox active molecule can shift as a result of the target analyte binding. Furthermore, it may be possible to distinguish between solvent accessible and solvent inhibited redox active molecules on the basis of the rate of electron transfer, which in turn can be exploited in a number of ways for detection of the target analyte. Thus, as will be appreciated by those in the art, any number of initiation-detection systems can be used in the present invention.

In some embodiments, electron transfer is initiated and detected using direct current (DC) techniques. As noted above, the $E^0$ of the redox active molecule can shift as a result of the change in the solvent reorganization energy upon target analyte binding. Thus, measurements taken at the $E^0$ of the solvent accessible redox active molecule and at the $E^0$ of the solvent inhibited molecule will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to distinguish between solvent accessible and solvent inhibited redox active molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

D. Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

E. Apparatus

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In an embodiment, the apparatus further comprises a processor capable of comparing the input signal and the output signal. The processor is coupled to the electrodes and configured to receive an output signal, and thus detect the presence of the target analyte.

CHEMICAL DEFINITIONS

The following terms and expressions used herein have the indicated meanings

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

EXAMPLES

Example 1

Synthesis of Compounds 200-206

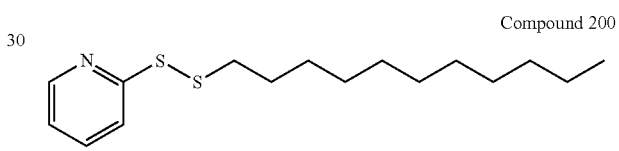

Compound 200

To a 100 mL round bottom flask was added 1-undecanethiol (1.4973 g, 7.95 mmol) and dry methanol (30 mL). Dry dichloromethane (5 mL) was added to aid in dissolution. 2,2-dithiodipyridine (1.7547 g, 7.96 mmol) was added as a powder followed by triethylamine (1.15 mL, 8.27 mmol). The reaction mixture was deoxygenated with argon then set to stir at room temperature under a positive pressure of argon for 24 hours. The reaction contents were dried on a rotary evaporator and purified by silica gel column chromatography as the eluent to yield compound 200 (1.8494 g, 78%).

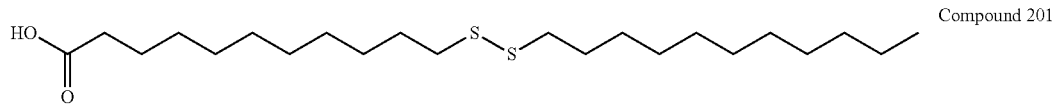 [SMILES: CCCCCCCCCCCSSCCCCCCCCCCC(=O)O]

Compound 201

To a 100 mL Schlenk flask was added 200 (1.8528 g, 6.23 mmol) with dry tetrahydrofuran (30 mL). 1-mercaptoudecanoic acid (1.5108 g, 6.92 mmol) and 4-dimethylaminopyridine (0.7710 g, 6.31 mmol) were added as solids to the reaction flask then additional tetrahydrofuran (20 mL). The reaction contents were deoxygenated with argon then set to stir at room temperature under a positive pressure of argon for 16 hours. The reaction contents were dried on a rotary evaporator and purified by silica gel column chromatography to yield compound 201 (1.0207 g, 40%).

Compound 202

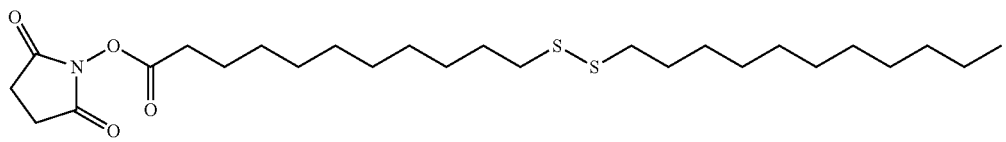

To a 250 mL round bottom flask was added N-hydroxysuccinimide (0.1435 g, 1.25 mmol) with dry dichloromethane (100 mL). The contents were briefly placed in a sonication bath to aid in dissolution then compound 201 (0.5078 g, 1.25 mmol) was added at once as a dichloromethane solution (10 mL). A dichloromethane solution (10 mL) of dicyclohexylcarbodiimide (0.2876 g, 1.39 mmol) was added drop wise over 23 min., followed by deoxygenation with bubbling argon for 30 min. The contents were set to stir at room temperature under a positive pressure of argon for 17 hours. The reaction contents were filtered to remove the dicyclohexylurea precipitate, concentrated on a rotary evaporator to 20-25 mL, then purified by silica gel column chromatography to provide compound 202 (0.3892 g, 62%).

Compound 203

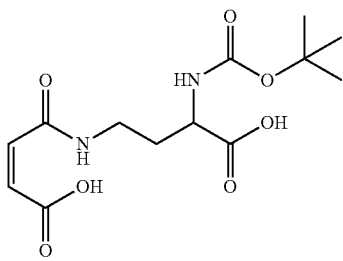

To a 25 mL round bottom flask was added Boc-D-2,4-diaminobutyric acid (0.3080 g, 1.41 mmol) and maleic anhydride (0.1415 g, 1.44 mmol) with glacial acetic acid (8 mL). The reaction contents were set to stir at room temperature under a positive pressure of argon for 4.5 hours. The reaction contents were dried on a vacuum line to remove all volatiles to yield compound 203 (0.4490 g). The material was used as-is without further purification; estimated purity is 65% based on $^1$H NMR data.

Compound 204

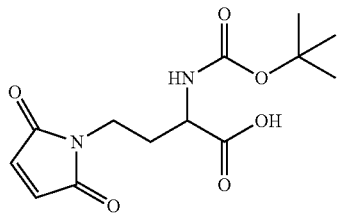

To a 100 mL Schlenk flask was added 203 (0.2919 g, 0.92 mmol) with dry toluene (40 mL) and triethylamine (400 μL, 2.89 mmol). The flask was fitted with a Dean-Stark apparatus and the side arm filled with dry toluene. The entire setup was flushed with argon and the flask brought to a vigorous reflux for 4.5 hours. The reaction contents were dried on a rotary evaporator to provide a tan/brownish oil. This oil was dissolved in water (20 mL) and acidified with citric acid (50 mL aqueous). Extraction of the crude product was accomplished with dichloromethane/methanol (9:1). The organic solution was concentrated on a rotary evaporator then purified by silica gel column chromatography to provide compound 204 (0.2647 g, 96%).

Compound 205

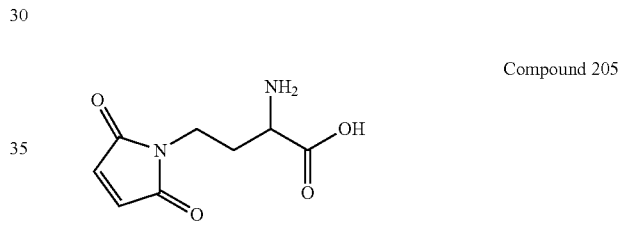

To a 25 mL round bottom flask was added HCl (10 mL of 4M in dioxane; 40 mmol) under argon. The contents were cooled in an ice water bath then transferred to a pre-cooled 25 mL round bottom flask containing compound 204. The contents were stirred at 0° C. under argon for 45 min. then warmed to room temperature and stirred for an additional 2 hours. All solvent and excess HCl was removed on a vacuum line and the crude residue passed through a Dowex 1×2-100 anion exchange resin using water as the eluent to provide compound 205 (0.2004 g, 98%).

Compound 206

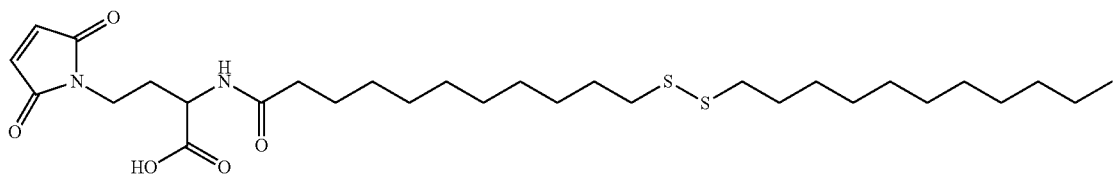

To a 50 mL Schlenk flask was added 202 (0.0220 g, 0.044 mmol) and dry acetonitrile (6 mL). 203 (0.0105 g, 0.045 mmol) and diisopropylethylamine (8.5 µL, 0.049 mmol) were added in sequence and the heterogeneous contents set to stir under argon at room temperature. After 30 min. additional diisopropylethylamine (8.5 µL, 0.049 mmol) was added to the reaction mixture to aid in the dissolution of 203. Dimethylacetamide (1.5 mL) was added drop wise to provide a homogeneous solution; the contents were flushed with argon and set to stir at room temperature for 17 hours. The reaction contents were pumped to dryness on a vacuum line then dissolved in dichloromethane and washed with aqueous citric acid. Extraction with dichloromethane (4×20 mL), followed by silica gel column chromatography yielded compound 206 (0.0114 g, 45%).

Example 2

1,3-Disubstituted Ferrocene EAMs

A series of 1,3-disubstituted ferrocene derivatives (1-4) were synthesized with different functional moieties and organosulfur anchoring groups for SAM formation on gold (FIG. 12).

Figure 18:
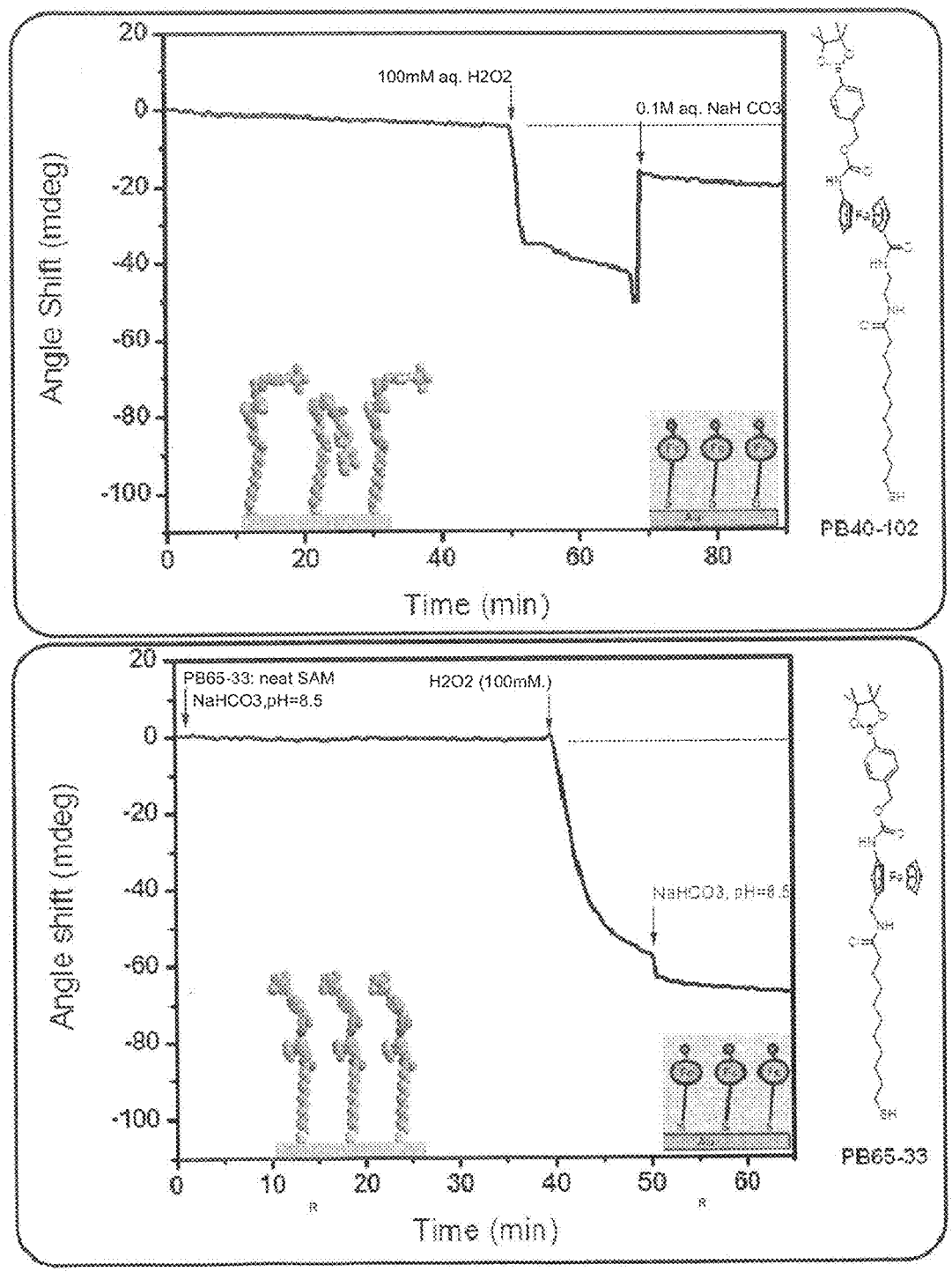
FIG. 18 shows SPR sensorgrams for neat SAMs of 2 (bottom) and 5 (top) monitored in real-time before and after exposure to hydrogen peroxide (0.1M) and washing. Data from both plots were collected in difference mode and normalized to the response from background buffer.

To compare functional group reactivity at the solution/SAM interface between 1,3-disubstituted ferrocenes and similarly functionalized 1,1'-disubstituted regioisomers, neat monolayers of 2 and 5 were prepared on gold slides. Both compounds contain carbamate-linked benzylboronate esters as amine protecting groups. Upon boronate oxidation with hydrogen peroxide and subsequent alkaline hydrolysis, these functional groups undergo a programmed disassembly (see, Lo, L.-C.; Chu, C.-Y. Chem. Commun. 2003, 2728-2729) to liberate quinone methide and carbon dioxide converting the carbamate nitrogen to a primary amine (i.e. $2+H_2O_2 \rightarrow 3$). Thus, if boronate ester groups in SAMs of 2 and 5 are equally displayed at the solution/SAM interface, exposure to hydrogen peroxide will remove these protecting groups (MW=262) resulting in a similar change in film thickness for each SAM that can be monitored by surface plasmon resonance (SPR). Reducing the molecular weight of components bound to gold results in a negative shift in SPR angle. FIG. 18 shows real-time SPR sensorgrams for SAMs of 2 (A) and 5 (B) before and after exposure to hydrogen peroxide (0.1M). After washing, the change in resonance angle observed for 2 is −70 mdeg after 10 min with peroxide. In contrast, the SAM of 5 only experiences a −20 mdeg change after a 20 min reaction and

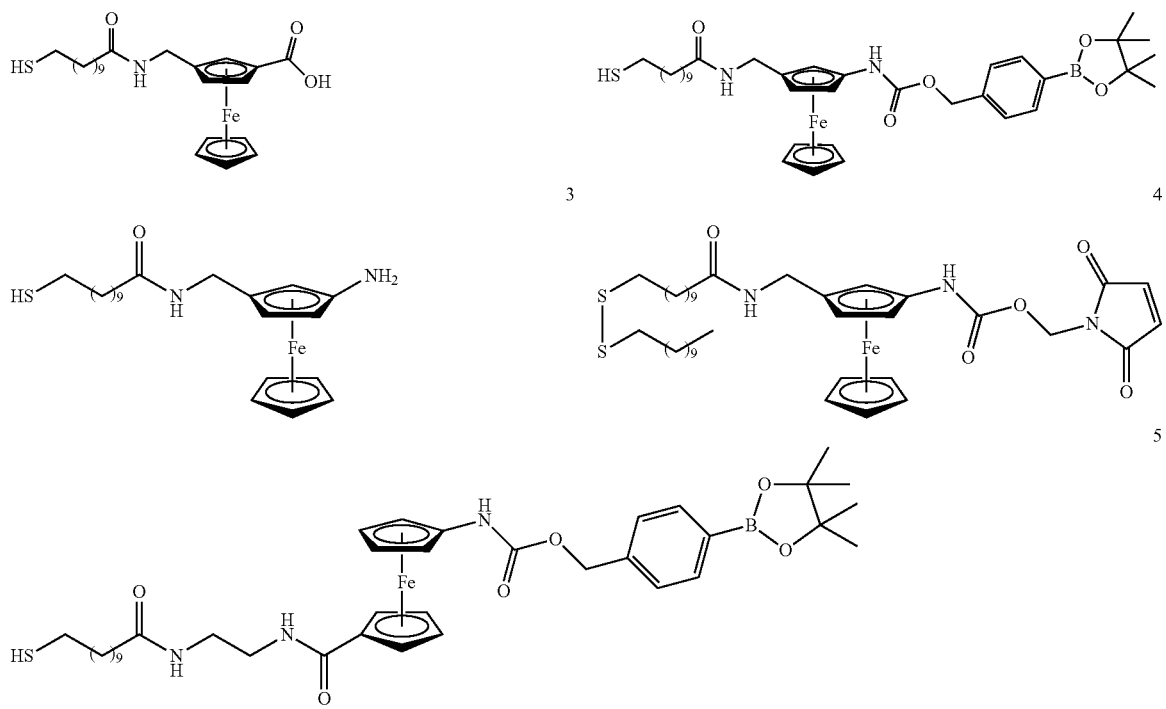

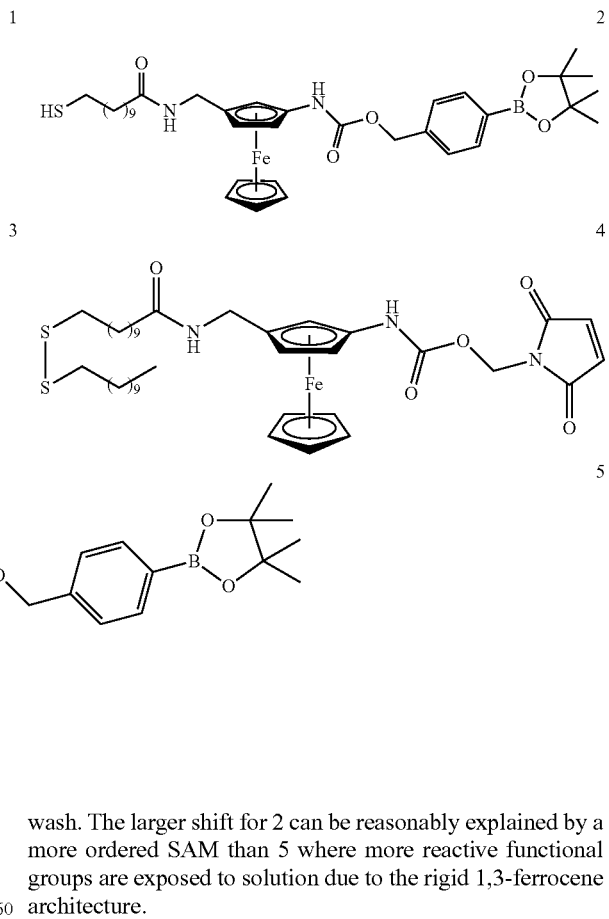

Figure 13:
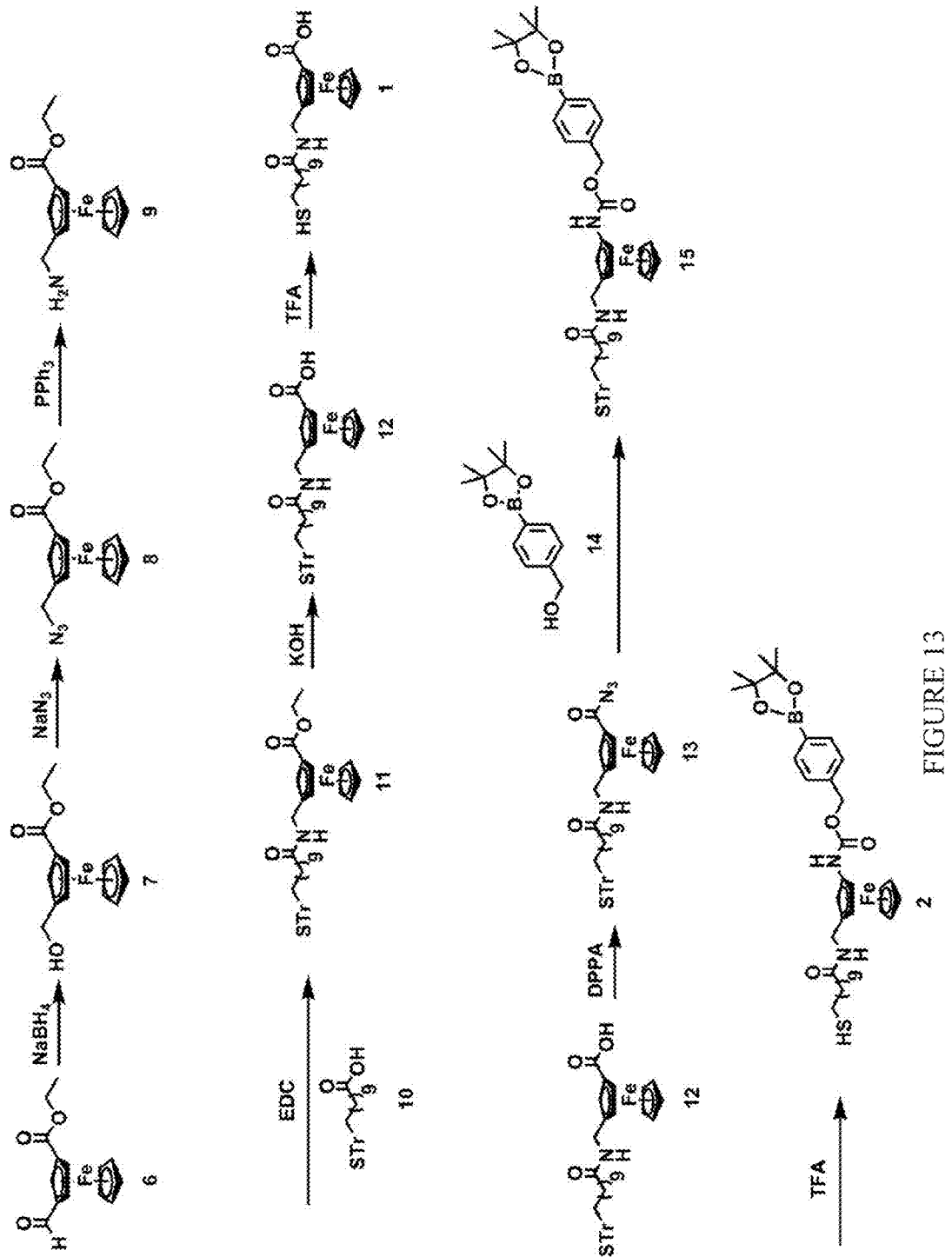
FIG. 13 shows a representative synthetic scheme for compounds 1 and 2.
Figure 14:
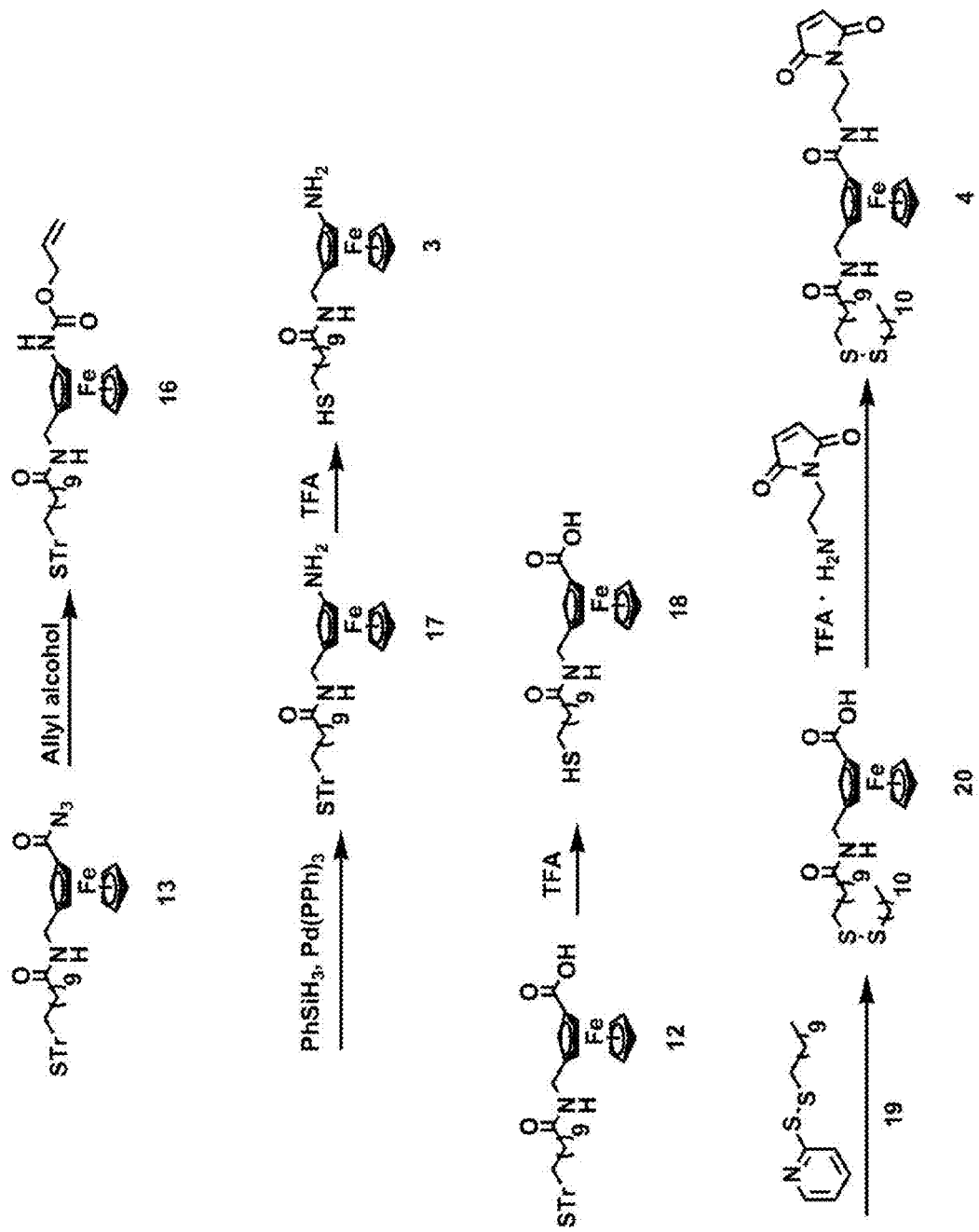
FIG. 14 shows a representative synthetic scheme for compounds 3 and 4.
Figure 19A:
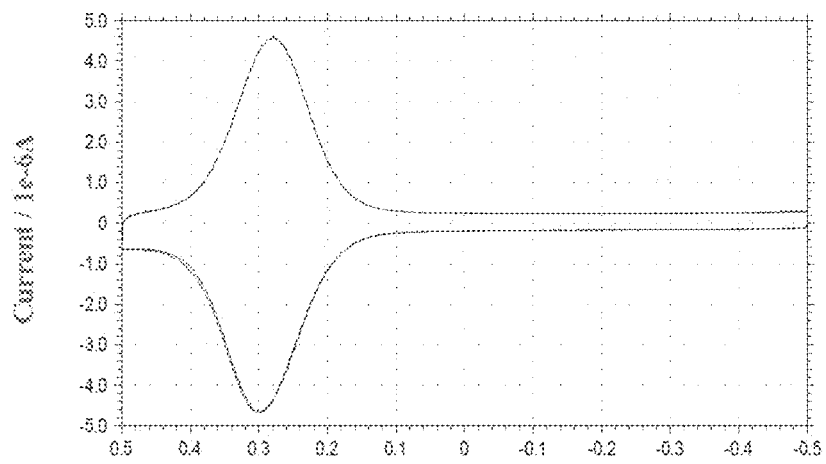
FIG. 19A shows an initial cyclic voltammogram for a 1,1' Fc with an unreacted functional group consisting of a PSM (peroxide sensitive moiety) and a SIM (self immolative moiety).
Figure 19B:
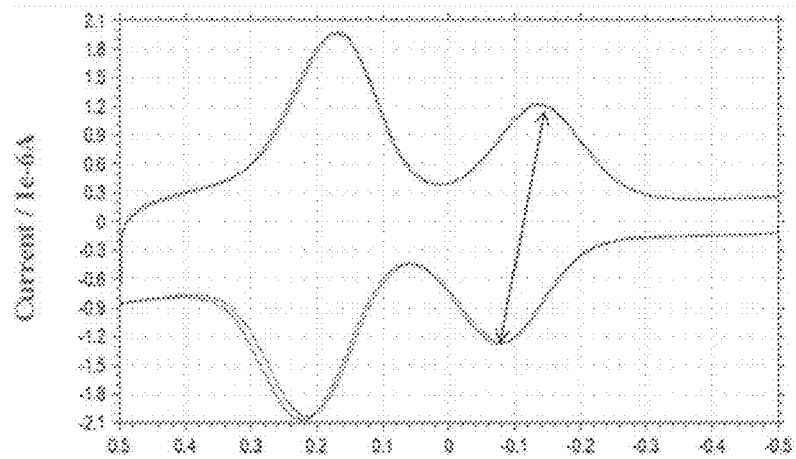
FIG. 19B shows the response of the 1,1' EAM following reaction with hydrogen peroxide. The second peak that appears once the PSM has reacted and the SIM is removed has significant peak splitting and small peak separation from the first peak.
Figure 19C:
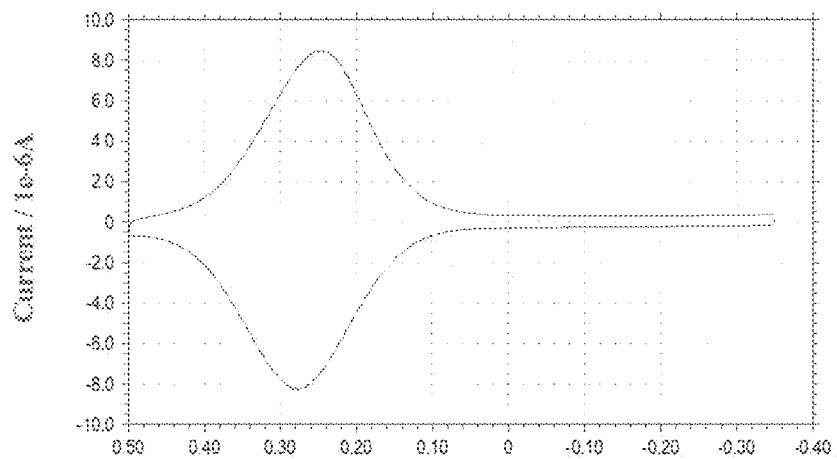
FIG. 19C shows an initial cyclic voltammogram for a 1,3-Fc with an unreacted functional group consisting of a PSM (peroxide sensitive moiety) and a SIM (self immolative moiety).
Figure 19D:
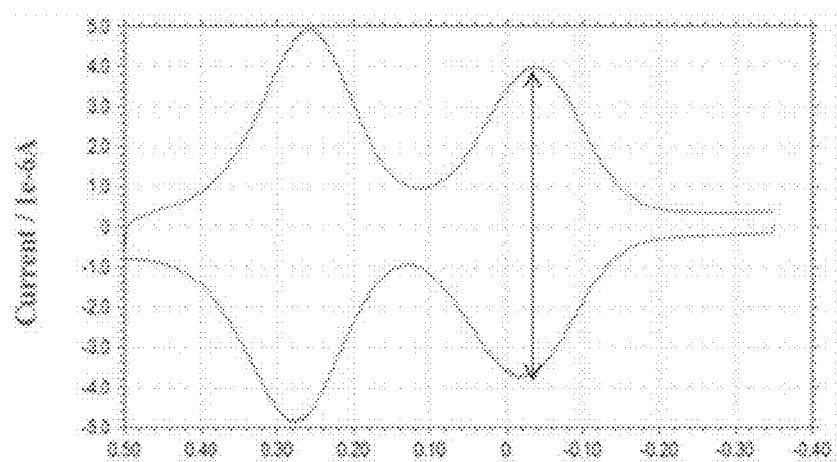
FIG. 19D shows the response of the 1,3-EAM following reaction with hydrogen peroxide. The second peak that appears once the PSM has reacted and the SIM is removed has no peak splitting and larger peak separation from the first peak, as compared with 19B.
Figure 20A:
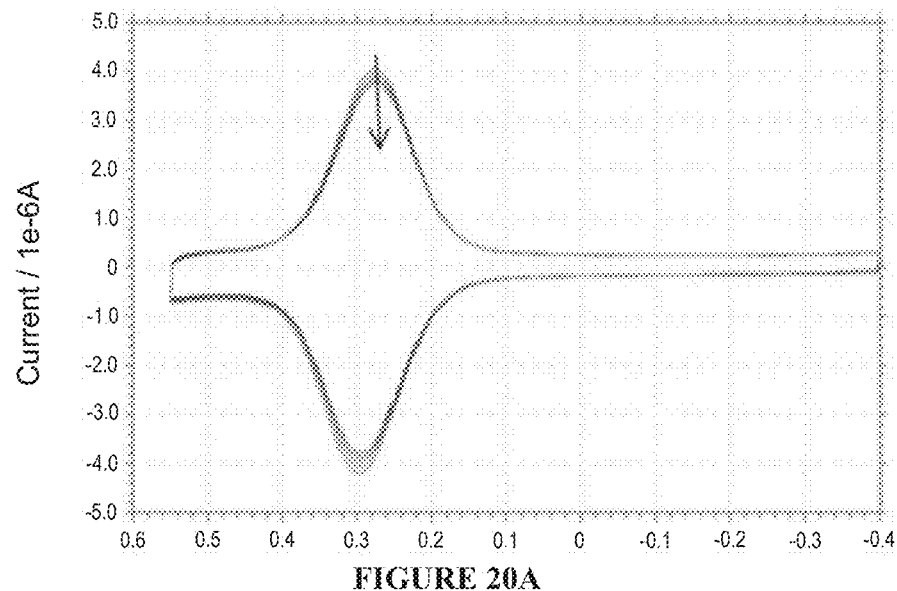
FIG. 20A shows an initial cyclic voltammogram for a 1,1'-Fc scanned multiple times (20 times) and it is shown that the peak current decreases continuously suggesting that the 1-1' compound within the monolayer is not stable.
Figure 20B:
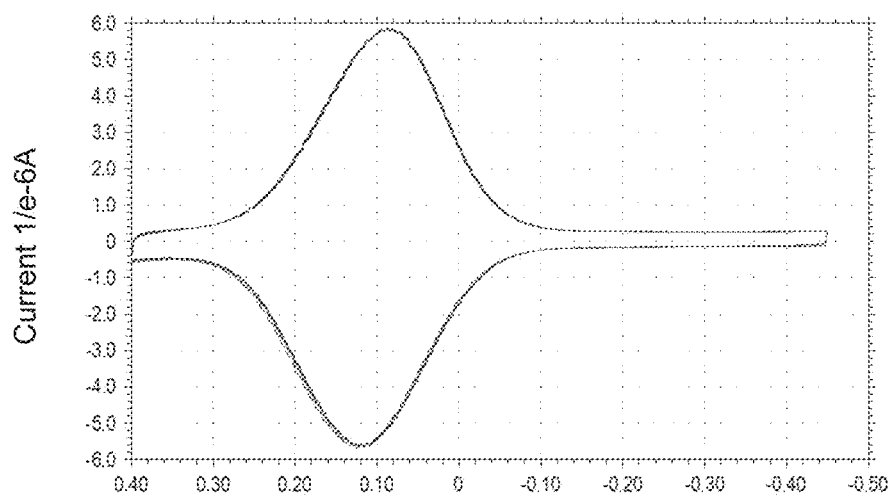
FIG. 20B shows an initial cyclic voltammogram for a 1,3-Fc scanned multiple times (20 times) and it is shown that the peak current is stable suggesting that the 1,3-Fc compound within the monolayer is very stable.

The synthesis of 1-4 is shown in FIGS. 13 and 14 starting from 6 (Organometallics, 1984, 3, 653). Intermediates 10 (Angew. Chem. Int. Ed., 2009, 48, 4406) and 14 (Comm. 2002, 32, 2669) were prepared as described as previously. FIG. 19C shows a representative cyclic voltammogram (CV) for a dilute SAM of 1 with undecanethiol (on a Au electrodes at scan rate of 10 V/Sec). The CV contains a single, reversible redox wave with an apparent formal potential ($E^{0'}$) of 280 mV (vs. Ag/AgCl), an oxidative and reductive peak current ratio near unity, and a peak splitting of 29 mV consistent with well-behaved electroactive ferrocene SAMs known in the art.

wash. The larger shift for 2 can be reasonably explained by a more ordered SAM than 5 where more reactive functional groups are exposed to solution due to the rigid 1,3-ferrocene architecture.

Example 3

1,3-Disubstituted Ferrocene EAMs 21-24

Abbreviations used: DCM, dichloromethane; HOAc, acetic acid; PPh3, triphenylphosphine; THF, tetrahydrofuran;

EDC, 1-ethyl-3-(3-dimethylaminopropyl)carbodiimide; KOH, potassium hydroxide; TFA, trifluoroacetic acid; TES, triethylsilane; DPPA, diphenylphosphoryl azide; TEA, triethylamine; DBTC, di-n-dibutyltin dilaurate; NaH, sodium hydride; MeI, iodomethane; DMAP, dimethylaminopyridine.

Figure 15:
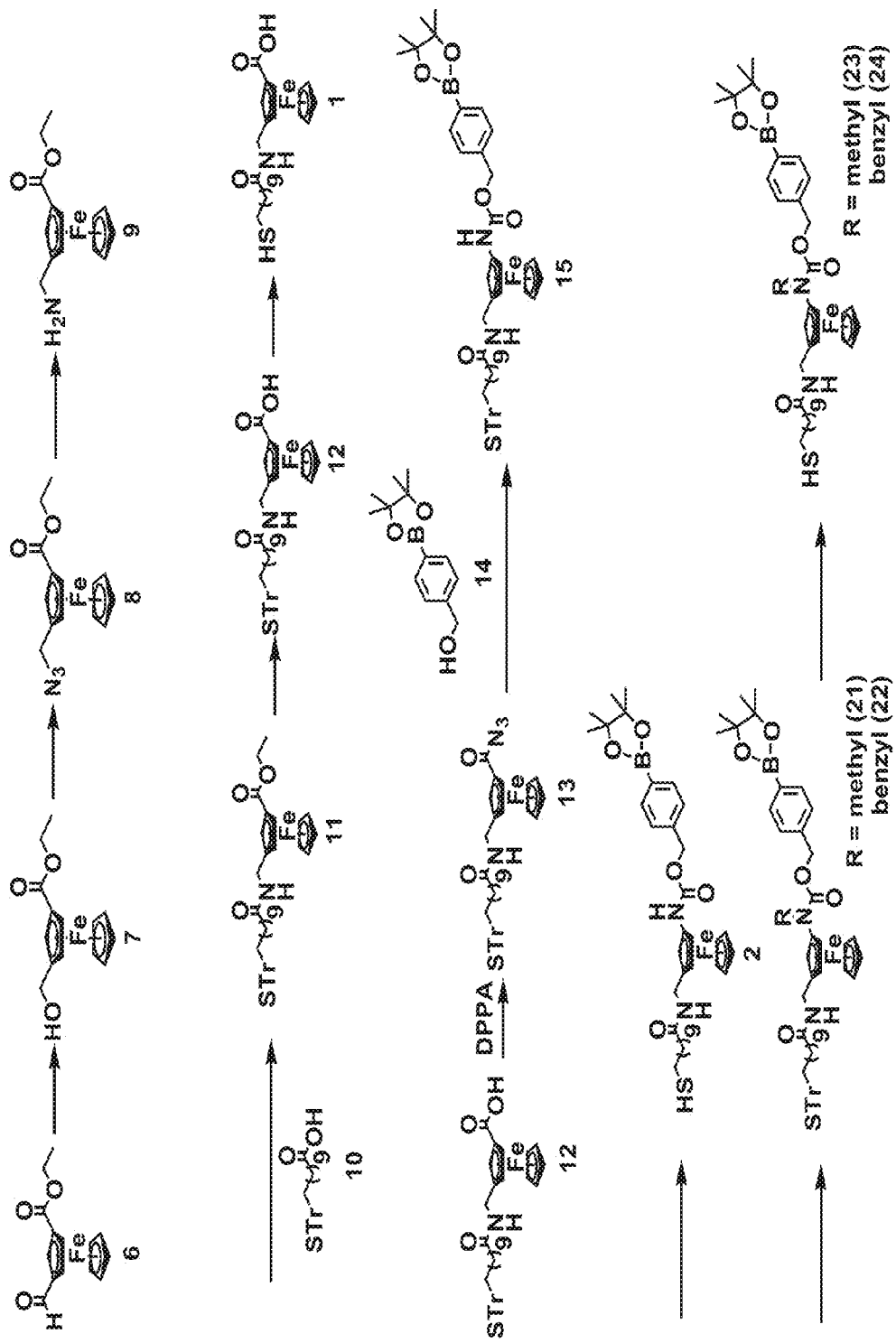
FIG. 15 shows a synthetic scheme detailing the production of Compounds 23 and 24.

Another series of 1,3-disubstituted ferrocene derivatives (21-24, FIG. 15) were synthesized with different functional moieties and organosulfur anchoring groups for SAM formation on gold. To a 0° C. solution of compound 6 (0.215 g, 0.75 mmol) in DCM (10 mL) was added sodium borohydride (0.114 g, 3.00 mmol). MeOH (6 mL) was added slowly over 15 min. The reaction was stirred and warmed to room temperature for 1 h. The reaction was concentrated under reduced pressure and the crude residue was dissolved in EtOAc (100 mL), washed with brine (3×100 mL), dried over $Na_2SO_4$, filtered, and concentrated under reduced pressure to a crude solid. Purification by column chromatography yielded 7 as an orange solid (197 mg, 0.68 mmol, 91%).

A solution of compound 7 (0.535 g, 1.86 mmol) and sodium azide (0.726 g, 11.2 mmol) in AcOH (35 mL) was stirred at 60° C. for 20 h. The reaction was diluted with EtOAc (200 mL), washed with $NaHCO_3$ (aq) (3×100 mL), dried over $Na_2SO_4$, filtered, and concentrated under reduced pressure to a crude brown oil. Purification by column chromatography yielded 8 as an orange oil (0.441 g, 1.41 mmol, 76%).

A solution of compound 8 (0.430 g, 1.37 mmol) and triphenylphosphine (0.431 g, 1.64 mmol) in THF (25 mL) was stirred at 60° C. for 20 h. The reaction was concentrated under reduce pressure to a crude oil which was purified by column chromatography to yield 9 as a dark orange oil (0.371 g, 1.29 mmol, 94%).

A solution of 11-mercaptoundecanoic acid (2.70 g, 12.4 mmol), trityl chloride (4.14 g, 14.8 mmol), and DIPEA (5.17 mmol, 28.7 mmol) in toluene (40 mL) was stirred at room temperature for 20 h. The reaction was concentrated under reduced pressure and the crude residue was dissolved in DCM (100 mL), washed with $H_2O$ (3×100 mL), dried over $Na_2SO_4$, filtered, and concentrated under reduced pressure to a crude yellow oil. Purification by column chromatography yielded 10 as a white solid (4.14 g, 73%).

To a 0° C. solution of compound 9 (0.355 g, 1.24 mmol) and 10 (0.571 g, 1.24 mmol) in DCM (30 mL) was added 1-[3-(dimethylamino)propyl]-3-ethylcarbodiimide HCl (0.249 g, 1.30 mmol). After stirring for 5 h the reaction was concentrated under reduced pressure to a crude brown oil. Purification by column chromatography yielded 11 as a viscous orange oil (0.724 g, 0.99 mmol, 80%).

To a solution of compound 11 (0.720 g, 0.99 mmol) in EtOH (30 mL) was added a solution of potassium hydroxide (0.333 g, 5.93 mmol) in $H_2O$ (3 mL). The reaction was heated to 70° C. After stirring for 24 h, the reaction was concentrated under reduced pressure to crude residue. The crude residue was dissolved in $H_2O$ (100 mL), acidified to pH=4.0, extracted with DCM (4×100 mL), dried over $Na_2SO_4$, filtered, and concentrated under reduced pressure to an orange oil. The orange oil was purified by column chromatography to yield 12 as a golden yellow solid (0.589 g, 0.84 mmol, 85%).

Compound 1

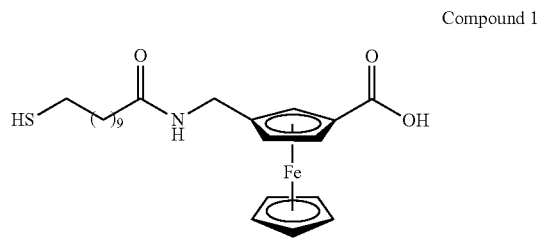

To a solution of compound 12 (0.130 g, 0.19 mmol) and triethylsilane (591 µL, 3.7 mmol) in DCM (5 mL) was added a solution of TFA (0.5 mL) in DCM (5 mL). The reaction was stirred for 16 h and concentrated to a crude orange oil. Purification by column chromatography yielded 1 as a yellow oil (0.078 g, 0.17 mmol, 92%).

To a solution of compound 12 (0.456 g, 0.65 mmol) in THF (30 mL) was added diphenylphosphoryl azide (168 µL, 0.78 mmol) followed by triethylamine (136 µL, 0.98 mmol). The reaction was stirred for 20 h and concentrated under reduced pressure to a crude red oil. Purification by column chromatography yielded 13 as a red/orange solid (0.400 g, 0.55 mmol, 85%).

To a solution of compound 13 (0.298 g, 0.41 mmol) and 14 (0.106 g, 0.45 mmol) in toluene (30 mL) was added di-n-butyltin dilaurate (12 µL, 0.002 mmol). The reaction was stirred at 100° C. for 4 h and concentrated under reduced pressure to a crude brown oil. Purification by column chromatography yielded 15 as a golden yellow oil (0.305 g, 0.33 mmol, 80%).

Compound 2

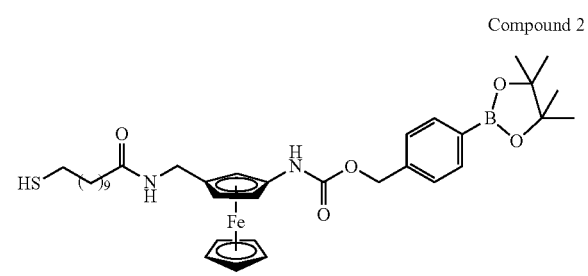

To a solution of compound 15 (0.134 g, 0.14 mmol) in DCM (2 mL) was added a solution of trifluoroacetic acid (200 µL), triethylsilane (115 µL, 0.72 mmol) in DCM (2 mL). The reaction was stirred at room temperature for 3 h and concentrated under reduced pressure to a crude brown oil. Purification by column chromatography yielded 2 as a yellow solid (0.072 g, 0.10 mmol, 72%).

Compound 21

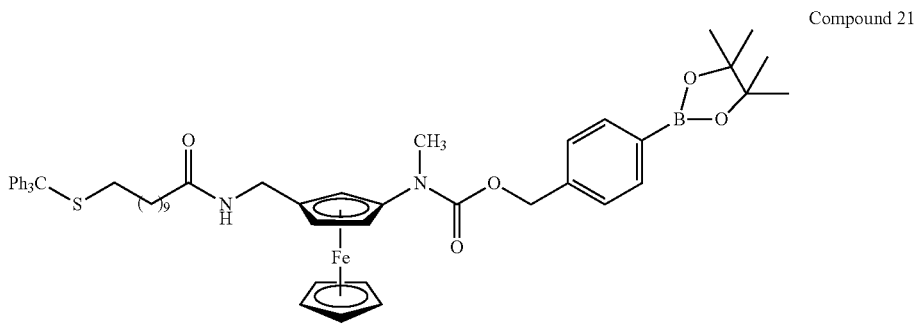

To a 0° C. solution of compound 15 (0.065 g, 0.07 mmol) in THF (3 mL) was added iodomethane (34 μL, 0.70 mmol) followed by sodium hydride (0.017 g, 0.70 mmol). The reaction stirred for 1.5 h and was quenched with $H_2O$ (50 mL). The crude product was dissolved in EtOAc (50 mL), washed with $H_2O$ (3×50 mL), dried over $Na_2SO_4$, filtered, and concentrated to a crude yellow oil. Purification by column chromatography yielded 21 as a yellow oil (0.045 g, 0.05 mmol, 68%).

Compound 22

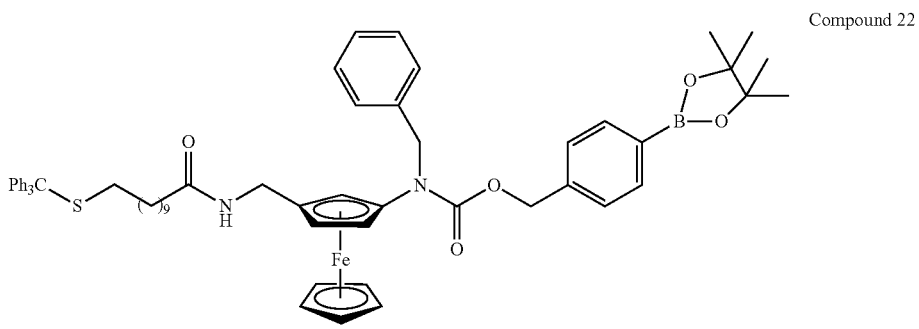

Compound 22 was obtained following the same procedure as for 21 but substituting benzylchloride for iodomethane.

Compound 23

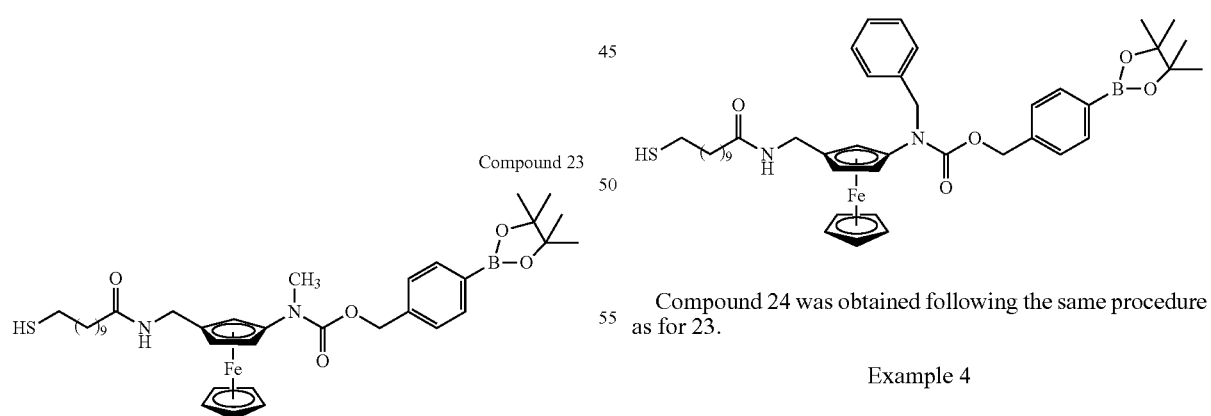

Compound 24

To a solution of compound 21 (0.040 g, 0.042 mmol) in DCM (1 mL) was added a solution of trifluoroacetic acid (100 μL) and triethylsilane (34 μL, 0.21 mmol) in DCM (1 mL). The reaction was stirred at room temperature for 3 h and concentrated under reduced pressure to a crude brown oil. Purification by column chromatography yielded 23 as a yellow oil (0.024 g, 0.033 mmol, 79%).

Compound 24 was obtained following the same procedure as for 23.

Example 4

1,3-Disubstituted Ferrocene EAMs 31

Figure 16A:
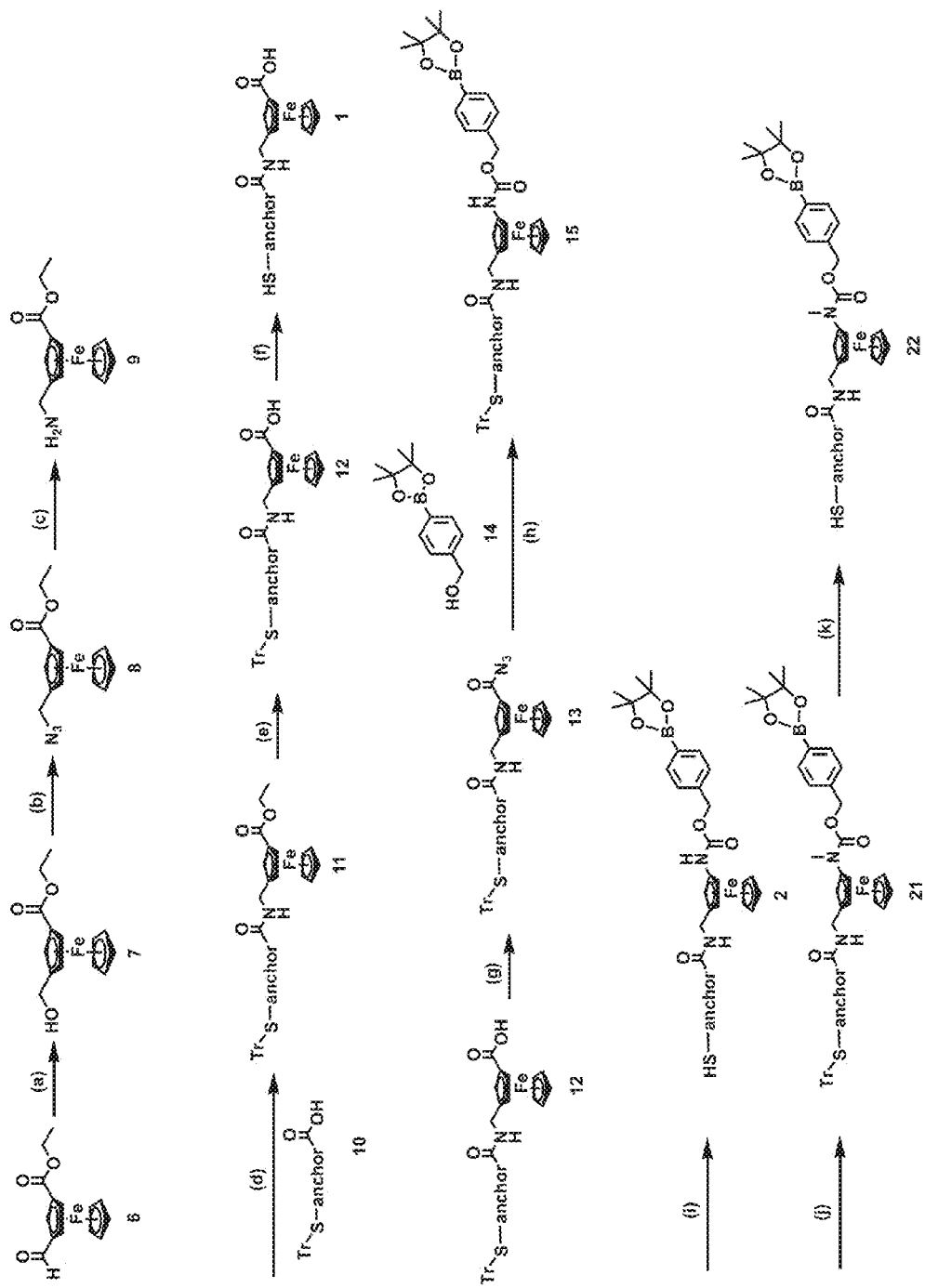
FIG. 16A shows a synthetic scheme detailing Compounds similar to 23 and 24 with different options for anchors, including oligomethylene, oligophenylene, oligophenylene(ethynylene), and polyethyleneglycol.
Figure 16B:
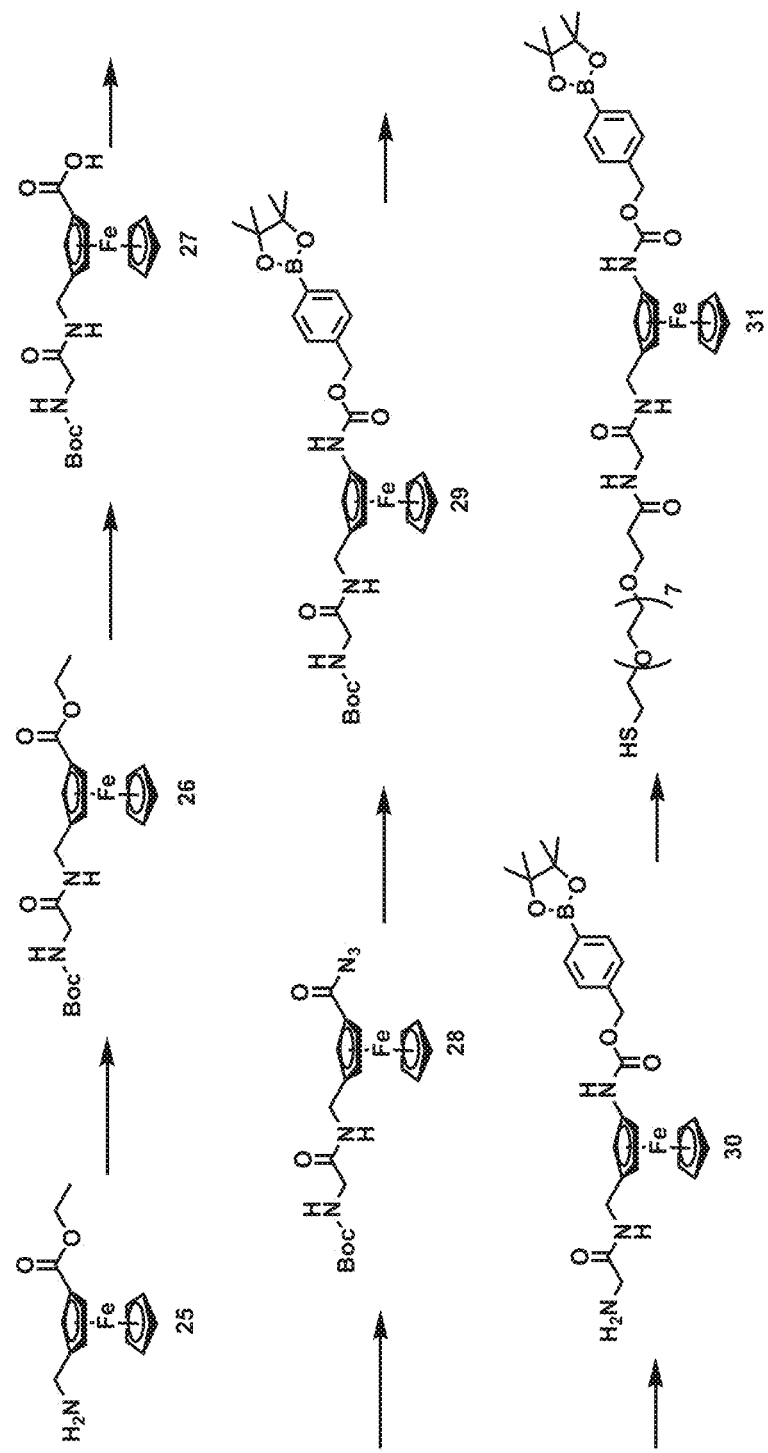
FIG. 16B shows a synthetic scheme detailing compounds similar to 23 and 24 with polyethyleneglycol as an anchor.
Figure 17:
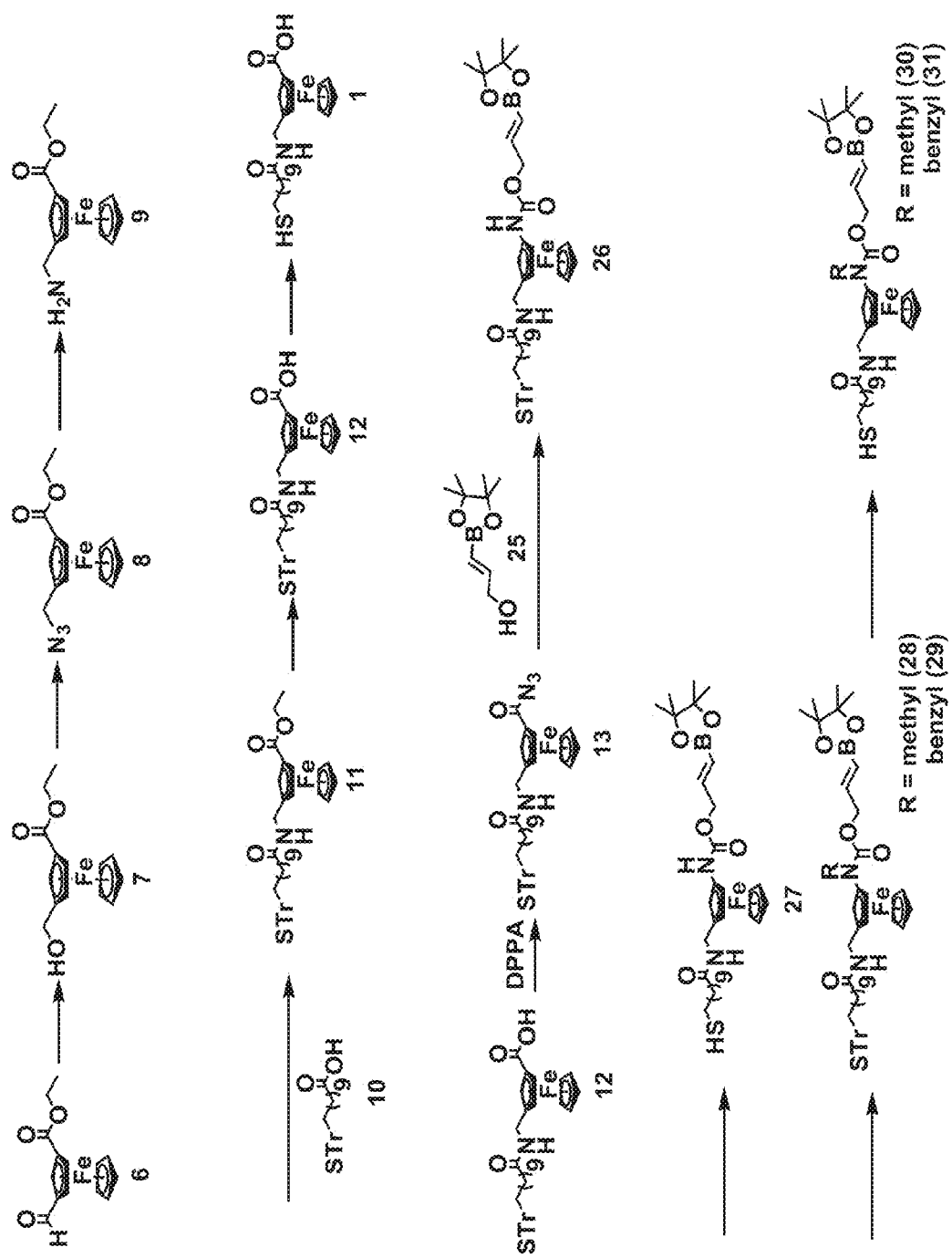
FIG. 17 shows a synthetic scheme detailing the production of novel compounds that have alternative self immolative moieties (SIM) within their functional group.

As shown in FIG. 16B, to a 0° solution of 25 (0.259 g, 0.90 mmol) in DCM (25 mL) was added BOC-glycine (0.269 g, 153 mmol), HOBT (0.235 g, 1.53 mmol), and EDC (0.311 g, 1.62 mmol). The reaction was stirred for 19 h and concentrated under reduced pressure. Purification by column chromatography yielded 26 as a dark yellow oil (0.397 g, 0.89 mmol, 99%).

To a solution of 26 (0.397 g, 0.89 mmol) in ethanol (30 mL) was added a solution of potassium hydroxide (0.301 g, 5.36 mmol) in H$_2$O (3 mL). The reaction was stirred at 70° C. for 18 h and concentrated under reduced pressure. The crude material was dissolved in H$_2$O (100 mL) and DCM (100 mL) and acidified to pH=4 with HCl (aq). The crude material was extracted with DCM (3×100 mL), dried over Na$_2$SO$_4$, filtered, and concentrated. Purification by column chromatography yielded 27 as a yellow oil (0.235 g, 0.56 mmol, 63%).

To a solution of 27 (0.235 g, 0.56 mmol) in THF (20 mL) was added diphenylphosphoryl azide (146 µL, 0.68 mmol) followed by triethylamine (118 µL, 0.85 mmol). The solution was stirred for 40 h and concentrated under reduced pressure. Purification by column chromatograph yielded 28 as a red oil (0.155 g, 0.35 mmol).

To a solution of 28 (0.155 g, 0.35 mmol) in toluene (4 mL) was added 14 (0.090 g, 0.39 mmol) followed by di-n-butyltin dilaurate (12 µL, 0.002 mmol). The reaction was stirred at 100° C. for 3 h and concentrated under reduced pressure. Purification by column chromatograph yielded 29 as a yellow oil (0.169 g, 0.26 mmol, 74%).

To a solution of 29 (0.031 g, 0.048 mmol) in DCM (1 mL) was added a solution of triethylsilane (38 µL, 0.24 mmol) and TFA (0.5 mL) in DCM (0.5 mL). The solution was stirred for 2 h and concentrated under reduced pressure. The crude material was dissolved in H$_2$O (50 mL), basified to pH=10, extracted with DCM (3×50 mL), dried over Na$_2$SO$_4$, filtered, and concentrated. Purification by column chromatography yielded 30 as a pale yellow solid (0.019 g, 0.035 mmol, 73%).

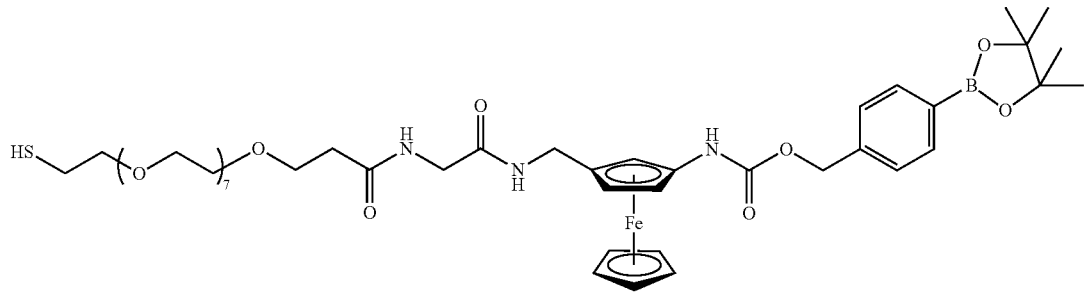

Compound 31

To a solution of PEG Thiol Acid (0.046 g, 0.100 mmol) in THF (1 mL) was added HATU (0.033 g, 0.086 mmol) followed by 30 (0.043 g, 0.079 mmol). The solution was stirred for 1 h and DMF (0.5 mL) was added. The solution was stirred for 21 h and concentrated under reduced pressure. Purification by column chromatograph yielded 31 as a pale yellow solid (0.019 g, 0.019 mmol, 24%).

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

We claim:
1. A ferrocene compound of formula:

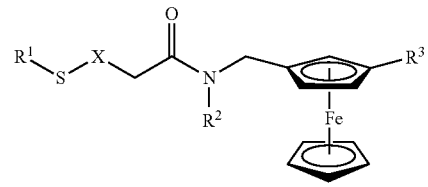

wherein:
$R^1$ is hydrogen, —S—C1-C$_{20}$ alkyl, —S—C$_2$-C$_{20}$ alkenyl, or —S—C$_2$-C$_{20}$ alkynyl,
X is —C$_1$-C$_{20}$ alkyl-, —C$_2$-C$_{20}$ alkenyl-, —C$_2$-C$_{20}$ alkynyl-, —X$^1$—CONH—, —X$^1$—CO$_2$—, or —X$^1$—OCNH—, wherein X$^1$ is selected from the group consisting of polyoxyalkylene, polymethylene, oligophenylene, and polyphenylene(ethynylene);
$R^2$ is hydrogen or C$_1$-C$_6$ alkyl; and
$R^3$ is —NR$^4$R$^5$, —CO$_2$R$^5$, —CONR$^4$R$^5$, or —NR$^5$CO$_2$—R$^6$;
$R^4$ is hydrogen, or C$_1$-C$_6$ alkyl;
$R^5$ is hydrogen, C$_1$-C$_6$ alkyl, C$_2$-C$_6$ alkenyl, C$_2$-C$_6$ alkynyl, aryl(C$_1$-C$_6$ alkyl), aryl(C$_2$-C$_6$ alkenyl), heteroaryl(C$_1$-C$_6$ alkyl), or heteroaryl(C$_2$-C$_6$ alkenyl), wherein each is optionally substituted with one to four substituents selected from the group consisting of halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$(C$_1$-C$_6$ alkyl), —CONH$_2$, —CON(C$_1$-C$_6$ alkyl)$_2$, and peroxide sensitive moiety; and
$R^6$ is C$_1$-C$_6$ alkyl, C$_2$-C$_6$ alkenyl, C$_2$-C$_6$ alkynyl, aryl(C$_1$-C$_6$ alkyl), aryl(C$_2$-C$_6$ alkenyl), heteroaryl(C$_1$-C$_6$ alkyl), or heteroaryl(C$_2$-C$_6$ alkenyl), wherein each is optionally substituted with one to four substituents selected from the group consisting of halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$(C$_1$-C$_6$ alkyl), —CONH$_2$, —CON(C$_1$-C$_6$ alkyl)$_2$, and peroxide sensitive moiety.

2. A ferrocene compound of claim 1, wherein $R^1$ is hydrogen or —S—C$_1$-C$_{20}$ alkyl.

3. A ferrocene compound of claim 1, wherein X is —C$_1$-C$_{20}$ alkyl-, —C$_2$-C$_{20}$ alkenyl-, or —C$_2$-C$_{20}$ alkynyl-.

4. A ferrocene compound of claim 3, wherein X is nonylene.

5. A ferrocene compound of claim 1, wherein X is —$X^1$—CONH—, —$X_1$—$CO_2$—, or —$X^1$—OCNH—, and wherein $X^1$ is selected from the group consisting of polyoxyalkylene, polymethylene, oligophenylene, and polyphenylene(ethynylene).

6. A ferrocene compound of claim 5, wherein X is —$X^1$—CONH—, and $X^1$ is polyoxyalkylene.

7. A ferrocene compound of claim 1, wherein $R^3$ is —$NR^4R^5$, —$CO_2R^5$, or —$CONR^4R^5$.

8. A ferrocene compound of claim 7, wherein $R^3$ is —$NH_2$, —$CO_2(C_1$-$C_6$ alkyl) or —$CO_2H$.

9. A ferrocene compound of claim 1, wherein $R^3$ is —$CONR^4R^5$; $R^4$ is hydrogen or $C_1$-$C_6$ alkyl; and $R^5$ is $C_1$-$C_6$ alkyl, aryl($C_1$-$C_6$ alkyl), or heteroaryl($C_1$-$C_6$ alkyl).

10. A ferrocene compound of claim 1, wherein $R^3$ is —$NR^5CO_2$—$R^6$; and $R^5$ is hydrogen, $C_1$-$C_6$ alkyl, or aryl($C_1$-$C_6$ alkyl).

11. A ferrocene compound of claim 10, wherein $R^6$ is aryl($C_1$-$C_6$ alkyl) or $C_2$-$C_6$ alkenyl, where each is optionally substituted with peroxide sensitive moiety.

12. A ferrocene compound of claim 11, wherein the peroxide sensitive moiety is 4,4,5,5-tetramethyl-1,3,2-dioxaborolanyl.

13. A ferrocene compound of claim 1, wherein the peroxide sensitive moiety is selected from the group consisting of:

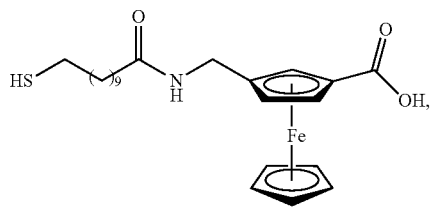

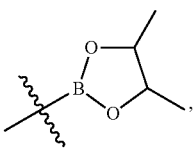

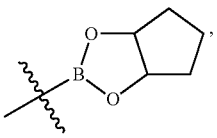

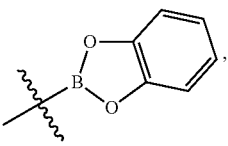, and

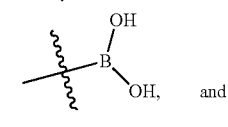

14. A ferrocene compound of claim 1, wherein $R^3$ is

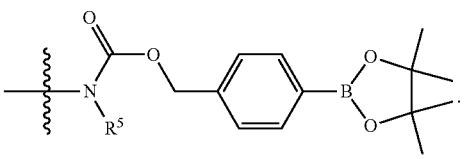

15. A ferrocene compound of claim 1, which is:

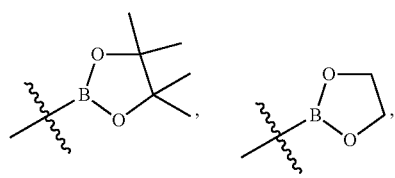

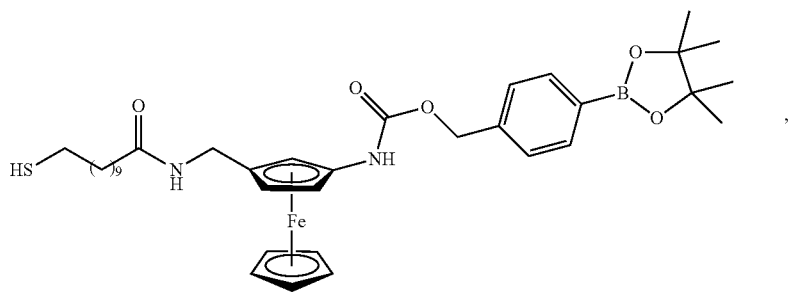

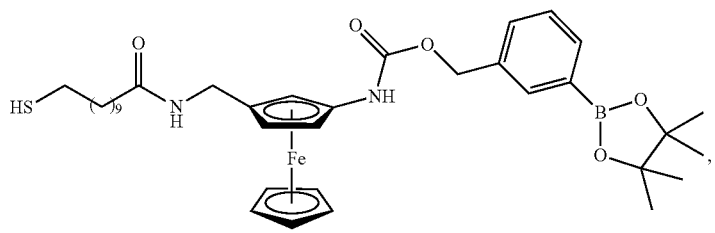

-continued
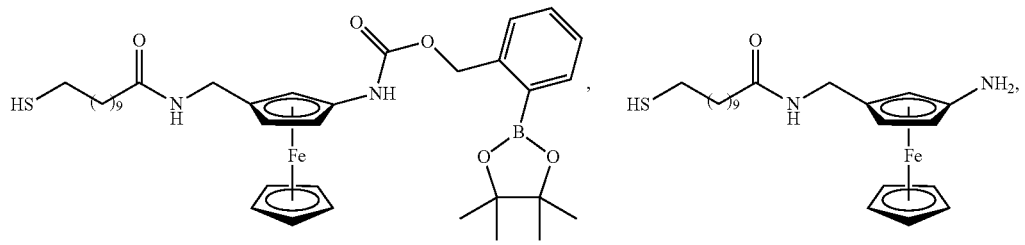
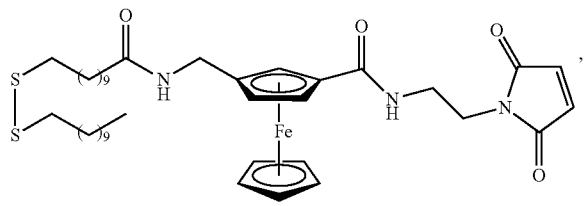
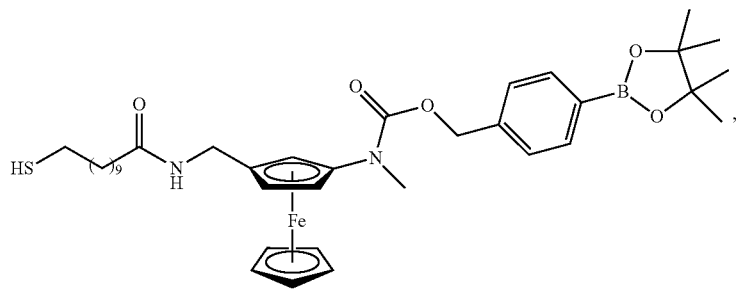
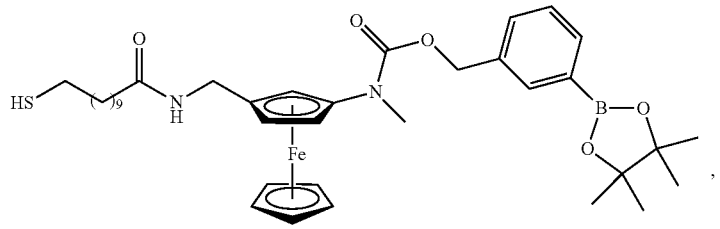
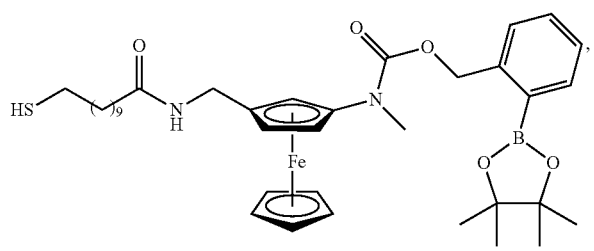
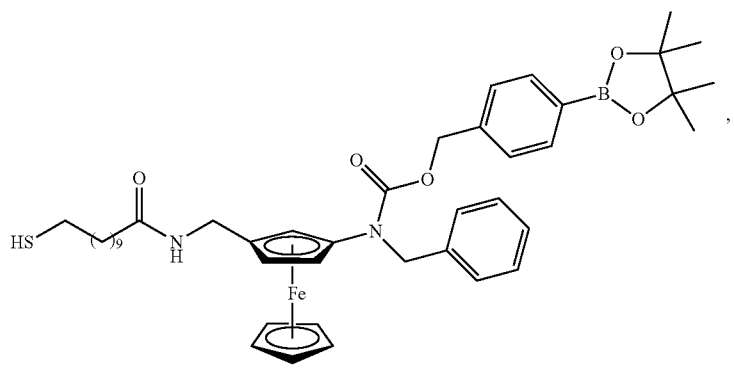

-continued

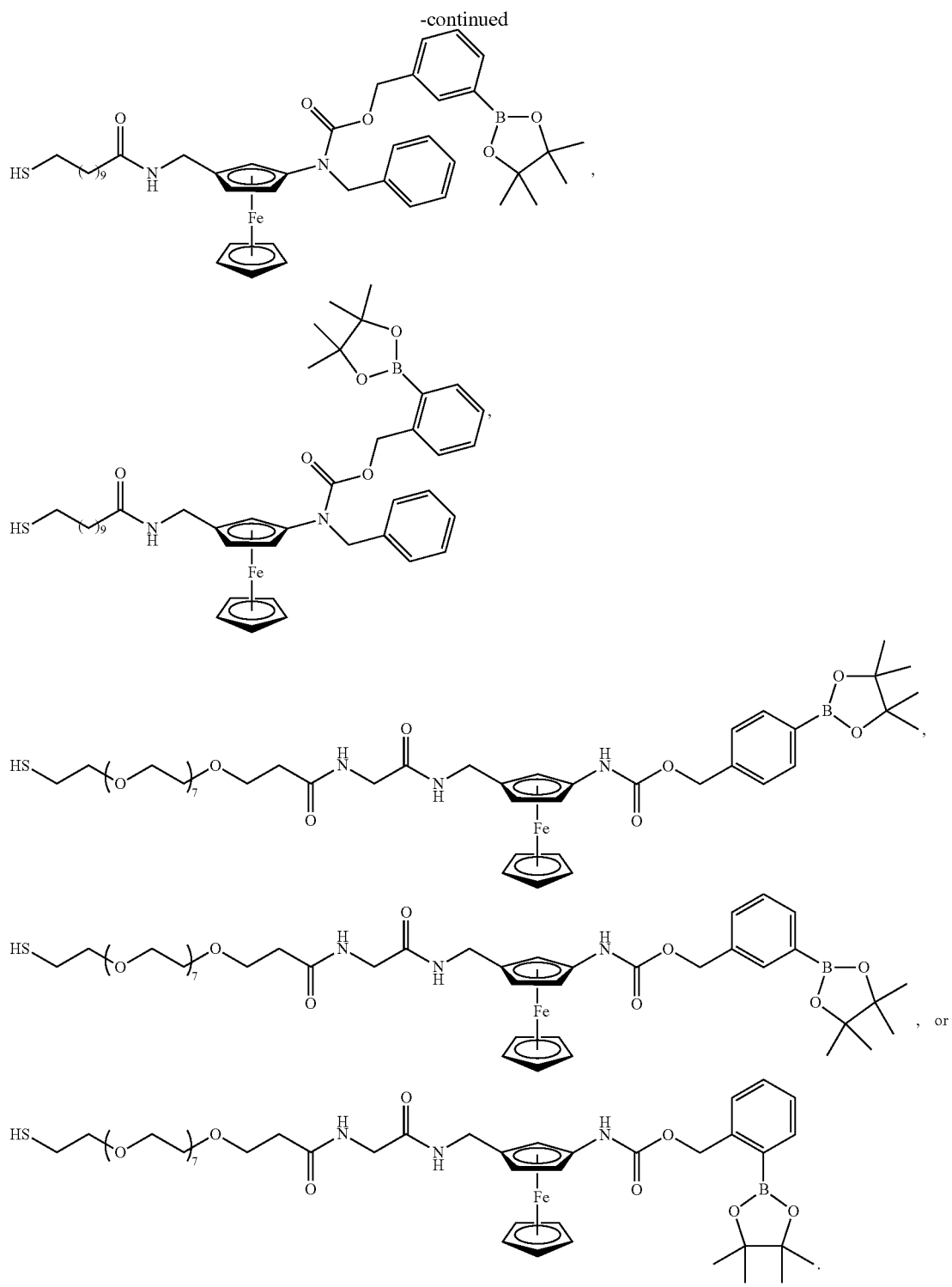

16. A device comprising an electrode comprising:
(i) an optional self-assembled monolayer (SAM); and
(ii) an electroactive active moiety (EAM), said EAM comprising a 1,3-disubstituted ferrocene.

17. The device of claim 16, wherein said 1,3-disubstituted ferrocene comprises a compound of claim 1.

18. The device of claim 16, wherein said 1,3-disubstituted ferrocene further comprises a functional group.

19. The device of claim 18, wherein the functional group comprises a self-immolative moiety and a peroxide sensitive moiety.

20. The device of claim 18, wherein said functional group comprises a capture ligand.

21. The device of claim 18, wherein said functional group is selected from the group consisting of moieties comprising a maleimide, an imidoester, N-hydroxysuccinimidyl, alkyl halide, aryl halide, alpha-haloacyl, and pyridyl disulfide.

22. The device of claim 16, wherein said electrode further comprises a functional group.

23. The device of claim 16, further comprising a self-assembled monolayer (SAM).

24. The device of claim 23, wherein the SAM is a non-conductive oligomer or a conductive oligomer.

25. A device comprising an electrode comprising a self-assembled monolayer (SAM), wherein said SAM comprises a compound having the formula:

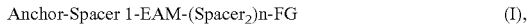

Anchor-Spacer 1-EAM-(Spacer$_2$)n-FG  (I), wherein said anchor comprises a cyclic-disulfide group,
EAM is a 1,3-disubstituted ferrocene,
FG is a functional group,
Spacer 1 is a SAM forming species,
Spacer 2 is a linker, and
n=0 or 1.

26. A device comprising an electrode comprising a self-assembled monolayer (SAM), wherein said SAM comprises a compound having the formula:

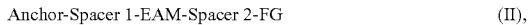

Anchor-Spacer 1-EAM-Spacer 2-FG  (II), wherein said anchor is linked to said electrode group through a disulfide group,
EAM is a 1,3-disubstituted ferrocene,
FG is a functional group,
Spacer 1 is either insulating or conducting, and
Spacer 2 is an optional linker.

27. A method for detecting one or more target analytes m a test sample, said method comprising:
(a) contacting the test sample with a capture binding ligand under conditions such that the capture binding ligand specifically binds to a target analyst, if present, in said test sample to form a first complex, the capture binding ligand bound to a first solid support;
(b) contacting said first complex, if present, to a soluble capture ligand to form a second complex, wherein said soluble capture ligand comprises a peroxide-generating system;
(c) contacting said second complex with a substrate for said peroxide-generating system under conditions wherein a peroxide is generated to form an assay mixture;
(d) contacting the assay mixture with a second solid support comprising an electrode comprising (i) a self-assembled monolayer (SAM) of an electroactive active moiety (EAM), or (ii) an EAM and optional SAM, wherein said EAM comprises a 1,3-disubstituted ferrocene, a self-immolative moiety, and a peroxide sensitive moiety (PSM) and has a first E$^0$, and wherein said peroxide reacts with said PSM to release said SIM from said EAM and result in said EAM having a second E$^0$; and having a second E$^0$;
(f) measuring the electrochemical properties of said EAM at the first E$^0$ and at the second E$^0$; and
(g) detecting said target analyte from said electrochemical properties.

28. A method for detecting one or more target analytes in a test sample, said method comprising:
(a) contacting the test sample with a soluble capture ligand to form a first complex, wherein said soluble capture ligand comprises a peroxide-generating system;
(b) contacting said first complex, if present, with capture binding ligand under conditions such that the capture binding ligand specifically binds to a target analyst to form a second complex, the capture binding ligand bound to a first solid support;
(c) contacting said second complex with a substrate for said peroxide-generating system under conditions wherein a peroxide is generated to form an assay mixture;
(d) contacting the assay mixture with a second solid support comprising an electrode comprising (i) a self-assembled monolayer (SAM) of an electroactive active moiety (EAM) or (ii) an EAM and optional SAM, wherein said EAM comprises a 1,3-disubstituted ferrocene, a self-immolative moiety, and a peroxide sensitive moiety (PSM) and has a first E$^0$, and wherein said peroxide reacts with said PSM to release said SIM from said EAM and result in said EAM having a second E$^0$; and having a second E$^0$;
(f) measuring the electrochemical properties of said EAM at the first E$^0$ and at the second E$^0$; and
(g) detecting said target analyte from said electrochemical properties.

29. The method of claim 27 or 28, further comprising isolating second complex prior to step (c).

30. The method of claim 27 or 28, wherein 1,3-disubstituted ferrocene is a ferrocene compound of formula:

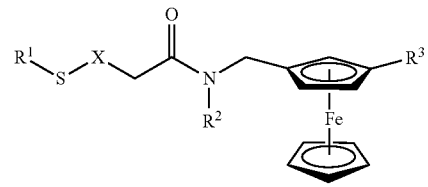

wherein:
$R^1$ is hydrogen, —S—C1-C$_{20}$ alkyl, —S—C$_2$-C$_{20}$ alkenyl, or —S—C$_2$-C$_{20}$ alkynyl,
X is —C$_1$-C$_{20}$ alkyl-, —C$_2$-C$_{20}$ alkenyl-, —C$_2$-C$_{20}$ alkynyl-, —X$^1$—CONH—, —X$^1$—CO$_2$—, or —X$^1$—OCNH—, wherein X$^1$ is selected from the group consisting of polyoxyalkylene, polymethylene, oligophenylene, and polyphenylene(ethynylene);
$R^2$ is hydrogen or C$_1$-C$_6$ alkyl; and
$R^3$ is —NR$^4$R$^5$, —CO$_7$R$^5$, —CONR$^4$R$^5$, or —NR$^5$CO$_2$—R$^6$;
$R^4$ is hydrogen, or C$_1$-C$_6$ alkyl;
$R^5$ is hydrogen, C$_1$-C$_6$ alkyl, C$_2$-C$_6$ alkenyl, C$_2$-C$_6$ alkynyl, aryl(C$_1$-C$_6$ alkyl), aryl(C$_2$-C$_6$ alkenyl), heteroaryl(C$_1$-C$_6$ alkyl), or heteroaryl(C$_2$-C$_6$ alkenyl), wherein each is optionally substituted with one to four substituents selected from the group consisting of halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$(C$_1$-C$_6$ alkyl), —CONH$_2$, —CON(C$_1$-C$_6$ alkyl)$_2$, and peroxide sensitive moiety; and
$R^6$ is C$_1$-C$_6$ alkyl, C$_2$-C$_6$ alkenyl, C$_2$-C$_6$ alkynyl, aryl(C$_1$-C$_6$ alkyl), aryl(C$_2$-C$_6$ alkenyl), heteroaryl(C$_1$-C$_6$ alkyl), or heteroaryl(C$_2$-C$_6$ alkenyl), wherein each is optionally substituted with one to four substituents selected from the group consisting of halogen, —CN, —NO$_2$, N$_3$, C$_1$-C$_6$ alkyl, halo(C$_1$-C$_6$ alkyl), C$_1$-C$_6$ alkoxy, amino, C$_1$-C$_6$alkylamino, diC$_1$-C$_6$alkylamino, —CO$_2$H, —COH, —CO$_2$(C$_1$-C$_6$ alkyl), —CONH$_2$, —CON(C$_1$-C$_6$ alkyl)$_2$, and peroxide sensitive moiety.

* * * * *